(12) United States Patent
Deur

(10) Patent No.: US 11,400,196 B2
(45) Date of Patent: Aug. 2, 2022

(54) CONTROLLED ARTERIAL/VENOUS ACCESS

(71) Applicant: Tomislav Deur, Hollidaysburg, PA (US)

(72) Inventor: Tomislav Deur, Hollidaysburg, PA (US)

( * ) Notice: Subject to any disclaimer, the term of this patent is extended or adjusted under 35 U.S.C. 154(b) by 630 days.

(21) Appl. No.: 16/287,567

(22) Filed: Feb. 27, 2019

(65) Prior Publication Data
US 2019/0290828 A1    Sep. 26, 2019

Related U.S. Application Data

(63) Continuation-in-part of application No. 15/621,292, filed on Jun. 13, 2017, now Pat. No. 11,173,294, which is a continuation-in-part of application No. 14/211,917, filed on Mar. 14, 2014, now Pat. No. 10,105,479.

(60) Provisional application No. 61/788,962, filed on Mar. 15, 2013.

(51) Int. Cl.
*A61M 1/36* (2006.01)
*A61M 39/28* (2006.01)
*A61M 39/02* (2006.01)

(52) U.S. Cl.
CPC .......... *A61M 1/3653* (2013.01); *A61M 39/28* (2013.01); *A61M 39/0208* (2013.01); *A61M 39/0247* (2013.01)

(58) Field of Classification Search
CPC .... A61F 2/06; A61F 2/064; A61B 2017/1135; A61B 2017/1132; A61B 2017/1107; A61M 39/28; A61M 39/0247; A61M 39/0208; A61M 1/3655; A61M 1/365
See application file for complete search history.

*Primary Examiner* — Leslie R Deak
(74) *Attorney, Agent, or Firm* — Jeffrey R. Ramberg; Steven J. Link

(57) ABSTRACT

Apparatus and methods for controlled arterial/venous access are provided. The apparatus and methods may include a section of tubing anastomosed to a bodily lumen. A lumen clamping means may utilize a clamp manipulator to effectively seal the tubing, and the manipulator may be operated by two fingers. A needle receptor may be utilized, and the receptor may utilize a rotating member to guide a needle inserted from outside the body, in order ensure accurate placement into a channel. The channel may be in liquid communication with the tubing. The manipulator and the needle receptor may be palpable from outside the body.

19 Claims, 42 Drawing Sheets

CONTROLLED ARTERIAL/VENOUS ACCESS

CROSS-REFERENCE TO RELATED APPLICATION

This application is a Continuation in Part of U.S. patent application Ser. No. 15/621,292, which is in turn, a Continuation in Part of U.S. Patent Application No. US 2014/0276327 A1, now issued as U.S. Pat. No. 10,105,479 B2, which is a nonprovisional of U.S. Provisional Application No. 61/788,962, filed on Mar. 15, 2013 each of which is hereby incorporated by reference in its entirety.

FIELD OF TECHNOLOGY

Aspects of the invention relate to a controlled valve for accessing a blood vessel.

BACKGROUND

Various therapeutic treatments require access to blood flowing through a circulatory system. For example, treatments in the fields of hematology, oncology and/or pharmacology may require direct access to circulating blood. Some treatments, such as dialysis, require an extraction and reintroduction of blood. The blood extracted from the body is filtered, waste products are removed and the filtered and "clean" blood is reintroduced into the circulatory system.

To perform dialysis, it is necessary to have access to the blood, while it is in circulation. Additionally, the access to the blood should be arranged to provide a high extraction throughput or flow rate. The flow rate allows a sufficient amount of blood to be extracted within a given period of time. Efficacy of the dialysis procedure may be dependent upon the extraction throughput. Treatment costs as well as patient comfort usually coincide with efficient procedures.

When performing dialysis, one method of accessing the blood is via an intravenous catheter. The catheter may be inserted into a large vein. Large veins, such as the vena cava, jugular vein or femoral vein, allow for a higher extraction throughput than do other veins.

However, a catheter is a foreign body in the vein, and may trigger venous stenosis in or around the vein wall. The venous stenosis may scar and occlude the vein. As a result of the stenosis and occlusion, multiple access sites must be utilized and a patient on long term dialysis may "run out" of usable veins for catheter access. In addition, a catheter protrudes out of a patient's skin, and staving off infection is a common challenge when employing catheter access. However, the patient may desire catheter access because, after insertion, accessing the patient's blood through connection of the catheter to a dialysis machine does not require repeated needle pricks.

Another access method is to surgically form an arteriovenous ("AV") fistula. To form the fistula, a surgeon joins an artery to a vein, bypassing narrow capillaries. Arteries carry blood away from the heart and blood typically flows faster, and at a higher pressure, through arteries than veins. By transferring directly from an artery to a vein without intervening capillaries, blood flows swiftly at a high pressure from the artery into the vein. A fistula is formed by creating an anastomosis between and artery and vein. However, the fistula may take 1-4 months to mature the vein prior to being accessed for dialysis.

After maturity, two needles are inserted into the vein distal to the fistula anastomosis. A first needle extracts blood which is transferred to a dialysis machine. A second needle receives the filtered blood from the dialysis machine and reintroduces the filtered blood into the vein.

A fistula is characterized by lower infection rates than catheter access. However, because the fistula is always "on" and blood is always flowing through the fistula, the fistula may stimulate a "steal syndrome." The steal syndrome occurs when insufficient blood flow reaches the bypassed capillaries. Blood may be drawn through the fistula and returned to general circulation through the vein, preventing adequate blood flow to extremities of a limb. The steal syndrome may result in coldness in the extremities and ischemic tissue damage if severe. Since the fistula is always "on", some patients face issues with cardiac failure since their heart is now tasked with a constantly increased cardiac output. If the patient's heart is unable to perform at such a cardiac output, it can lead to congestive heart failure.

A fistula may also be associated with development of an aneurysm in the vein. While undergoing dialysis, needles must be regularly inserted into veins distal to the fistula to reintroduce blood to the circulatory system. The needle insertions may weaken a wall of the vein, as they must be repeated for every treatment. The repeated needle sticks may be repeated at convenient, or easily accessible, areas in the anatomy, thereby increasing the likelihood of an aneurysm.

Another dialysis access method is to create an AV graft. The graft operates under principles similar to the fistula. The graft is an artificial conduit that transfers blood flow from an artery directly into a vein. Unlike the fistula, the graft joins the artery and vein using a synthetic material. Unlike a fistula, a graft does not need to mature allowing for earlier usage, and may be used in cases where a patient's anatomy is not optimal for creation of a fistula. The graft may be made of a length sufficient to join two blood vessels distant from each other.

However, grafts are made from synthetic materials, and are foreign to the body. While a synthetic graft may be sized ideally to the anatomy, they are associated with a higher rate of thrombosis. The thrombosis may result from stenosis within natural arteries and veins adjacent to the anastomoses at each end of the graft. Grafts are also typically associated with a higher rate of infection than the fistula. Furthermore, like a fistula, a graft cannot be turned "off," and even after completion of a dialysis procedure, blood is constantly flowing through the graft. Again, this situation is not ideal for the tissue which may be transfusing significantly less blood than normal.

It would be desirable to obtain benefits of a fistula/graft without these numerous associated disadvantages. It would be desirable to provide blood access that is associated with a high throughput and that may be "turned off" after a treatment. It would be desirable to provide regular access to blood without damaging a blood vessel as a result of repeated needle pricks. Therefore, it would be very beneficial to provide apparatus and methods for a valve for accessing a blood vessel.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which.

DETAILED DESCRIPTION OF THE DISCLOSURE

Figure 1:
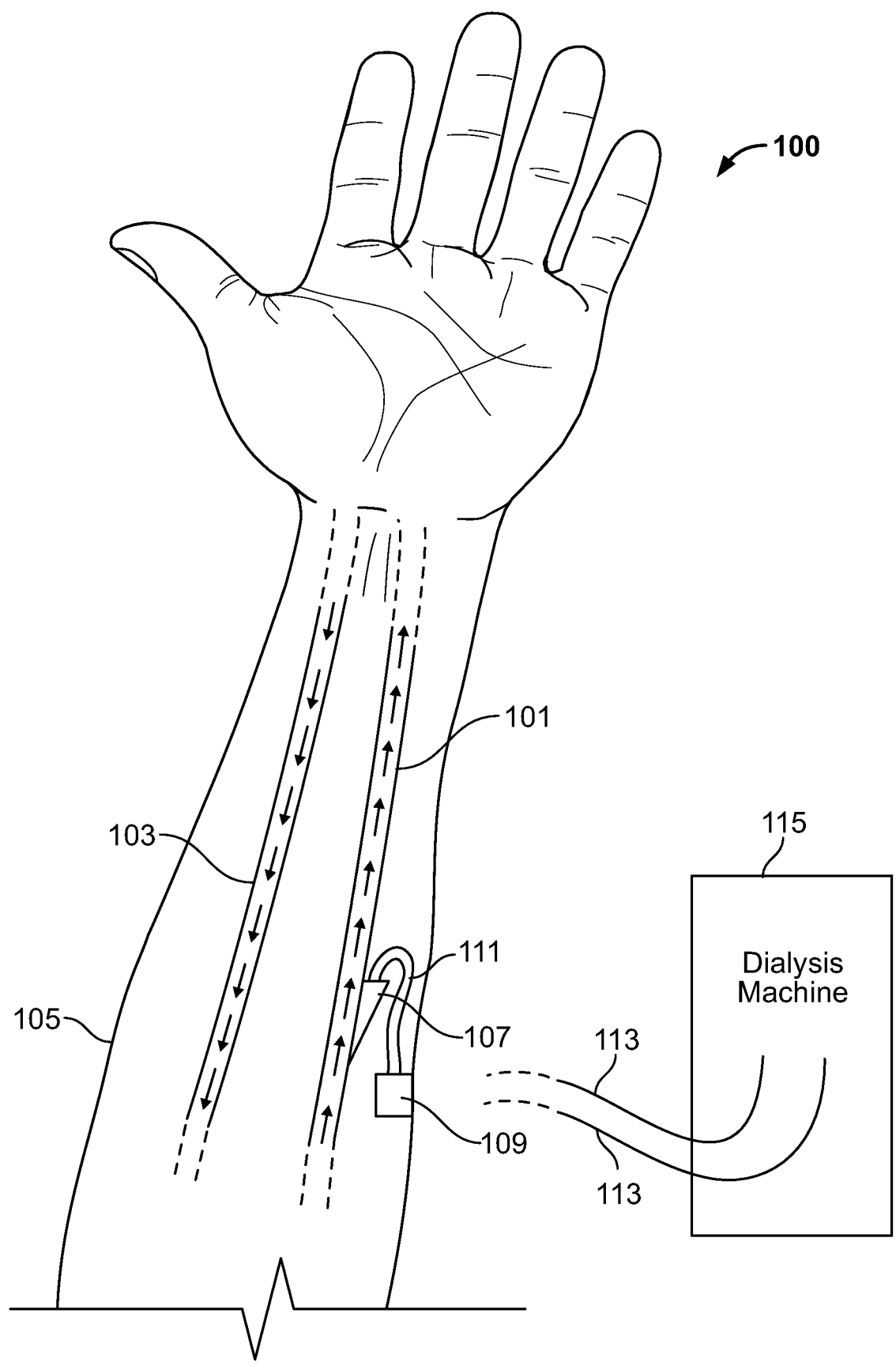
FIG. 1 shows an illustrative therapeutic scenario in accordance with principles of the invention.

Apparatus and methods for a hydraulic access port are provided. In another embodiment, an apparatus and method for an implantable subcutaneous access valve having palpable elements are provided.

Apparatus may include, and methods may involve, a transport system. The transport system may include a port. The port may be coupled to a blood vessel. The blood vessel may be an artery. The blood vessel may be a vein. The blood vessel may be any suitable blood vessel. The port may be coupled to any suitable conduit carrying a medium.

The port may include an expandable chamber. The port may include a rotatable swing-arm. The port may include a sealable passageway. The port may include an orifice. The orifice may allow blood to flow between the blood vessel and the port.

The transport system may include tubing. The tubing may be coupled to the port. The tubing may include a first lumen. The tubing may include a second lumen. The second lumen may be in fluid connection with the expandable chamber. The second lumen may be expandable. The second lumen may be oriented inferiorly with respect to the first lumen. Expansion of the second lumen may be configured to collapse the first lumen. Expansion of the second lumen may be configured to seal the first lumen.

The transport system may include a reservoir. The reservoir may be coupled to the tubing. The reservoir may be coupled to the port. The reservoir may include a first collapsible chamber. The first collapsible chamber may be coupled to the sealable passageway of the port. The first collapsible chamber may be capped with a first membrane.

The reservoir may include a second chamber. The second chamber may be in fluid connection with the second lumen. The second chamber may be in fluid connection with the expandable chamber of the port. The second chamber may be capped with the first membrane. The second chamber may be capped with a second membrane.

The port may include a swing-arm. An injection of a medium into the second chamber may be configured to articulate the swing-arm. Movement of the swing-arm may seal the sealable passageway of the port. The injection of the medium into the second chamber may position the swing-arm over an orifice in the port. Expansion of the expandable chamber of the port may position the swing-arm over the orifice. The position of the swing-arm may be maintained by a pressure in the transport system. The pressure may be maintained, at least in part, by the first and/or second membranes.

The transport system may be a first transport system. Apparatus may include, and methods may involve, a first transport system and a second transport system. The first transport system may be coupled to a first blood vessel. The second transport system may be coupled to a second blood vessel.

Apparatus may include, and methods may involve, a tubing. The tubing may include a first end coupled to a blood vessel. The tubing may include a second end. The second end may be coupled to a subcutaneous reservoir. The tubing may include a first sealable lumen. The first sealable lumen may be configured to transport blood. The tubing may include a second expandable lumen configured to seal the first lumen.

Apparatus may include, and methods may involve, a transport system. The transport system may include a subcutaneous central reservoir. The subcutaneous central reservoir may include a first chamber. The first chamber may be in fluid connection with a lumen of a first tubing. The first chamber may be in fluid connection with a first lumen of a second tubing.

The subcutaneous central reservoir may include a second chamber. The second chamber may be coupled to a second lumen of the first tubing.

The subcutaneous central reservoir may include a third chamber. The third chamber may be coupled to a second lumen end of the second tubing.

The transport system may include a first port. The first port may be coupled to the first lumen of the first tubing. The first port may be coupled to the second lumen of the first tubing.

The transport system may include a second port. The second port may be coupled to the first lumen of the second tubing. The second port may be coupled to the second lumen of the second tubing.

Apparatus may include, and methods may involve, a transport system. The transport system may include a reservoir. The reservoir may include a first chamber. The first chamber may be collapsible and expandable. The reservoir may include a second chamber. The second chamber may be collapsible and expandable.

The transport system may include tubing. The tubing may be coupled to the reservoir using a barb or adapter. The tubing may include a first lumen. The first lumen may link the first chamber to a fluid carrying conduit. The conduit may be a blood vessel. The blood vessel may be anastomized to the tubing.

The tubing may include a second lumen. The second lumen may link the second chamber to a balloon. The second lumen may terminate at the balloon. The second lumen may be in fluid communication with the balloon. The balloon may encircle the first lumen. The balloon may encircle a portion of the first lumen. The balloon may encircle a portion of the tubing that does not compress or deform when the balloon is inflated.

The system may include a clamp. The clamp may be coupled to the tubing. The clamp may be rotatably coupled to the tubing. The clamp may be configured to rotate about a pivot affixed to the tubing.

The clamp may expand about the first lumen in response to inflation of the balloon. The inflation of the balloon may overcome a force biasing the clamp in a closed position. The clamp may compress the first lumen in response to deflation of the balloon. The clamp may compress a section of the first lumen. The clamp may compress the first lumen in a closed position.

Compressing the first lumen may seal the system from the conduit and fluid flowing through the conduit. Compressing the first lumen may allow fluid carried through the conduit to flow without being impeded by the tubing.

The reservoir may include a septum. The septum may include a self-sealing membrane. The reservoir may include a moveable platform. The moveable platform may be disposed between a first chamber and a second chamber of the reservoir.

The reservoir may include a biasing member. The biasing member may be a spring or any suitable pressure source. The biasing member may bias the moveable platform toward the septum. In some embodiments, the biasing member may bias the moveable platform to press against the septum.

The reservoir may include a bladder. The bladder may reside within the second chamber of the reservoir. The bladder may be in fluid communication with the balloon. The second lumen may provide fluid communication between the bladder and the balloon.

Pressure may be applied to the moveable platform. A needle may be inserted into the reservoir through the septum. A tip of the needle may exert pressure on the moveable platform. The pressure may push down on the moveable platform. The moveable platform may include a sloping surface to direct the needle to a center of the platform. The movable platform may be flat, convex, concave or have any suitable surface. In response to the pressure, the moveable platform may compress the bladder. Compressing the bladder may inflate the balloon with fluid transferred from the bladder to the balloon via the second lumen.

The transport system may include a locking mechanism. The locking mechanism may engage when the moveable platform is moved a pre-determined distance away from the septum. After moving the pre-determined distance, a protrusion coupled to the platform may be seated into a well of the locking mechanism. Seating the protrusion in the well may prevent the biasing member of the reservoir from moving the platform toward the septum.

Seating the protrusion in the well may lock the moveable platform in a position that maintains compression of the bladder and corresponding inflation of the balloon. The locking mechanism may be disengaged when the moveable platform is moved the pre-determined distance from the septum. The platform may be moved by applying pressure to the platform. Moving the platform the pre-determined distance may shift the protrusion out of the well.

The well may be a relatively deep well. Pressure applied to the platform may press the protrusion against a guide. The guide may direct the protrusion into a shallow well. When in the shallow well, the platform may allow fluid expelled by compressing the bladder to reenter the bladder. Deflation of the balloon may exert pressure that pushes fluid out of the balloon into the bladder.

The second distance may be equal to the first distance. The second distance may be greater than the first distance. The second distance may be less than the first distance.

Tubing may include an inflexible portion. The inflexible portion may extend along a first segment of the first lumen. In some embodiments the first segment of the first lumen may correspond to a segment of the first lumen that passes through the second lumen.

The first lumen may include a flexible portion. The flexible portion may extend along a second segment of the first lumen. The second segment of the first lumen may include a segment of the first lumen between the balloon and a junction of the first lumen and the conduit.

The flexible portion of the tubing may include a flared end. The flared end may be configured to be anastomized to the conduit. For example, when the conduit is a blood vessel, the flared end may be sutured, stapled or hooked onto the blood vessel.

The clamp may be biased to compress the flexible portion of the tubing. Compressing the flexible portion of the tubing may prevent fluid flowing through the conduit from entering the first lumen. Compressing the flexible portion of the tubing may allow fluid to flow through the conduit unimpeded by the first lumen.

Inflating the balloon may overcome the biasing force applied to the clamp. Overcoming the biasing force may open the first lumen to fluid flowing through the conduit. Deflating the balloon may allow the clamp to fluidly seal the first lumen from the conduit.

In some embodiments the clamp may be biased in an open position. The balloon may be positioned around an outside of the clamp. In such embodiments, inflating the balloon may close the clamp and deflating the balloon may allow the clamp to open.

The clamp may include a first rotatable arm. The clamp may include a second rotatable arm. The first and second rotatable arms may be configured to rotate about a pivot.

The first rotatable arm may be inserted into a sleeve. The sleeve may maintain a position of the clamp relative to a junction of the tubing and the conduit. The sleeve may prevent the clamp from shifting out of position when the conduit shifts. The sleeve may prevent a twisting of the clamp about a longitudinal axis of the first lumen.

For example, the transport system may be implanted in a human body. Locomotion of the body may shift a position of the conduit with respect to the tubing. The sleeve may ensure that the clamp is positioned to seal the flexible portion of the tubing despite shifting of the conduit.

The sleeve may be a first sleeve. In some embodiments, a second rotatable arm of the clamp may be inserted into a second sleeve. The first sleeve may maintain a position of the first rotatable arm relative to the junction. The second sleeve may maintain a position of the second rotatable arm relative to the junction.

The sleeves may be formed at least in part, by a portion of the tubing. The sleeves may be formed from solid non-thrombogenic plastic or any suitable materials. Exemplary suitable materials may include Dacron, Gore-Tex, polytetrafluoroethylene ("PTFE"), fluoropolymer products and any material suitable for implantation in a human body.

Apparatus may include, and methods may involve, a graft. The graft may be attached to a conduit. The conduit may be an artery or a vein or a carrier or any suitable medium. The graft may include tubing configured to be anastomized to the conduit. The tubing may include a compressible portion. The tubing may include a non-compressible portion. The compressible portion may be located between the conduit and the non-compressible portion of the tubing.

The graft may include a clamp. The clamp may be rotatable about a pivot. The pivot may be fused to the tubing. The clamp may be biased to crimp the compressible portion of the tubing. The clamp may be positioned to crimp the compressible portion of the tubing flush with an inner lumen of the blood vessel.

The graft may include a sleeve that positions the clamp to crimp the compressible portion of the tubing flush with an inner lumen of the blood vessel. The graft may include a sleeve. The sleeve may include three walls. The sleeve may be open on a fourth side to receive an arm of the clamp. The three sides of the sleeve may be formed from an outer wall of the tubing, material extending substantially parallel to the outer wall of the tubing and material extending substantially perpendicular to the outer wall of the tubing. When an angular anastomosis is deployed, the third wall may be formed from material that is substantially parallel to a longitudinal axis of the conduit.

In some embodiments the clamp may include two or more rotatable arms. In some embodiments, the graft may include two or more sleeves to hold two or more arms of the clamp.

For example, the graft may include a second sleeve constructed from the outer wall of the tubing, second material extending substantially parallel to the outer wall and second material extending substantially perpendicular to the outer wall of the tubing.

Closing the clamp on the compressible portion of the tubing may crimp the tubing. Crimping the tubing may result in a collapse of a lumen of the tubing. Collapsing the lumen of the tubing may prevent fluid from exiting or entering the tubing.

The graft may include a balloon. The balloon may be positioned inside the clamp. The balloon may be positioned about the non-compressible portion of the tubing.

The balloon, when inflated about the non-compressible portion of the tubing, may rotate the clamp about the pivot, opening the clamp and releasing the clamp from the compressible portion of the tubing. Upon being released from the clamp, the compressible tubing may return to an expanded state forming a lumen within the tubing. After expanding, the lumen may receive or transmit fluid.

The graft may include an elastic band that biases the clamp to crimp the compressible portion of the tubing. The elastic band may encircle first and second rotatable arms of the clamp. The elastic band may be an O-ring. The clamp may be biased using any suitable biasing member. For example, the clamp may be biased with a clip having a "memory" for a certain shape. The clip may be constructed from plastic or metal any suitable material. For example, the clip may be constructed from Nitinol, a memory shape alloy.

The tubing may be a first tubing. The graft may include a second tubing. The second tubing may include inflatable material encircling the first tubing. The inflatable material may be the balloon. In some embodiments, the inflatable material may be crimped to seal fluid within the second tubing. In some embodiments, a plug may encircle the first tubing and seal fluid within the second tubing.

Sealing the fluid within the second tubing may force the balloon to inflate in response to pressurizing the second tubing. The second tubing may be pressurized by the moveable platform compressing a bladder in the reservoir. Compressing the bladder may expel fluid from the bladder into the second tubing.

The plug may include a flange. The flange may be circular. The flange may be configured to mate with a corresponding indent in the clamp. The mating of the flange and the indent may fix a position of the clamp relative to the blood vessel. The mating of the flange and the indent may fix a position of the clamp along a longitudinal axis of the tubing. The mating of the flange and the indent may fix a position of clamp about the longitudinal axis of the tubing.

Methods may include accessing a blood vessel via a graft anastomized to the blood vessel. The method may include inserting a needle through a septum of a subcutaneous reservoir. The methods may include expanding a first chamber of the subcutaneous reservoir by pressing the needle against a moveable platform. The moveable platform may fluidly seal the first chamber from a second chamber of the reservoir.

The methods may include generating hydraulic pressure by compressing the moveable platform against a liquid-filled bladder housed within the second chamber. Using the hydraulic pressure, the methods may include opening a clamp. The clamp may be biased to compress a resilient segment of tubing anastomized to the blood vessel. Compressing the resilient segment of the tubing may collapse a lumen of the tubing. When the clamp is opened, the resilient segment of the tubing may expand, reopening the collapsed lumen.

The methods may include directing blood, via the resilient segment of tubing, from the blood vessel to the first chamber of the reservoir. Methods may include extracting the blood from the first chamber. The blood may be extracted using the needle inserted through the septum into the first chamber.

The graft may be a first graft. The subcutaneous reservoir may be a first subcutaneous reservoir. The methods may include transferring blood extracted from the first subcutaneous reservoir to a dialysis machine and filtering the blood. The filtered blood may then be transferred to a second subcutaneous reservoir. The methods may include reintroducing the filtered blood to circulation via a second graft.

The first graft may be anastomized to an artery. The first graft may be anastomized to a vein. The second graft may be anastomized to a vein. The second graft may be anastomized to an artery. In some embodiments, a plurality of grafts may be implanted. Each of the plurality of grafts may be anastomized to one or more blood vessels.

Methods may include locking the moveable platform at a distance from the septum. The locking the moveable platform may maintain a threshold level of hydraulic pressure. The threshold level of hydraulic pressure may keep the balloon inflated and the clamp open.

Pressure may be applied to the needle to press the needle against the moveable platform to unlock the moveable platform. Unlocking the moveable platform may allow a biasing member inside the reservoir to collapse the first chamber of the subcutaneous reservoir. Collapsing the first chamber may allow the bladder to inflate, thereby reducing the hydraulic pressure transmitted to the balloon. The loss of hydraulic pressure may deflate the balloon allowing the biasing member of the clamp to close the clamp upon the resilient segment of tubing and seal the blood vessel from the graft.

The method may include positioning the clamp so that outer walls of the resilient tubing are sealed flush with each other. Sealing the resilient tubing in this manner may allow the blood vessel to maintain a uniform or substantially uniform blood flow through the blood vessel across the anastomization site after the closing of the clamp. The uniform blood flow may correspond to a native blood flow through the vessel.

In yet another embodiment of a subcutaneous vascular access device, there are basically three preferred elements a needle receptor, a device lumen, and lumen clamping means. The needle receptor is subcutaneously located while portions of the clamping means lies deeper; the device lumen is the physical connection between the subcutaneous portions of the device and the deeper portion of the device, it also provides fluid communication between the needle receptor and a native body lumen. Similarly, the portions of the lumen clamping means that are meant to be actuated by hand (preferably with two fingers) are subcutaneous, while the portion contacting the device lumen are arranged to be deeper, such that the orientation provides an effective seal without creating any clotting or turbulent flow potential. This improved sealing method is targeted to reduce neointimal hyperplasia and stenosis formation commonly associated with aberrant vascular geometry caused by non-uniform device lumens or device protrusions which cause turbulent blood flow. Many anastomotic devices do not create a uniform surface at the area they serve to seal, thus creating pockets of stagnant blood, or eddies in the blood flow path or contiguous with the blood stream.

The needle receptor will optimally be palpable and located just beneath the skin surface. At the distal tapering aspect of each needle receptor is basically funnel shaped geometry, and In one embodiment, there will be a ball-valve mechanism, where the act of physically inserting the dialysis needle into, and through, the funnel will supply the required force to open the ball-valve mechanism and simultaneously allow the dialysis needle to pass through the funnel and into the blood lumen. In another embodiment, the needle receptor provides a funnel shaped geometry, having an elastic sealing material at or near narrowed end of the funnel. The elastic sealing material is configured to serve as a sealing ring. The sealing material is provided with an opening through which a displaceable sealing rod would be inserted to block unwanted flow through the opening. Upon insertion of the needle through the funnel shaped needle receptor, and through the opening of the sealing material, the advancing needle displaces the sealing rod, for example, either compressing the rod axially, or urging the rod against a compressible material, such where the sealing rod is supported by a spring, or spring loaded member, and upon the rod being displaced by the needle, as it is advanced, compresses the spring or collapsible rod. With the needle in place within the needle receptor, the clamp on the lumen may be opened to allow fluid flow through the lumen, and dialysis (or other procedure) may be performed so long as the needle remains in place. Upon the needle being removed from the funnel shaped element of the needle receptor, the sealing rod will be urged, such as by the compressed spring, and again be directed through the opening in the sealing material vacated by the withdrawn needle. In this manner, as the needle is removed from the funnel, the sealing rod fills the opening and fluid flow will be blocked from entering or exiting through the funnel. Thus, in the event of needle removal, prior to the clamp on the lumen being shut, the sealing rod will be urged back to the initial position and fill the opening left by the needle in the sealing material. The rod thus serves as safety seal to prevent undesirable free flow of fluid out from the lumen in the event of premature needle withdrawal.

For the various embodiments described herein, optimally, there will be multiple locations for directing a needle into the needle receptor, at distinct positions. For example, providing two needle entry points, may allow the access to be sequenced through each, in order to promote skin healing between being accessed.

In an embodiment, the blood lumen at the needle entry site will be rigid but penetrable, so as to maintain good patency and resilience to deformation. As the needle is advanced, the opening is increased enough to allow for the needle but not for blood leakage. When the needle (e.g., a dialysis needle) is removed the ball-valve mechanism will rotate back into a closed position sealing the blood lumen from the cylindrical portion of the funnel. The blood lumen will optimally have an almost spherical cross section configuration so that blood cannot settle into any corner For the various embodiments described herein, the clamp is optimally located where the anastomosis between the device lumen and native vessel is located. The clamp runs substantially parallel to the long axis of the native vessel in the form of two rod-like members that flank the distal most aspect of the device lumen, optimally at a position immediately above the anastomosis with the native vessel (for the sake of this description, the distal end of the device lumen and the anastomosis site may be considered one and the same when discussing the clamping location form and function). The rods will be connected to one another, at one end, such that in the closed position, they compress the distal end of the device lumen preventing blood from entering and stagnating in the device lumen. The clamp is further designed to minimize the blood exposure to the device's blood lumen to optimize for nearly laminar blood flow in the native lumen when the clamp is closed and the device is not in use. When the clamp is opened, blood will enter the device lumen through the anastomosis. The clamp is opened using the force generated by the fluid driven member of the device, or alternatively by mechanical linkages transmitting forces applied to palpable elements placed subcutaneously, as will be discussed.

In an embodiment relying on hydraulic fluid for transmitting forces, this fluid driven member is noted by a fluid filled tube in close proximity to the device lumen, a gear mechanism (or other force transfer mechanism), a plunger and optimally a safety mechanism. Just beneath the skin surface, in an embodiment, there is a palpable section with two semicircular halves. When both halves are depressed simultaneously, attached gear ring(s) will interact with corresponding cylindrical gears. As the gears rotate they rotate a screw like plunger within the hydraulic tube. The inner lining of the hydraulic tube, in which the screw plunger resides, is also threaded. When the screw plunger is rotated clockwise it moves forward and vice versa. As the plunger moves forward, it will create the hydraulic pressure that engages a second plunger to drive a wedge like member which serves to open the "clamp" section of the device.

In an embodiment relying on mechanical linkages for transmitting forces, there are provided on the device implanted subcutaneously, one or more tabs that are palpable through the skin, and configured to be manipulated by the user by applying pressure to the one or more tabs. The movement of the one or more tabs, are configured to actuate via mechanical linkages, preferably levers, the clamp to open the lumen for fluid flow therethrough. Additionally, the mechanical linkages are configured to cause movement of at least a portion of the needle receptor, thereby applying a compressive force to the elastic sealing material, whereupon the sealing material will be squeezed tightly against the outside surface of the needle. The movement of the clamp and the movement of the needle receptor may be proportional or indirectly proportional to the movement of the one or more tabs. Through mechanical linkages, such as those depicted in the various embodiments contained herein, the movement of the one or more tabs will effect a movement of a clamp puller, which in turn pulls a tension element attached to the clamp elements, thereby causing the clamp to open. The linear movement of the clamp puller is greater than the linear movement of the one or more tabs; while the linear movement of the needle receptor portion against the sealing material will be less than the linear movement of the one or more tabs. The linear movement of the needle receptor portion against the sealing material is preferably less than that of the tab movement, as a result of the creation of mechanical advantage, to apply a greater compressive force over a shorter travel, using techniques known to those skilled in the art. In this manner, the device is configured to apply a compressive force to the sealing material, creating mechanical advantage in order to apply a compressive force, as is known to those skilled in the art, where the force will be able to deform the sealing material in order to create the seal. For this embodiment of the device having mechanical linkages to effectuate clamp actuation and compression of the sealing material, it is contemplated that the linear movement of the tabs will be in the range of 1-5 millimeters, preferably in the range of 2-4 millimeters, and more preferably 2-3 millimeters. From this tab movement, it is anticipated that the linear action of the clamp puller to open the clamp will be at least 150%, at least 200%, or at least 300% of the movement of the tabs; while the movement of the needle receptor will be in the range of less than 50%, less than 30%, or less than 20% of the movement of the tabs.

In an embodiment, there are optimally additional rings attached to the semicircles that engage a "pen click" mechanism along the cylinder with the force used to open the clamp, thereby allowing continual blood flow through the device lumen. To close the clamp, the operator presses the semicircles again, releasing the "pen click" mechanism, allowing the clamp to close. The retraction of the semicircles rotates the gears in the hydraulic generator section of the device unscrewing the screw plunger backward and reducing the hydraulic force exerted on the second distal plunger. The clamp and wedge assembly will force the second plunger backward thereby sealing the anastomosis.

In the various embodiments described herein, there may be a safety mechanism on the device to prevent the clamp from being inadvertently opened. In one embodiment, the safety mechanism is comprised of a subcutaneous button which retracts a pin when compressed. The pin runs parallel within a conduit contained within the wall of the device lumen, or other convenient location. The pin prevents the semicircle gear ring from rotating around the blood lumen cylinder when not retracted. When the subcutaneous safety button is compressed, it retracts the pin completely into the wall of the blood lumen cylinder allowing the gear ring to rotate. In order to open the device clamps, the operator has to press and hold the safety button and then compress the semicircles.

In another embodiment, the safety mechanism comprises a subcutaneously located, palpable button, and similar to the previously described "pen click" mechanism, the palpable button may be manipulated to alternate between a first state and a second state. While in a first state, the palpable button prevents movement of the one or more tabs, thereby preventing the clamp sealing the lumen from opening; and while in a second state, the palpable button frees the one or more tabs for actuation, such that the clamp can be opened. Preferably, the palpable button, in a first state, serves to prevent substantially all movement of the subcutaneous tabs, until such a point as the button has been depressed. Once the palpable button is depressed, and is in the second state, the one or more tabs may then be pressed to cause the clamp to open and the palpable button, while in the second state is further arranged to maintain the one or more tabs in the actuated position, and thereby ensures the clamp remains in an open state, until such a point in time at which the palpable button is depressed again, and caused to revert to the first state, whereupon multiple actions occur: the one or more tabs are released, causing the clamp on the lumen to be closed by spring tension as the clamp puller returns to its original location; the funnel portion moves away from the sealing material, and halts the compression upon the sealing material, thereby releasing the seal grasping the needle in the funnel is released, whereupon the needle may be withdrawn.

In the use of this embodiment of the device, it is contemplated that the operator will direct a hollow needle to penetrate the skin, and subcutaneously enter the wide mouth end of the funnel shaped element of the needle receptor. As the needle is advanced deeper into the needle receptor, it advances through an opening in a sealing material positioned at or near a narrowed portion of the funnel of the needle receptor. As the needle is advanced through the opening in the sealing material, it displaces a sealing rod that is aligned coaxially with the axis of the needle receptor. The needle is arranged along an axis that extends through the center of the funnel and extends tangentially to a spherical chamber within the device. The spherical chamber is in fluid communication with a lumen extending distally towards the anastomosis junction. The needle is advanced along the axis until the distal tip of the needle is in fluid communication with the interior of the spherical chamber. In an embodiment, the needle is advanced to the location where the distal tip of the needle located tangential to or is aligned with a tangential opening into the interior of the spherical chamber. At this point, the palpable button of the safety mechanism may be depressed. With the palpable button depressed, in a manner similar to a "pen click", the safety mechanism will now allow the user to manipulate at least one tab, preferably two tabs, by applying a pressure and causing movement of the tab. The movement of the one or more tabs will cause the action of mechanical linkages, which result in the actuation of the clamp adjacent to the anastomosis junction to open, and also cause at least a portion of the funnel of the needle receptor to move in a distal direction, whereupon compressive force is applied the sealing material. The sealing material is thus squeezed between the housing of the device and the funnel, and in response, the sealing material constricts the opening through which the needle is directed, thereby sealing tightly around the outside surface of the needle, and thereby preventing fluid flow around the periphery of the needle. The movement of the one or more tabs is restrained by the safety mechanism, allowing the user to release the pressure of the tabs, and have the tabs retain their actuated position. In this manner, the clamp is maintained open, allowing fluid flow through the lumen, and maintaining the seal around the needle.

In use of the embodiment of the device having the tab actuated clamps, it is contemplated that two or more of these devices may be placed for dialysis. In this instance, it is anticipated that dialysis would occur where each device is implanted and anastomosed to a blood vessel, where first device is in fluid communication with the needle that serves to withdraw blood, typically from the arterial system, from the patient for the dialysis procedure, and the second device is in fluid communication with the needle that is returning dialyzed or filtered blood to the patient, typically into the venous system. Upon completion of the dialysis treatment, the fluid line for each device would be flushed with an amount of saline, or any other suitable flushing liquid to clear the line. After flushing, the palpable button of the safety mechanism may then be depressed, thereby returning the tabs to their original state and sealing the lumen by closing the clamp at the anastomosis junction, and further releasing seal of the sealing material around the periphery of the needle, such that the needle may then be withdrawn. As the needle is withdrawn from the needle receptor, the sealing rod, which had been displaced by the advancing needle, will return to its original position within the sealing material, thereby preventing fluid transfer in or out through the funnel of the needle receptor.

In the event that the needle is removed from the patient during dialysis, the sealing rod would be urged proximally into the opening in the sealing material left by the removal of the needle, thereby preventing the free flow of fluid through the device. This is especially important where the lumen is anastomosed to the arterial system, as the blood pressure is higher than in the venous system, and would if left unchecked, potentially cause significant blood loss to the patient. Thus the embodiment of the device featuring a sealing rod provides an automatic safety seal to prevent unchecked flow through the device in the event that the needle is removed while the clamp remains in an open position, and there is fluid communication between the needle receptor and the blood vessel.

In another embodiment, the subcutaneous vascular access device, comprises a needle receptor, a lumen (which may be referred to as a device lumen, in order to distinguish the element from a native bodily lumen), a lumen clamping means, and a clamp manipulator (In certain orientations, the clamp manipulator may be referred to as a component of the lumen clamping means, which is just for ease of illustration). In these types of embodiments said needle receptor is arranged to accept a needle having a distal tip that is inserted from outside the body, and to provide positioning means for the placement of said needle.

In an embodiment, the lumen is arranged to contact said needle receptor at a first location and with said lumen being arranged to be anastomosed to a native body lumen at a second location. The lumen is further designed to have a cross section that remains nearly circular, but other shapes may be utilized so long as no geometric feature provides an eddy or other stagnate region, as this may lead to clotting or other cascades of difficulties. Similarly, irregularities in the vessel wall that cause turbulent or otherwise irregular flow will cause a different set of problems; all of which will decrease the efficiency of the device, render it unusable, or harm the patient in a worst case situation.

For the various embodiments described herein, The lumen clamping means generally comprises at least two clamping members. These members are optimally arranged to compress said lumen at a location between said first location and said second location, in an orientation substantially parallel to said lumen. It is believed that a parallel orientation is optimal, however, it is contemplated that lumen characteristics (including anastomosis design and characteristics) and fluid mechanics may dictate that a slight offset from parallel may provide a better seal with optimal flow characteristics. Therefore, a range of clamp orientations are contemplated in this disclosure. The goal of this element is primarily to provide a seal along said anastomosis and prohibit fluid flow therethrough, while maintaining an even flow of blood or other fluid through the native body lumen.

The shape of the clamping members may be generally circular in cross-section, to provide a linear region of highest clamping stress; however, lumen design and materials may dictate that a square or rectangular cross-section may provide an optimum sealing profile. Therefore, these and various contacting shapes are within the contemplation of this disclosure.

In an embodiment relying on hydraulic operation, a fluid driven member, or other suitable member arranged to transfer the forces applied, may be utilized to be energized and cause diametrically opposed motion of the said at least two clamping members thereby decompressing said lumen to provide fluid communication between said native body lumen and said first location. The fluid used herein, may be a liquid or a gas, however, the noncompressibility of a liquid may provide a rapid and repeatable response.

In another embodiment, a clamp manipulator, also referred to as a clamp manipulator or manipulation means, may be used. In an embodiment, the clamp manipulator may comprise elements that actuate mechanical linkages which directly drive the opening of clamp, and actuate a sealing mechanism around a needle, as has been previously discussed. For example, the action of the clamp manipulator may occur as one or more tabs are pressed by the user, the tabs through mechanical linkages convert the movement to a linear movement of a clamp puller, which is connected by a tension element to the clamping members, which react by opening and unsealing the lumen to allow fluid flow therethrough. In an embodiment, the clamp members are spring held by spring tension in a closed position, unless the clamp puller is retracted with a force to overcome the spring tension. Additionally, the one or more tabs when pressed, are urged against a spring, such that upon release, the spring tension pushes the tabs back to their original state, and reversing the movements caused by the action of the one or more tabs. In another embodiment, the clamp manipulator may comprise at least one tab rotatably attached to at least one axial support member, wherein the depressing of said tab causes rotation which may serve to engage a gear assembly which is arranged to pressurize a fluid to drive said fluid driven member.

In various embodiments described herein, the aforementioned clamp manipulator may further comprise at least a second tab. For the embodiment having hydraulic operation, the second tab may be rotatably attached to a second axial support member. For the embodiment relying on mechanical linkages to actuate the clamp, the second tab is preferably arranged to operate in concert with the first tab, such that the tabs may be squeezed towards each other, and the movement of each tabs are coupled together to reduce the force that each tab would have to exert alone to perform the tasks of opening the clamp, and tightly sealing around the needle, as has been described previously. Regardless, of whether a single or dual tab assembly is used, the tab or tabs are arranged to allow two fingers to provide adequate force to effect the required actions, such as clamp opening and sealing. It is contemplated that for a multiple tab assembly, each tab may be arranged to operate independently, or alternatively perform dissimilar actions. For example, a first tab may be configured to actuate the clamp, and the second tab may actuate the sealing around the needle. The clamp manipulator may further comprise locking means, wherein said locking means secures said tab(s) at a predetermined amount of travel. Additionally, a preferred embodiment locking means is arranged to unlock following the application of additional pressure to said tab(s) while they are in the secured state. This tab, or arrangement of tabs, are preferably palpable from outside the body.

In an embodiment, the needle receptor, and more precisely, the positioning means, may include a rotating member. This rotating member may also include an angular protrusion arranged to slidably accept the distal tip of said needle, wherein said angular protrusion moves upon the application of force from said needle which causes rotation of said rotating member. The rotating member may also contain a channel arranged to accept said needle following the alignment of said channel with said needle which was caused by the rotation of said rotating member. Once the rotating member is turned far enough by the needle tip, the channel becomes proud, and then such needle slides into the channel. The needle will complete the alignment with the channel as it begins to slide in. In a preferred embodiment, the needle fits tightly against the channel, causing a seal to be formed between the needle and the channel. Once the needle is lodged in said channel, the needle and the channel are in fluid communication with said device lumen. To better assess needle placement, meaning the situs of the initial needle stick from outside the body, the needle receptor is preferred to be palpable from outside the body.

The rotating member may be further arranged to have resistance to rotation, whereupon said rotating member provides return rotation force during needle insertion; wherein said return rotation force serves to grip said needle and prevents migration of the distal tip of said needle during a procedure. This return force may also aid in creating and holding the seal between the needle and the channel. These various embodiments containing needle receptors, further comprise a plurality of needle receptors, with said receptors being located longitudinally along said lumen such that said needle may be introduced at a plurality of locations.

In yet another embodiment of a subcutaneous vascular access device, there are basically four preferred elements a device lumen, a needle receptor, lumen clamping means, and a clamp manipulator. In this embodiment the device lumen has a distal end and a proximal end defining a lumen length. The device lumen may also have an anastomosis at said distal end, wherein said anastomosis serves to connect said device lumen to a native body lumen.

A needle receptor may be arranged to be palpable from outside the body and anchored along the lumen length to provide fluid communication therewith; further, the needle receptor may have a rotating member arranged within its base. The rotating member may, among other things serve to adjustably constrain the flow of fluid from said device lumen into said needle receptor.

The rotating member may accomplish this preferred action through the incorporation of an angular protrusion arranged to slidably accept the distal tip of a needle, wherein said angular protrusion moves upon the application of force from said needle which causes rotation of said rotating member. Additionally, a channel may be arranged to accept said needle following the alignment of said channel with said needle upon the appropriate amount of rotation of said rotating member, whereupon said needle and said channel become aligned and thus are in fluid communication with said lumen. The entry needle may be assisted or guided, in this embodiment, by a funnel shaped entry port arranged to accept and guide said needle toward said rotating member. Further, the funnel shaped entry port may be palpable, so that the needle stick in the skin may be more exact.

A preferred embodiment will also contain a lumen clamping means arranged at the proximal end of said device lumen. This lumen clamping means may include a manipulation means comprising two tabs each rotatably attached to a main axis member. Further, a pressure translation assembly comprising gearing means may be arranged to couple with said manipulation means upon the rotation of said tabs. This gearing means may consist of at least one external-tooth ring-gear rotatably attached to the outer circumference of the device lumen. In a preferred embodiment, the device contains two such ring-gears; with each separately coupled to one of two tabs. The coupling could be maintained by a ratcheting type of mechanism, or other gear transition mechanism known to those skilled in the art. This embodiment may also benefit from two follower-rings, which could be similarly rotatably attached to the outer circumference of the device lumen. These rings may be located at the opposite end of the tab, away from the ring-gear, in order to provide support or lateral stability to the tab (especially during use). The follower-rings are preferred to be smooth on the inner and outer surfaces, in order to allow free rotation.

In an embodiment the gear-rings are each coupled to a slave gear; since the gear-rings are attached to the tabs (which travel in opposite directions) the two slave gears travel in opposite directions, and therefore they will mesh. These slave gears act in concert to add the cumulative power generated by the tabs. The tangential tab rotation may be translated into longitudinal movement through the use of a fluid driven member. The fluid driven member may be arranged to be driven by one of the slave gears. An alternate embodiment may further utilize a longitudinal screw gear coupled with said gearing means.

In an embodiment, the fluid driven member may be preferably constructed with a fluid housing tube arranged to contain a pressurized fluid, having a first end and a second end. A plunger arranged within said first end of said fluid housing tube may be further arranged to receive said longitudinal screw gear or a plunger drive by said slave gear affixed thereto. In this embodiment, the plunger serves to modulate pressure in the fluid housing tube.

The fluid driven member may be oriented longitudinally with the main axis of the device lumen, and serve to translate power in that direction. A wedge member is preferably slidably arranged at said second end of said fluid housing tube, wherein the wedge member moves distally with increasing fluid pressure.

In the various embodiments described herein, at least two clamping members arranged to rest in tension on opposing sides of said device lumen. In the embodiment using hydraulic forces, the clamping members are further arranged to receive said wedge member such that said wedge serves to translate the longitudinal movement imparted by said pressurized fluid into lateral forces. These lateral forces operate to separate said at least two clamping members, with such separation allowing the device lumen to gain fluid communication with said native body lumen. The clamping members may be arranged with an angular receptor, concave in nature and formed by one member on each clamp being angularly oriented with the device lumen's longitudinal axis.

Apparatus and methods described herein are illustrative. Apparatus and methods of the invention may involve some or all of the features of the illustrative apparatus and/or some or all of the steps of the illustrative methods. The steps of the methods may be performed in an order other than the order shown and described herein. Some embodiments may omit steps shown and described in connection with the illustrative methods. Some embodiments may include steps that are not shown and described in connection with the illustrative methods.

Illustrative embodiments of apparatus and methods in accordance with the principles of the invention will now be described with reference to the accompanying drawings, which form a part hereof. The drawings show illustrative features of apparatus and methods in accordance with the principles of the invention. The features are illustrated in the context of selected embodiments. It will be understood that features shown in connection with one of the embodiments may be practiced in accordance with the principles of the invention along with features shown in connection with another of the embodiments.

The apparatus and methods of the invention will be described in connection with exemplary embodiments. It is to be understood that other embodiments may be utilized and structural, functional and procedural modifications may be made without departing from the scope and spirit of the present invention.

FIG. 1 shows illustrative therapeutic scenario 100.

Scenario 100 shows limb 105. Limb 105 includes vein 103 and artery 101. Scenario 100 shows access port 107. Port 107 is affixed to artery 101. Port 107 may be affixed to any suitable blood vessel, such as vein 103. Port 107 may be affixed to artery 101 using a surgical technique. The surgical technique may include anastomosis and arteriotomy/venotomy. The anastomosis may be an end-to-end straight anastomosis. The anastomosis may include an end-to-end angled anastomosis. The anastomosis may include a side to end or side to side anastomosis. The angled anastomosis may be "bulbous." An angled anastomosis may maintain laminar flow and reduce turbulence of blood flowing through blood vessel 101 or 103. Any suitable techniques may be used to affix port 107 to a blood vessel 103 or 101.

Port 107 is coupled via tubing 111 to reservoir 109. Tubing 111 may allow access to "deep" blood vessels. Reservoir 109 may be affixed to limb 105 subcutaneously. Reservoir 109 may be configured to receive one of feeds 113. Feeds 113 draw blood from a blood vessel. Feeds 113 may terminate in a needle or any other suitable connection to reservoir 109. For example, the feeds may terminate in a 14-gauge needle. Feeds 113 transfer blood to dialysis machine 115. Feeds 113 transfer blood extracted from blood vessel 101 to dialysis machine 115. Dialysis machine 115 may filter the blood extracted from blood vessel 101. Dialysis machine 115 may return filtered blood to blood vessel 103 via feeds 113.

In some embodiments, a system including reservoir 109, tubing 111 and port 107 may be affixed to vein 103. Reservoir 109 may receive filtered blood from dialysis machine 115 via feeds 113. The filtered blood may be pumped through reservoir 109, through tubing 111 and returned to circulation in blood vessel 103 through port 107.

One or more components of reservoir 109 may seal tubing 111 and port 107. Sealing tubing 111 and port 107 may not allow blood to flow from blood vessel 101 into port 107 or tubing 111. Reservoir 109 may be configured to sequentially seal tubing 111 prior to or after sealing port 107.

Figure 2:
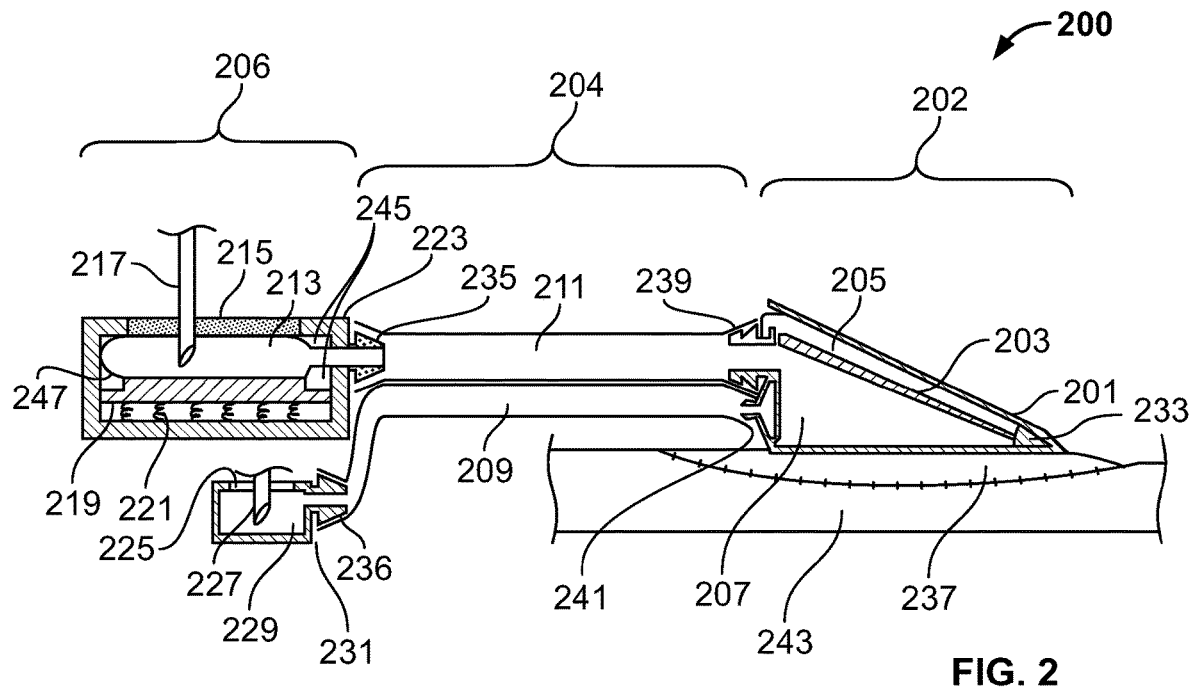
FIG. 2 shows illustrative apparatus in accordance with principles of the invention.

FIG. 2 shows illustrative apparatus 200. Apparatus 200 may include port 202. Port 202 may include one or more of the features of port 107 (shown in FIG. 1). Port 202 may be in fluid connection with tubing 204. Tubing 204 may include one or more features of tubing 111 (shown in FIG. 1). Tubing 204 may be in fluid connection with reservoir 206. Reservoir 206 may include one or more reservoirs such as reservoir 223 and reservoir 231. Reservoir 206 may include one or more features of reservoir 109 (shown in FIG. 1).

Port 202 may include housing 201. Housing 201 may be constructed from solid non-thrombogenic plastic or any suitable materials. Exemplary suitable materials may include Dacron, Gore-Tex, polytetrafluoroethylene ("PTFE"), fluoropolymer products and any material suitable for implantation in a human body. Suitable material may include material approved by a government agency, such as the United States Food and Drug Administration, for use in a human body.

Port 202 may include swing-arm 203. Swing-arm 203 may be constructed from and/or coated with Dacron, Gore-Tex, PTFE, fluoropolymer products or any suitable material. Swing-arm 203 may rotate about hinge 233. Hinge 233 may be constructed from a pliable Dacron, Gore-Tex, PTFE, fluoropolymer products or any suitable material. Swing-arm 203 may be configured to rotate about hinge 233 and allow blood to flow between blood vessel 243 and housing 201. Blood may flow from blood vessel 243 into housing 201. Blood may flow from housing 201 into blood vessel 243. Swing-arm 203 may be configured to rotate about hinge 233 and impede and/or cut-off blood flow between blood vessel 243 and housing 201.

Swing-arm 203 may be configured to rotate about hinge 233 in response in an increase in pressure inside chamber 205. Chamber 205 may be any suitable shape. Chamber 205 may be circular, square or triangular. Chamber 205 may be in fluid connection with lumen 209. Lumen 209 may be in fluid connection with chamber 229.

Needle 227 may inject a medium into chamber 229. The medium may preferable be a liquid, such as a saline solution. The medium may include any suitable liquid or gas. Adapter 236 prevents a leakage of medium flowing between lumen 209 and chamber 229. Adapter 241 prevents a leakage of the medium flowing between lumen 209 and chamber 205. Adapters 236 or 241 may be any suitable adapter. For example, an adapter may hermetically seal lumen 209 and chamber 229. The adapter may include a threaded screw.

Injecting the medium into chamber 229 may force the medium through lumen 209 and into chamber 205. Forcing the medium into chamber 205 may increase a pressure inside chamber 205. The increased pressure inside chamber 205 may cause swing-arm 203 to rotate about hinge 233. Rotation of swing-arm 203 about hinge 233 may "push" swing-arm 203 toward blood vessel 243. Pressure in chamber 205 and rotation of swing-arm 203 about hinge 233 may result in swing-arm 203 sealing housing 201 from blood flowing through blood vessel 243.

Needle 227 may inject the medium until a threshold pressure inside lumen 205 is obtained. Needle 227 may include a pressure gauge (not shown). The threshold pressure may correspond to a degree of rotation of swing-arm 203 about hinge 233. The threshold pressure may correspond to a positioning of swing-arm 203 about hinge 233 such that swing-arm 203 is substantially parallel to blood vessel 243. The threshold pressure may correspond to a positioning of swing-arm 203 about hinge 233 such that blood does not flow into housing 201.

Reservoir 231 includes membrane 225. Membrane 225 may be a self-sealing membrane. Needle 227 may inject the medium into reservoir 231 by penetrating self-sealing membrane 225. After a registering of a threshold pressure, needle 227 may be withdrawn through self-sealing membrane 225. Self-sealing membrane may prevent any medium leakage after withdrawal of needle 227. Self-sealing membrane 225 may maintain the threshold pressure until a portion of the medium is extracted from chamber 229.

Needle 227 may extract a portion of the medium from chamber 229. Extracting a portion of the medium may adjust the threshold pressure. Extracting a portion of the medium may adjust pressure on swing-arm 203. Extracting the portion of the medium may reduce the threshold pressure imposed on swing-arm 203. Extracting the portion of the medium may impose a negative pressure on swing-arm 203. The negative pressure may result in swing-arm 203 rotating about hinge 233. Rotation of swing-arm 203 may contract chamber 205.

Extracting the portion of the medium may open housing 201 to blood flowing within blood vessel 243. Extracting at least a portion of the medium from reservoir may result in swing-arm 203 rotating about hinge 233. The rotation of swing-arm 203 about hinge 233 may unseal an orifice between housing 201 and blood vessel 243. Rotation of swing-arm 203 about hinge 233 may allow blood to flow from blood vessel 243 into housing 201. The blood may flow from blood vessel 243 into passageway 207. A pressure exerted on blood within blood vessel 243 may force the blood into lumen passageway 207. The pressure may be arterial blood pressure. Blood within passageway 207 may flow into lumen 211. Adapter 239 may join passageway 207 and lumen 211. Adapter 239 may prevent leakage of blood flowing between passageway 207 and lumen 211.

Reservoir 223 includes chamber 213. Reservoir 223 includes membrane 215. Membrane 215 may be a self-sealing membrane. Chamber 213 may be expanded or contracted by movement of platform 219. Platform 219 may be rigid. Platform 219 may be biased relative to self-sealing membrane 215 by springs 221. Platform 219 may be biased using any suitable pressure exerting member. A pressure exerting member may include elastic membranes and springs. Platform 219 may be biased to contract chamber 213. Platform 219 may be biased to exert pressure on self-sealing membrane 215.

Needle 217 may penetrate self-sealing membrane 215. Needle 217 may be in fluid connection with feeds 113 (shown in FIG. 1). Needle 217 may push platform 219 away from self-sealing membrane 215. Movement of platform 219 away from self-sealing membrane 215 may expand chamber 213. Expanding chamber 213 may allow blood to flow from lumen 211 into chamber 213. Lumen 211 may be joined to reservoir 223 by adapter 235. Adapter 235 may provide a leak-proof connection between chamber 213 and lumen 211. Adapter 235 may provide a hermetical connection between chamber 213 and lumen 211.

Needle 217 may extract blood from chamber 213. Blood extracted from chamber 213 may be transferred to dialysis machine 115 (shown in FIG. 1). Blood extracted from chamber 213 may be filtered by dialysis machine 115.

Needle 217 may inject blood into chamber 213. Blood injected into chamber 213 may be reintroduced into circulation by travelling through lumen 211, through passageway 207 and into blood vessel 243.

Chamber 213 may include internal walls 247 and 245. Walls 247 and 245 may be flexible. Walls 247 and 245 may be constructed from Dacron, Gore-Tex, PTFE, fluoropolymer products or any other suitable material. Walls 247 and 245 may allow for expansion and/or contraction of chamber 213. Walls 247 and 245 may prevent blood from leaking out of chamber 213.

When needle 217 is removed from self-sealing membrane 215, springs 221 may exert pressure on platform 219. The pressure may "push" platform 219 toward membrane 215. Movement of platform 219 may purge blood or any other medium present in chamber 213.

Following a purging of chamber 213, lumen 211 may be sealed. Lumen 211 may be sealed by injecting a medium into chamber 229. Injection of the medium may increase pressure inside lumen 209. The increased pressure may result in a diameter of lumen 209 expanding. Expansion of lumen 209 may decrease a diameter of lumen 211. Expansion of lumen 209 may seal lumen 211. Lumen 209 may be configured to expand faster proximal to reservoir 223 and more slowly proximal to housing 201. Bending resistances of tubing 204 may vary longitudinally along lumen 209. The different expansion rates may "squeeze" any residual medium present in lumen 211 into passageway 207.

Apparatus 200 may be configured to allow for a full expansion of lumen 209 and corresponding sealing of lumen 211 prior to a sealing of passageway 207. Sequential sealing may allow any residual medium present in lumen 211 to be "squeezed" through lumen 211 and through passageway 207 before sealing passageway 207. Continuous injection of medium into chamber 229 may seal lumen 211 and passageway 207. Completion of the sealing of lumen 211 and passageway 207 may correspond to a registering of a threshold pressure inside chamber 229.

In some embodiments, tubing 204 may be fused to reservoir 206. Fusing tubing 204 and reservoir 206 may allow residual medium to be "squeezed" out of a juncture between tubing 204 and reservoir 206. Some embodiments may not include tubing 204. For example, reservoir 206 may be fused directly to port 202.

Figure 3A:
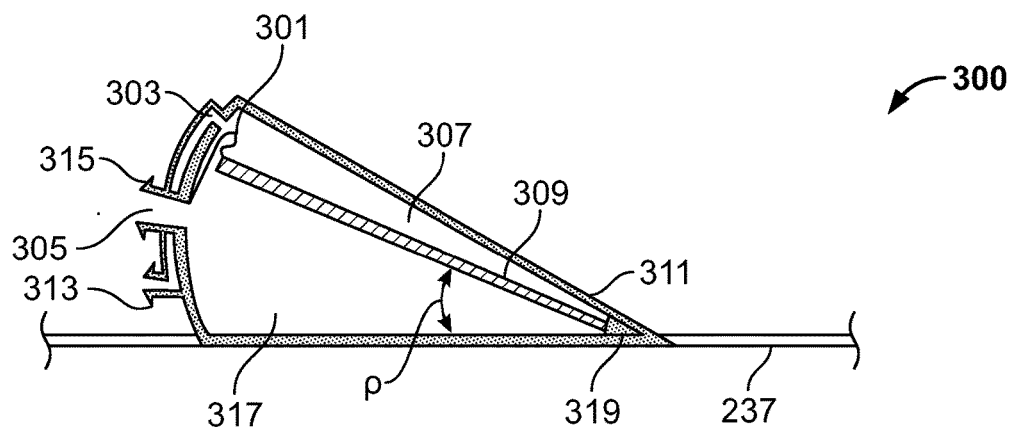
FIG. 3A shows illustrative apparatus in accordance with principles of the invention.

Components of apparatus 200 may be sized (i.e., length, width, diameter, circumference, area) to achieve a blood flow that will allow completion of a dialysis procedure within a target time period. FIG. 3A shows illustrative port 300. Port 300 may include one or more features of port 107 (shown in FIG. 1) or port 202 (shown in FIG. 2). Port 300 may be joined to a blood vessel via patch 237. Patch 237 may be constructed from Dacron, Gore-Tex, PTFE, fluoropolymer products or any other suitable material. Patch 237 may include excess material. The excess material may be "trimmed" by a surgeon or other practitioner allowing for tailored positioning of patch 237. Patch 237 may be affixed to a blood vessel such as artery 101, vein 103 (shown in FIG. 1) or blood vessel 243 (shown in FIG. 2). Patch 237 may be affixed to a blood vessel by anastomosis and arteriotomy or any other suitable technique. The anastomosis may include an end-to-end angled anastomosis. The anastomosis may include a side to end or side to side anastomosis.

Port 300 may include housing 311. Port 300 may include chamber 307. Port 300 may include passageway 317. Port 300 may include sealing member 309. Sealing member 309 may be rigid.

Port 300 may include flexible sealing portion 301. Flexible sealing portion 301 may be constructed from Dacron, Gore-Tex, PTFE, fluoropolymer products or any other suitable material. Flexible sealing portion 301 may be affixed to a first end of sealing member 309.

A second end of sealing member 309 may be affixed to hinge 319. Injecting a medium into chamber 307 may expand chamber 307. Chamber 307 may expand by rotating sealing member 309 through variable angle ρ. Pressure within chamber 307 may position sealing member 309 by rotation through angle ρ. Pressure within chamber 307 may position sealing member 309 substantially parallel to patch 237. Expansion of chamber 307 may position flexible sealing portion 301 substantially perpendicular to sealing member 309.

When sealing member 309 is positioned substantially parallel to patch 237, blood may be prevented from flowing between patch 237 and orifice 305. Positioning sealing member 309 substantially perpendicular to sealing portion 301 may obstruct passageway 317. Positioning sealing portion 301 substantially perpendicular to sealing member 309 may prevent a flow through orifice 305. Sealing portion 301 may prevent a flow between passageway 317 and a tubing connection joined to adapter 315. The tubing connection may include any suitable tubing such as tubing 111 (shown in FIG. 1) or tubing 204 (shown in FIG. 2).

Orifice 305 may be directly coupled to a reservoir, such as reservoir 206 (shown in FIG. 2). Adapter 315 may be directly coupled to a reservoir, such as reservoir 206 (shown in FIG. 2). Channel 303 may be directly coupled to a reservoir such as a reservoir 206. One or more components of port 300 or port 202 (shown in FIG. 2) may be directly coupled to one or more components a reservoir such as reservoir 206 (shown in FIG. 2) or reservoir 109 (shown in FIG. 1).

Injecting a medium into chamber 307 may position sealing member 309 substantially parallel to patch 237. In a preferred embodiment, the medium may be a liquid. The medium may be a gas or any suitable medium. The medium may be injected into chamber 307 via channel 303.

Figure 3B:
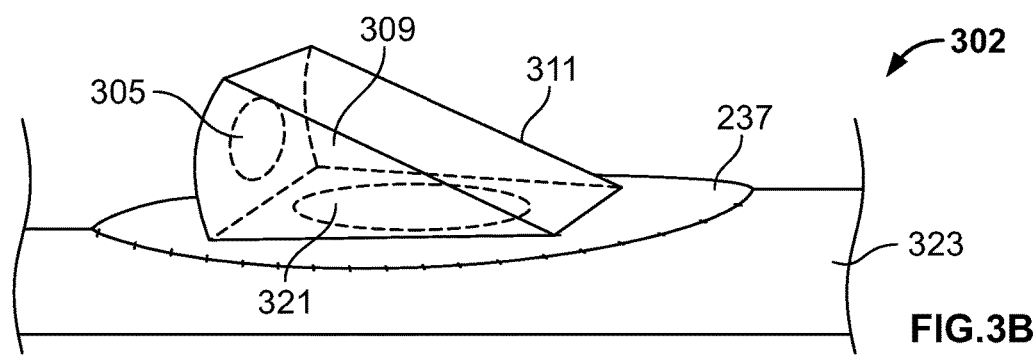
FIG. 3B shows illustrative apparatus in accordance with principles of the invention.

FIG. 3B shows illustrative port 302. Port 302 may include one or more features of port 300 (shown in FIG. 3A), port 202 (shown in FIG. 2) or port 107 (shown in FIG. 1). Port 302 may include orifice 321. Orifice 321 may allow blood travelling in blood vessel 323 to enter port 302. Orifice 321 may allow blood in port 302 to flow into blood vessel 323. Blood vessel 323 may be an artery. Blood vessel 323 may be a vein. Blood vessel 323 may be any suitable lumen of a circulatory system.

Orifice 321 may be sealed by swing-arm 203 (shown in FIG. 2) or sealing member 309 (shown in FIG. 3A). Sealing of orifice 321 may prevent blood or any other medium from flowing through orifice 321. Orifice 321 may be sealed following completion of a dialysis procedure.

Port 302 includes orifice 305 (also shown in FIG. 3A). Orifice 305 may allow blood to flow between a tubing and passageway 321. The tubing may include any suitable tubing such as tubing 111 (shown in FIG. 1) or tubing 204 (shown in FIG. 2). Orifice 305 may be sealed by sealing portion 301 (shown in FIG. 3A). Sealing orifice 305 may prevent a flow of blood through orifice 305. Orifice 305 may be sealed following completion of a dialysis procedure. Port 302 may be configured to seal orifice 305 prior to sealing orifice 321.

Figure 4:
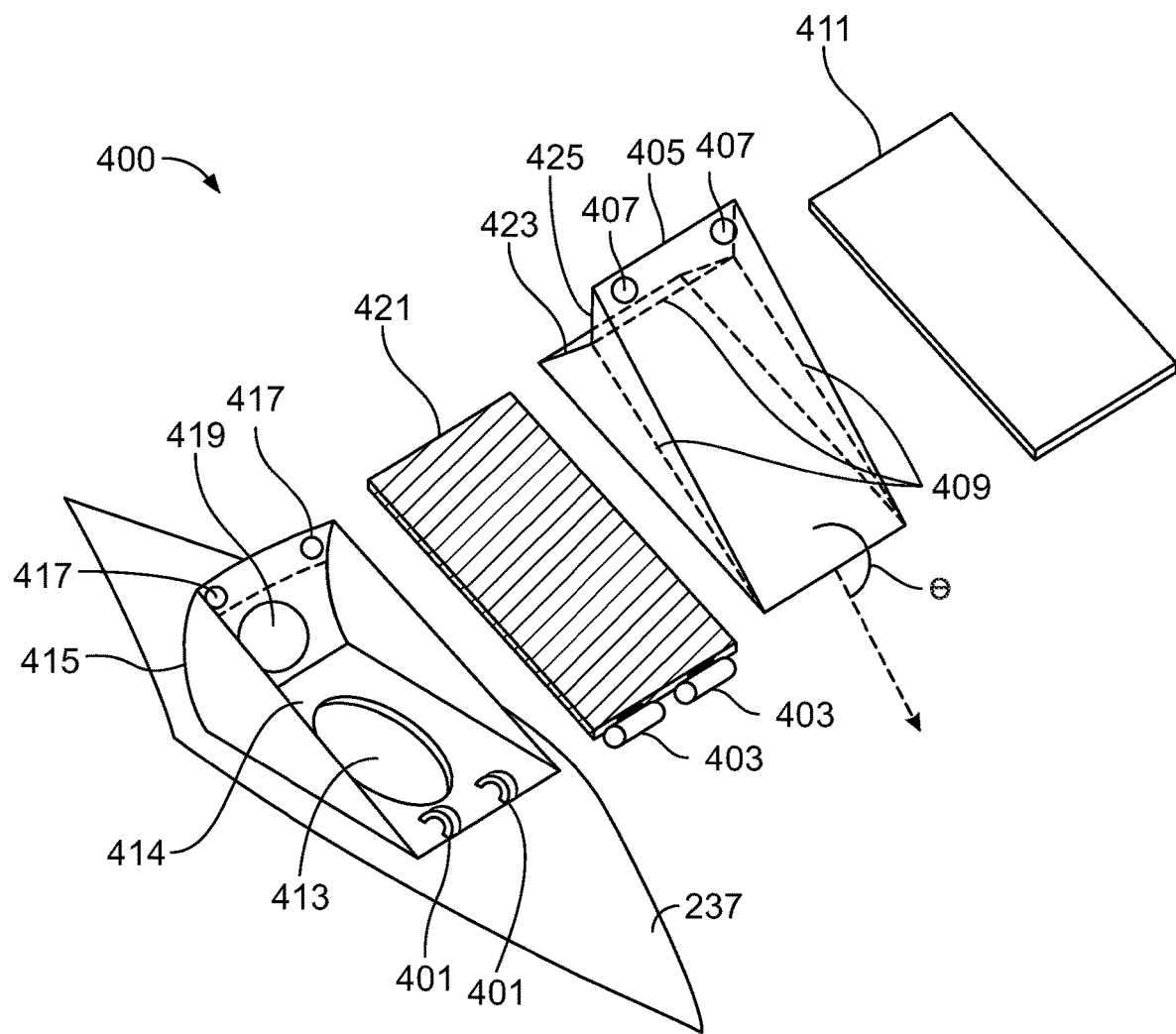
FIG. 4 shows illustrative apparatus in accordance with principles of the invention.

FIG. 4 shows illustrative port components 400. Port components 400 may include one or more features of port 300 (shown in FIG. 3A), port 302 (shown in FIG. 3B), port 202 (shown in FIG. 2) or port 107 (shown in FIG. 1). Port components 400 include housing 415. Housing 415 may be affixed to a blood vessel via patch 237. Housing 415 includes orifices 413 and 419. Blood may flow from orifice 419 to orifice 413. Blood may flow from orifice 413 to orifice 419. Blood may flow through passageway 414. Orifices 413 and 419 may be sized to allow for an optimal rate of blood flow.

For example, orifice 413 may be larger in area than orifice 419. Orifice 413 may be sized proportionally to patch 237. Orifices 413 and 419 may be sized to complete a dialysis procedure within a target time period.

Port components 400 may include sealing member 421. Sealing member 421 may include one or more features of swing-arm 203 (shown in FIG. 2) or sealing member 309 (shown in FIG. 3A). Sealing member 421 may be configured to seal orifice 413. Sealing orifice 413 may prevent a flow of blood through orifice 413. Sealing member 421 may be rigid.

Sealing member 421 may include one or more tenons 403. Tenons 403 may be seated in mortise 401. Tenons 403 may rotate in mortise 401. Tenons 403 and mortise 401 may form a flexible joint. The flexible joint may include one or more features of hinge 319 (shown in FIG. 3A) or hinge 233 (shown in FIG. 2).

Port components 400 include balloon 405. Balloon 405 may be inflated. Balloon 405 may be inflated by injecting a medium through orifices 407. Balloon 405 may be deflated. Balloon 405 may be deflated by extracting the medium via orifices 407. Balloon 405 may include one or more features of chamber 307 (shown in FIG. 3A) or chamber 203 (shown in FIG. 2).

Balloon 405 may be configured to expand and/or contract about angle θ. When balloon 405 is deflated, balloon 405 may be configured to fold along creases 409. Balloon 405 may be affixed to sealing member 421. Expansion and/or contraction of balloon 405 may position sealing member 421 relative to orifice 413.

Balloon 405, when inflated, may position sealing member 421 over orifice 413. Balloon 405 may apply pressure to sealing member 421 to create a leak-proof seal over orifice 413. When positioned over orifice 421, sealing member 421 may prevent blood flow through passageway 414. Balloon 405 may be inflated to a pre-determined pressure. The pre-determined pressure may correspond to a position of sealing member 421 relative to orifice 413.

Balloon 405 may include panel 423. Balloon 405 may include panel 425. Balloon 405 may seal orifice 419. Inflating balloon 405 may seal orifice 419. Balloon 405 may include one or more features of sealing portion 301 (shown in FIG. 3A). The pre-determined pressure may correspond to a position of panels 423 and 425 relative to orifice 419. The pre-determined pressure may correspond to panels 423 and 425 being positioned substantially parallel to orifice 419.

Housing 415 may include orifices 417. Orifices 417 may be aligned with orifices 407 of balloon 405. Inflating balloon 405 may include injecting a medium though orifices 417, through orifices 407 and into balloon 405. Deflating balloon 405 may include extracting the medium from balloon 405 via orifices 407 and 417.

In some embodiments, a top of panel 425 may be affixed to housing 415 below orifices 417. Housing roof 411 may form a top of balloon 405. Medium flowing through orifices 417 may "spill" into balloon 405 expanding balloon 405.

Port components 400 include housing roof 411. Balloon 405 may be affixed to housing roof 411. Housing roof 411 may remain stationary relative to movement of sealing member 421. Housing roof 411 may remain stationary relative to inflation/deflation of balloon 405. Deflating balloon 405 may generate a negative pressure inside balloon 405. The negative pressure may move sealing member 421 relative to housing roof 411. Negative pressure inside balloon 405 may move sealing member 421 relative to orifice 413.

Housing roof 411 may include biasing members (not shown). The biasing members may include elastic membranes, springs or any suitable biasing member. The biasing members may include one or more feature of biasing members 221 (shown in FIG. 2). The biasing members may be positioned between housing roof 411 and sealing member 421. The biasing members may penetrate balloon 405. The biasing members may be encapsulated within balloon 405. The biasing members may bias sealing member 421 relative to housing roof 411.

The bias may correspond to attraction between sealing member 421 and housing roof 411. The bias may correspond to repulsion between sealing member 421 and housing roof 411. The biasing members may pull sealing member 421 away from orifice 413 during a deflation of balloon 405. The biasing members may pull sealing member 421 toward orifice 413 during inflation of balloon 405.

Figure 5A:
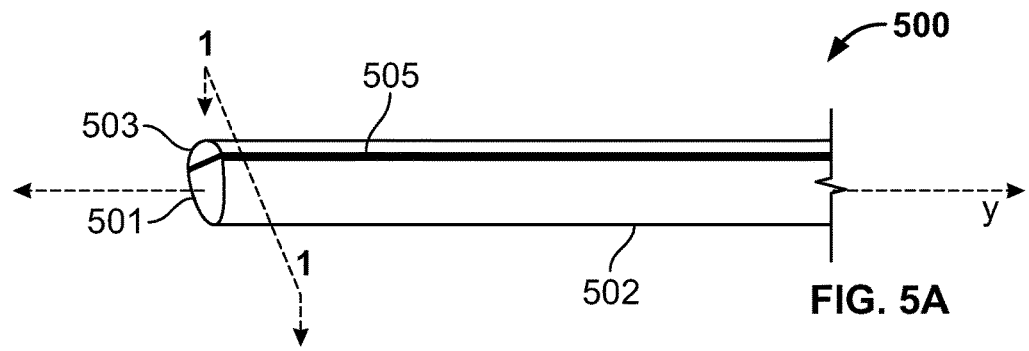
FIG. 5A shows illustrative apparatus in accordance with principles of the invention.

FIG. 5A shows illustrative tubing 500. Tubing 500 may include one or more features of tubing 204 (shown in FIG. 2) or tubing 111 (shown in FIG. 1). Tubing 500 may be affixed to a blood vessel via an angled bulbous anastomosis and arteriotomy. Via the angled bulbous anastomosis and arteriotomy, tubing 500 may be affixed a blood vessel such as an artery or vein without a port such as port 300 (shown in FIG. 3A), port 202 (shown in FIG. 2) or port 107 (shown in FIG. 1). In a preferred embodiment, tubing 500 is coupled to a port such as port 300 (shown in FIG. 3A), port 202 (shown in FIG. 2) or port 107 (shown in FIG. 1)

Tubing 500 includes sheath 502. Tubing 500 includes baffle 505. Tubing 500 includes lumen 501. Tubing 500 includes lumen 503. Baffle 505 may separate lumen 501 and lumen 503. Lumen 503 may transport a medium for inflating/deflating balloon 405 (shown in FIG. 4). Lumen 503 may carry a medium for increasing pressure in chamber 205 (shown in FIG. 2) or chamber 307 (shown in FIG. 3A). Lumen 503 may transport blood between a blood vessel and reservoir 213 (shown in FIG. 2). Lumen 501 may include one or more features of lumen 503.

In a preferred embodiment, a blood transporting lumen of tubing 500 is oriented superiorly with respect to an outer body surface or integumentary tissue. A superiorly oriented lumen may allow access to the blood carrying lumen. Access may be needed to clear a thrombosis or other obstruction in the blood carrying lumen.

Baffle 505 may be configured to stretch. Baffle 505 may be configured to bend. Baffle 505 may be configured to obstruct lumen 501 and/or lumen 503. Baffle 505 may impermeably obstruct lumen 501 or lumen 503. For example, a medium may be injected into lumen 501 via needle 227 (shown in FIG. 2). The medium may enter lumen 501 and fill chamber 307 (shown in FIG. 3A). The filling of chamber 307 may increase pressure on at least a portion of sheath 502 and baffle 505. Baffle 505 may be elastic.

Sheath 502 may be inelastic relative to baffle 505. In response to the increased pressure, baffle 505 may bulge into lumen 503. Baffle 505 may bulge and obstruct a flow through lumen 503. Pressure inside lumen 501 may be increased until baffle 505 bulges and impermeably seals lumen 503.

Baffle 505 may bend at different rates along a length of sheath 502. Different bending properties along the length of sheath 502 may result in baffle 505 "pushing" blood or other medium in lumen 503 along the length of sheath 502. For example, a first length of baffle 505 along axis Y may be configured to bulge when subject to a pressure of P1. A second length of baffle 505 along axis Y may be configured to bulge when the pressure corresponds to P2. P1 and P2 may be any suitable values of pressure. In a preferred embodiment P2 is greater than P1. Baffle 505 may be associated with any suitable pressure gradient along axis Y.

Figure 5B:
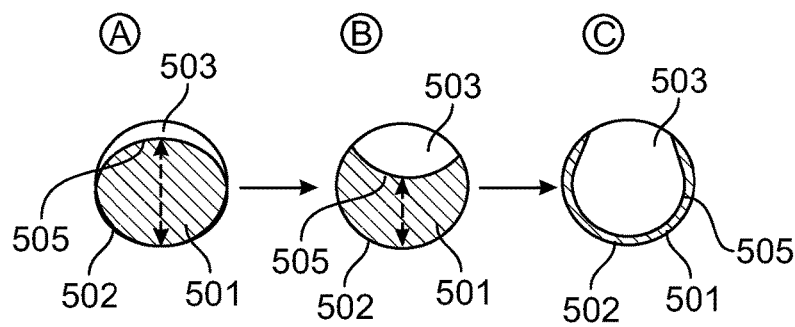
FIG. 5B shows illustrative apparatus in accordance with principles of the invention.

FIG. 5B shows a sectional view of an illustrative expansion of lumen 503 and corresponding sealing of lumen 501. At point A, a diameter of lumen 501 may be at a maximum. At point A, a diameter of lumen 503 may be at a minimum. When the diameter of lumen 501 is at a maximum, lumen 501 may be configured to transport a target flow. The target flow may correspond to a flow of blood from a blood vessel to dialysis machine 115 (shown in FIG. 1).

At point B, a medium may be injected into lumen 503. Injection of the medium may increase pressure inside lumen 503. The increased pressure inside lumen 503 may result in baffle 505 bulging into lumen 501. The bulging of baffle 505 into lumen 501 may obstruct a flow through lumen 501. Baffle 505 may be configured to adjust a flow rate through lumen 501.

At point C, continuous injection of the medium into lumen 503 has "stretched" baffle 505 across lumen 501 and against sheath 502. The pressure of baffle 505 pressing against sheath 502 may impede a flow through lumen 501. The pressure of baffle 505 pressing against sheath 502 may create an impermeable seal that prevents a flow through lumen 501.

Figure 5C:
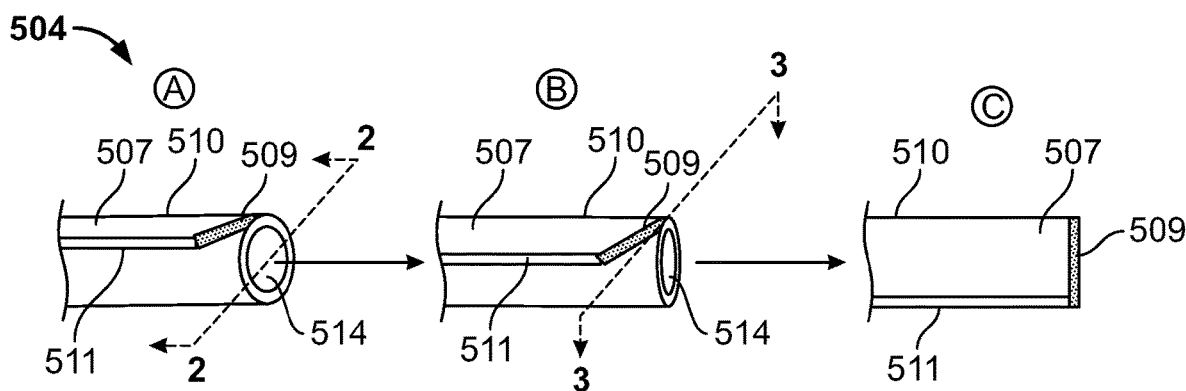
FIG. 5C shows illustrative apparatus in accordance with principles of the invention.

FIG. 5C shows illustrative tubing 504. Tubing 504 may include one or more features of tubing 111 (shown in FIG. 1), tubing 204 (shown in FIG. 2) or tubing 500 (shown in FIG. 5A). Tubing 504 may terminate in an angled bulbous anastomosis and arteriotomy. Via the angled bulbous anastomosis and arteriotomy, tubing 500 may be directly affixed a blood vessel such as an artery or vein.

Tubing 504 includes sheath 510. Tubing 504 includes lumen 507. Lumen 507 may be open at a first end of tubing 504. Lumen 507 may be closed at a second end of tubing 504. Tubing 504 includes lumen 514. Tubing includes inner lining 511. Tubing 504 includes plug 509. Plug 509 may be rotatably connected to inner lining 511. Plug 509 may be connected to inner lining 51 using Dacron, Gore-Tex, PTFE, fluoropolymer products or any suitable material. Inner lining 511 and plug 509 may rotate, with respect to each other, about angle α.

At point A, angle α may be approximately 180°. At point A, a diameter of lumen 514 may be at a maximum. When the diameter of lumen 514 is at a maximum, lumen 514 may be configured to transport a target flow. The target flow may correspond to a flow of blood from or to a blood vessel.

At point B, a medium may be injected into lumen 507. Injection of the medium into lumen 507 may cause adjustment of angle α between inner lining 511 and plug 509. Injection of the medium into lumen 507 may decrease angle α. A decrease in angle α may correspond to an increase in a diameter of lumen 507. A decrease in angle α may correspond to a decrease in a diameter of lumen 514. A decrease in the diameter of lumen 514 may obstruct a flow through lumen 514.

At point C, angle α may be approximately 90°. At point C, plug 509 may block any flow into or through lumen 514. At point C, lumen 507 may be full of the injected medium. The injected medium may generate pressure inside lumen 507. The pressure may maintain a position of plug 509 with respect to lumen 514. The pressure may maintain a value of angle α. The pressure may maintain a value of angle α at approximately 90°.

The medium may be injected into lumen 514 using needle 227 (shown in FIG. 2). Self-sealing membrane 225 (shown in FIG. 2) may maintain the injected medium and corresponding pressure inside lumen 507.

Figure 5D:
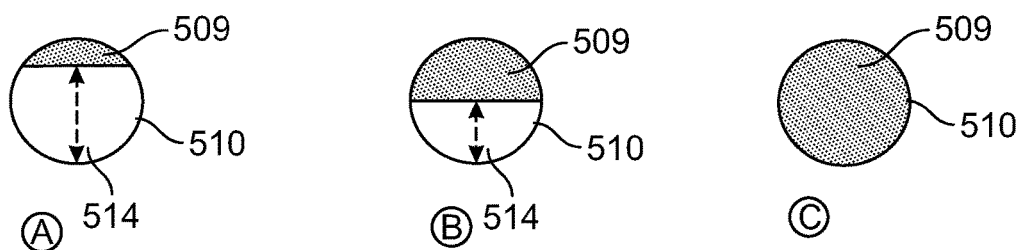
FIG. 5D shows illustrative apparatus in accordance with principles of the invention.

FIG. 5D shows illustrative views A-C of tubing 504. Each of views A-C corresponds to a change in angle α and corresponding position of plug 509 within lumen 514.

At point A, angle α is approximately 180°. At point A, a diameter of lumen 514 is at a maximum. At point B, angle α has been decreased. The decrease in angle α corresponds to a decrease in the diameter of lumen 514. The decrease in angle α corresponds to an increase in a diameter of lumen 507. Injecting a medium into lumen 507 may result in plug 509 extending into lumen 514. Injecting a medium into lumen 507 may result in plug 509 obstruction at least a portion of lumen 514. Rotation of plug 509 relative to inner lining 511 may correspond to a decrease in angle α.

At point C, plug 509 is positioned to prevent blood or any other fluid from entering lumen 514. At point C, a diameter of lumen 507 is at a maximum. Extracting the medium from lumen 507 may increase angle α, and allow a flow to enter lumen 514.

Figure 5E:
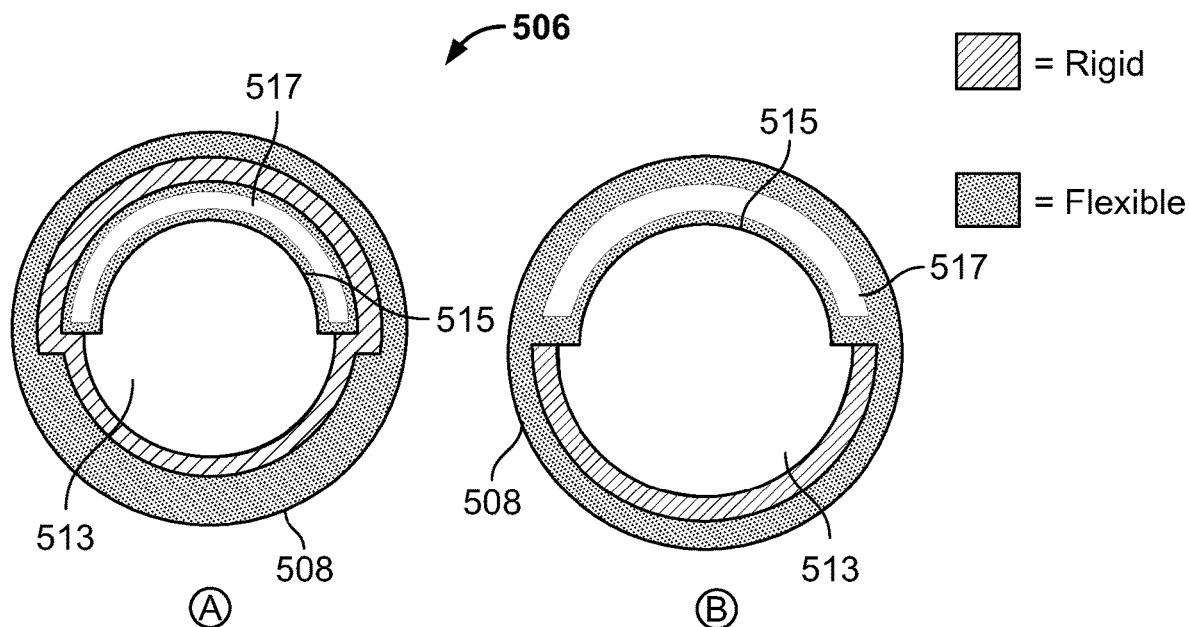
FIG. 5E shows illustrative apparatus in accordance with principles of the invention.

FIG. 5E shows illustrative views 506A and 506B of a portion of tubing 500 taken along lines 1-1 (shown in FIG. 5A). Tubing 500 (shown in FIG. 5A), tubing 204 (shown in FIG. 2) or tubing 111 (shown in FIG. 1) may include one or more features of illustrative view 506.

Illustrative view 506A shows sheath 508. Illustrative view 506A shows baffle 515. Illustrative view 506A shows lumen 513 and lumen 517. At least a portion of lumen 517 may be lined with a flexible material such as Dacron, Gore-Tex, PTFE, fluoropolymer products or any suitable material. Baffle 515 may be the portion of lumen 517 lined with the flexible material. When lumen 513 is filled with a medium, baffle 515 may expand or "bulge" into lumen 517. Expansion of baffle 515 into lumen 517 may decrease a diameter of lumen 517 and obstruct a flow through lumen 517. Baffle 515 may expand through lumen 517 and press against a rigid portion of sheath 508. The pressure of baffle 515 against sheath 508 may impermeably seal lumen 517.

In some embodiments, blood may travel through lumen 517. Lumen 517 may be oriented superiorly with respect to an outer body surface or integumentary tissue. A superiorly oriented lumen may allow access to the blood carrying lumen. Access may be needed to clear a thrombosis or other obstruction in the blood carrying lumen.

In some embodiments, lumen 517 may be filled with a medium. Baffle 515 may expand or "bulge" into lumen 513. Expansion of baffle 515 into lumen 513 may decrease a diameter of lumen 513 and obstruct a flow through lumen 513. Baffle 515 may expand through lumen 513 and press against a rigid portion of sheath 508. The pressure of baffle 515 against sheath 508 may impermeably seal lumen 513.

Illustrative views 506A and 506B show that sheath 508, lumen 517 and lumen 513 may include flexible material, rigid material or a combination of both rigid and flexible material. Rigid material may include plastics. The flexible material may include Dacron, Gore-Tex, PTFE, fluoropolymer products and any material suitable for implantation in a human body.

Figure 5F:
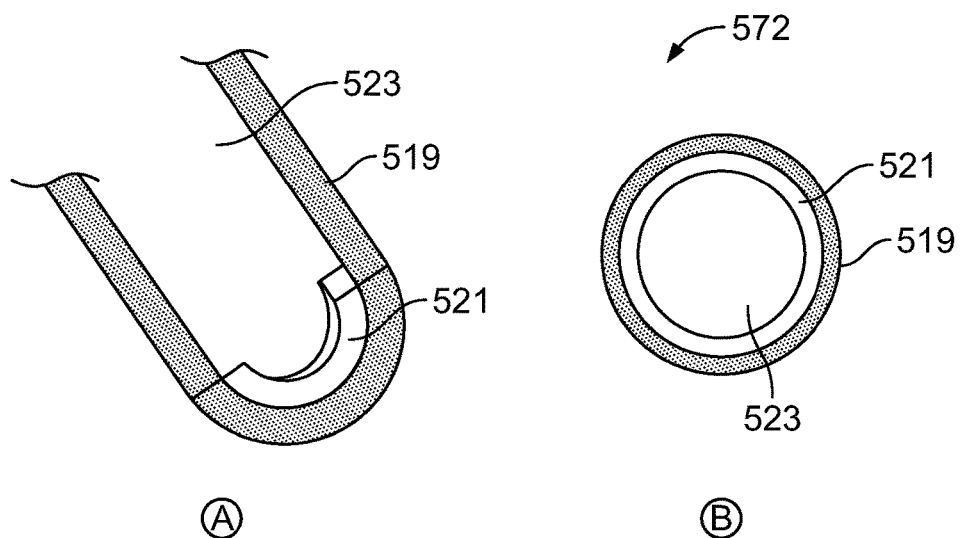
FIG. 5F shows illustrative apparatus in accordance with principles of the invention.

FIG. 5F shows illustrative views 572A and 572B. Illustrative view 572A is taken along lines 2-2 (shown in FIG. 5C). Illustrative view 572B is taken along lines 3-3 (shown in FIG. 5C).

Illustrative view 572A shows sheath 519. Illustrative view 572A shows ridge 521. Ridge 521 may be configured to provide a "catch" for a plug, such as plug 509 (shown in FIG. 5C). When angle α (shown in FIG. 5C) is approximately 90°, plug 509 may be pressed against ridge 521. Pressing plug 509 against ridge 521 may create a seal that prevents a flow from entering lumen 523. The flow may correspond to blood circulating in a blood vessel.

Illustrative view 572B shows an exemplary circular shape of ridge 521. Illustrative view 572B shows that ridge 521 may form a lining between sheath 519 and lumen 523. A plug such as plug 509 (shown in FIG. 5C) may be configured to close lumen 523 by pressing on ridge 521. Plug 509 may have a circular shape.

Plug 509 may have a diameter that is larger than the diameter of ridge 521 and smaller than a diameter of sheath 519. Plug 509 may be square shaped, triangle shaped or have any suitable shape.

Figure 5G:
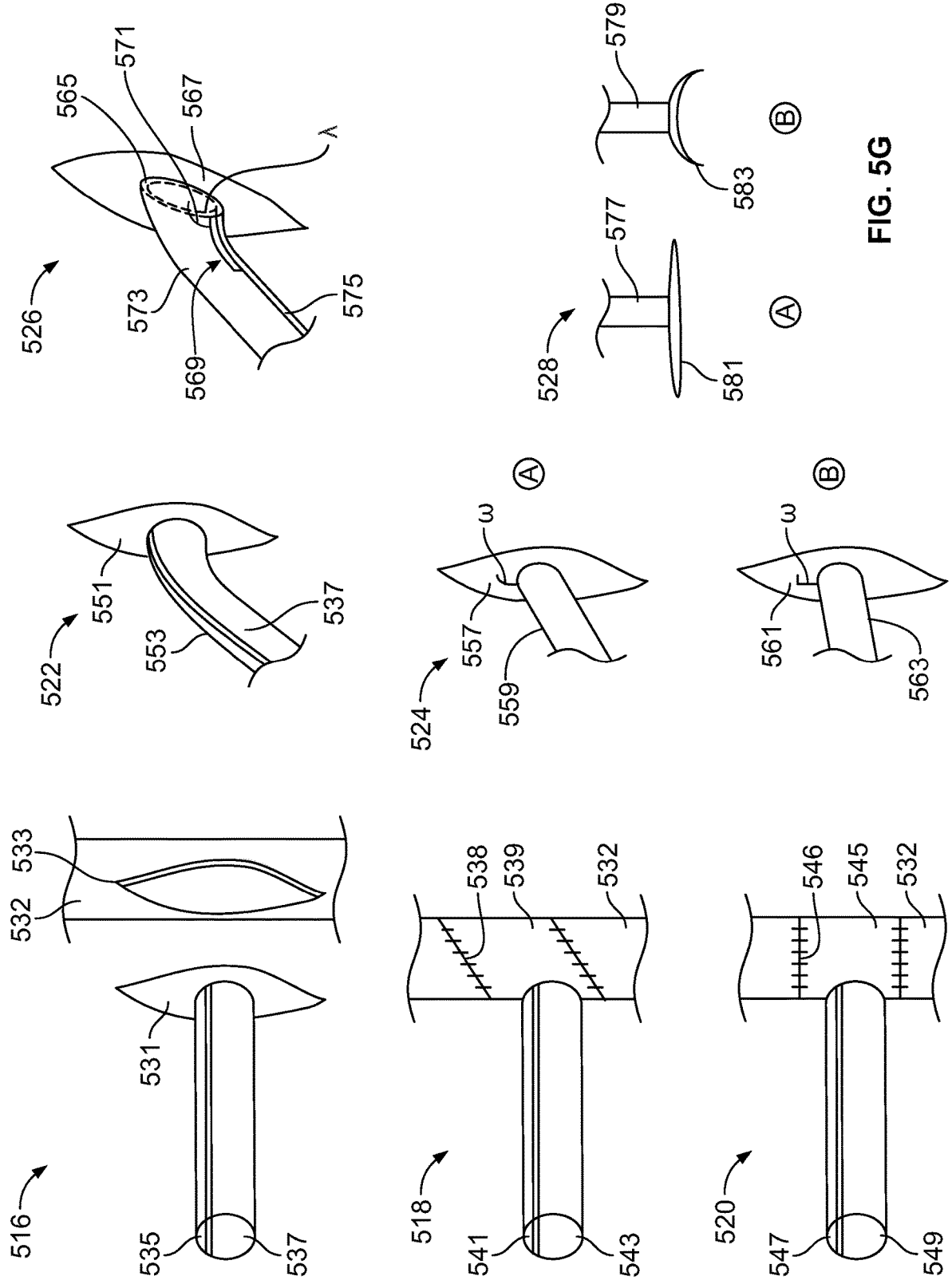
FIG. 5G shows illustrative therapeutic scenarios and associated apparatus in accordance with principles of the invention.

FIG. 5G shows illustrative tubing arrangements and therapeutic techniques 516, 518, 520, 522, 524A, 524B, 526, 528A and 528B.

Tubing arrangement 516 shows an illustrative anastomosis and arteriotomy. Tubing arrangement 516 shows lumen 537 and lumen 535. Arrangement 516 shows lumen 535 in a collapsed state and lumen 537 in an open state. Lumens 535 and 537 may be affixed to patch 531. During an anastomosis and arteriotomy/venotomy patch 531 may be sutured into surgical incision 533 in blood vessel 532. Expansion of lumen 535 may seal lumen 537, and prevent blood from flowing out of blood vessel 532 into lumen 537. Contraction of lumen 535 may allow blood to flow out of blood vessel 532 into lumen 537. Blood entering lumen 537 from blood vessel 532 may be transferred via lumen 537 to dialysis machine 115 (shown in FIG. 1). Blood filtered by dialysis machine 115 may be transferred to blood vessel 532 via lumen 537.

Arrangement 518 shows an illustrative end-to-end "angled" anastomosis. Arrangement 518 shows lumen 541 and lumen 543. Lumens 541 and 543 may be affixed to graft 539. Graft 539 may be sutured to blood vessel 532. Graft 539 may be sutured to blood vessel 532 at "angled" seam 538. Lumen 543 may include one or more feature of lumen 537. Lumen 541 may include one or more features of lumen 535.

Arrangement 520 shows an illustrative end-to-end "straight" anastomosis. Arrangement 520 shows lumen 547 and lumen 549. Lumens 547 and 549 may be affixed to graft 545. Graft 539 may be sutured to blood vessel 532. Graft 545 may be sutured to blood vessel 532 at "straight" seam 546. Lumen 547 may include one or more features of lumen 535. Lumen 549 may include one or more feature of lumen 537.

Arrangement 522 shows an illustrative angled "bulbous" anastomosis and arteriotomy. Arrangement 522 shows lumen 553 and lumen 555. Lumens 553 and 555 may be affixed to patch 551. Patch 551 may be sutured to a blood vessel such as blood vessel 532. Lumen 553 may include one or more features of lumen 535. Lumen 555 may include one or more features of lumen 537.

Arrangement 524A shows an illustrative therapeutic scenario. Arrangement 524A shows that tubing 559 may be angled with respect to patch 557. Tubing 559 may include one or more or more lumens, such as lumen 535 and/or lumen 537. When tubing 563 is angled with respect to patch 561, angle ω may be greater than 90°. Tubing 559 may include one or more features of tubing 111 (shown in FIG. 1), tubing 204 (shown in FIG. 2) tubing 500 (shown in FIG. 5A) or tubing 504 (shown in FIG. 5C).

Arrangement 524B shows another illustrative therapeutic scenario. Arrangement 524B shows that tubing 563 may be substantially perpendicular with respect to patch 561. When tubing 563 is substantially perpendicular to patch 561, angle ω may be approximately 90°. Tubing 563 may include one or more or more lumens, such as lumen 535 and/or lumen 537. Tubing 559 may include one or more features of tubing 111 (shown in FIG. 1), tubing 204 (shown in FIG. 2) tubing 500 (shown in FIG. 5A) and tubing 504 (shown in FIG. 5C).

An angle ω greater than 90° may maintain laminar blood flow within blood vessel 532. An angle ω greater than 90° may reduce turbulent blood flow within blood vessel 532.

Arrangement 526 shows an illustrative therapeutic scenario. Arrangement 526 shows tubing 573. Tubing 573 may include one or more features of tubing 500 (shown in FIG. 5A), tubing 504 (shown in FIG. 5C), tubing 204 (shown in FIG. 2) or tubing 111 (shown in FIG. 1).

Tubing 573 includes lumen 571, lumen 575, plug 569 and ridge 565. An expansion of lumen 575 may rotate plug 569 about angle A. Rotation of plug 569 about angle A may press plug 569 against ridge 565. Pressing plug 569 against ridge 565 may prevent blood from flowing through lumen 571.

Lumen 575 may be expanded by injecting a medium into lumen 575. The medium may be maintained inside lumen 575 by a reservoir. The reservoir may be any suitable reservoir such as reservoir 231 (shown in FIG. 2) or reservoir 109 (shown in FIG. 1). A pressure of plug 569 against ridge 565 may be maintained by a reservoir, such as reservoir 231.

Arrangement 528A shows an illustrative therapeutic scenario. Arrangement 528A shows tubing 577 affixed to "flat" patch 581. Flat patch 581 may be sutured to a blood vessel such as blood vessels 103 or 101 (shown in FIG. 1). After attachment to the blood vessel, tubing 577 may act as conduit to transfer blood to/from the blood vessel. Tubing 577 may include a plug such as plug 569 or a baffle such as baffle 515 (shown in FIG. 5E). The plug or baffle may be configured to seal tubing 577 and prevent a flow through tubing 577.

Arrangement 528B shows another illustrative therapeutic scenario. Arrangement 528B shows tubing 579 affixed to "curved" patch 583. Curved patch 583 may be sutured to a blood vessel such as blood vessels 103 or 101 (shown in FIG. 1). After attachment to the blood vessel, tubing 577 may act as conduit to transfer blood to/from the blood vessel. Tubing 579 may include a plug such as plug 569 or a baffle such as baffle 515 (shown in FIG. 5E). The plug or baffle may be configured to seal tubing 577 and prevent a flow through tubing 579.

Figure 6A:
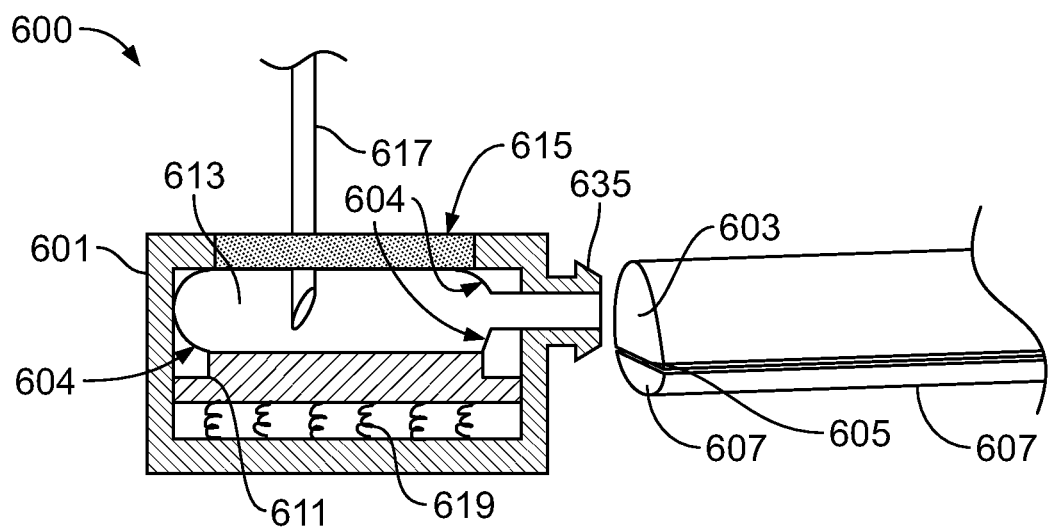
FIG. 6A shows illustrative apparatus in accordance with principles of the invention.

FIG. 6A shows illustrative apparatus 600. Apparatus 600 includes reservoir 601. Reservoir 601 may include one or more features of reservoir 223, reservoir 231 (both shown in FIG. 2) or reservoir 109 (shown in FIG. 1).

Reservoir 601 includes chamber 613. Reservoir 601 includes self-sealing membrane 615. Translation of platform 611 may expand or contract chamber 613. Platform 611 may be biased within reservoir 601 by springs 619. Platform 611 may be biased relative to self-sealing membrane 615 by springs 619. Platform 611 may be biased using any suitable pressure exerting member. Platform 611 may be biased to exert pressure on self-sealing membrane 615.

Needle 617 may penetrate self-sealing membrane 615. Needle 617 may be in fluid connection with feeds 113 (shown in FIG. 1). Inserting needle 617 into chamber 613 may separate platform 611 from self-sealing membrane 615. Pressure applied to needle 617 may condense springs 619 and translate platform 611. Translation of platform 611 away from self-sealing membrane 615 may expand chamber 613. Expanding chamber 613 may allow blood to flow from lumen 603 or 605 into chamber 613. Adapter 635 may provide a leak-proof seal between chamber 613 and lumen 603 or lumen 605.

Needle 617 may extract blood from chamber 613. Blood extracted from chamber 613 may be transferred to dialysis machine 115 (shown in FIG. 1). Blood extracted from chamber 613 may be filtered by dialysis machine 115. Blood filtered by dialysis machine 115 may be reintroduced into circulation by injecting the filtered blood into chamber 613.

Chamber 613 may include walls 604. Walls 604 may be flexible. Walls 604 may be constructed from Dacron, Gore-Tex, PTFE, fluoropolymer products or any other suitable material. Walls 604 may allow for expansion and/or contraction of chamber 613. Walls 604 may prevent blood from leaking out of chamber 613.

When needle 617 is removed from self-sealing membrane 615, springs 619 may exert pressure on platform 615. Springs 619 may "push" platform 615 toward self-sealing membrane 615. Movement of platform 615 toward self-sealing membrane may purge excess fluid from chamber 213. After a transfer of blood through chamber 613, chamber 613, tubing 607 and passageway 207 (shown in FIG. 2) may be purged of residual blood by movement of platform 611.

Figure 6B:
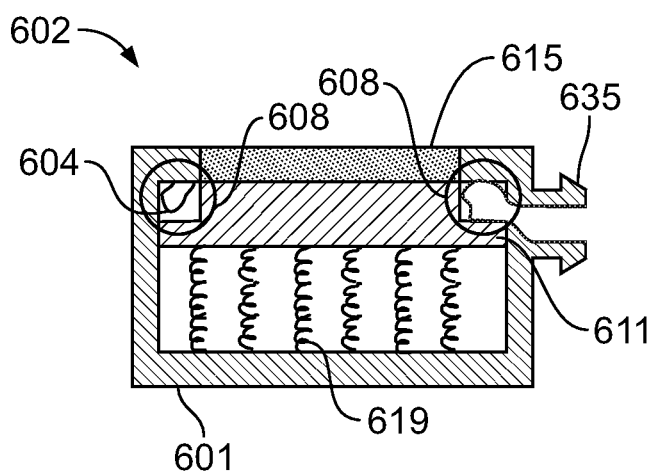
FIG. 6B shows illustrative apparatus in accordance with principles of the invention.

FIG. 6B shows illustrative scenario 602. In scenario 602, platform 611 is pressed against self-sealing membrane 615. Biasing members 619 may apply pressure to platform 611. The pressure applied by biasing members 619 may cause platform 619 to translate. The pressure applied by biasing members 619 may cause platform 619 to translate and contract chamber 613. The pressure applied by biasing members 619 may press platform 611 against self-sealing membrane 615.

Translation of platform 611 and a corresponding contraction of chamber 613 may expel medium present in chamber 613. The expulsion of medium present in chamber 613 may force the medium through tubing 607 and through passageway 207. The expulsion of the medium from chamber 613 may cleanse tubing 607 and/or passageway 207.

For example, a first end to tubing 607 may be joined to adapter 635. A second end of tubing 607 may be joined to housing 201 via adapter 239 (shown in FIG. 2). A saline solution may be introduced into chamber 613 and tubing 607. The saline solution may flush out any blood present in chamber 613, tubing 607 or housing 201.

After introducing the saline solution, needle 617 may be removed from chamber 613. Removal of needle 617 may allow platform 611 to translate toward self-sealing membrane 615. Translation of platform 611 and corresponding contraction of chamber 613 may "squeeze" the saline solution out of chamber 613, through tubing 607 and through passageway 207, thereby purging residual blood and/or saline present in chamber 613, tubing 607 and/or passageway 207 (shown in FIG. 2). The saline solution may be a heparinized solution designed to prevent blood clotting within chamber 613, tubing 607 and/or passageway 207.

When platform 611 presses against self-sealing membrane 615, walls 604 may fold into cutouts 608. When needle 617 pushes platform 611 away from self-sealing member, walls 604 may un-fold and form sides of chamber 613.

Figure 7:
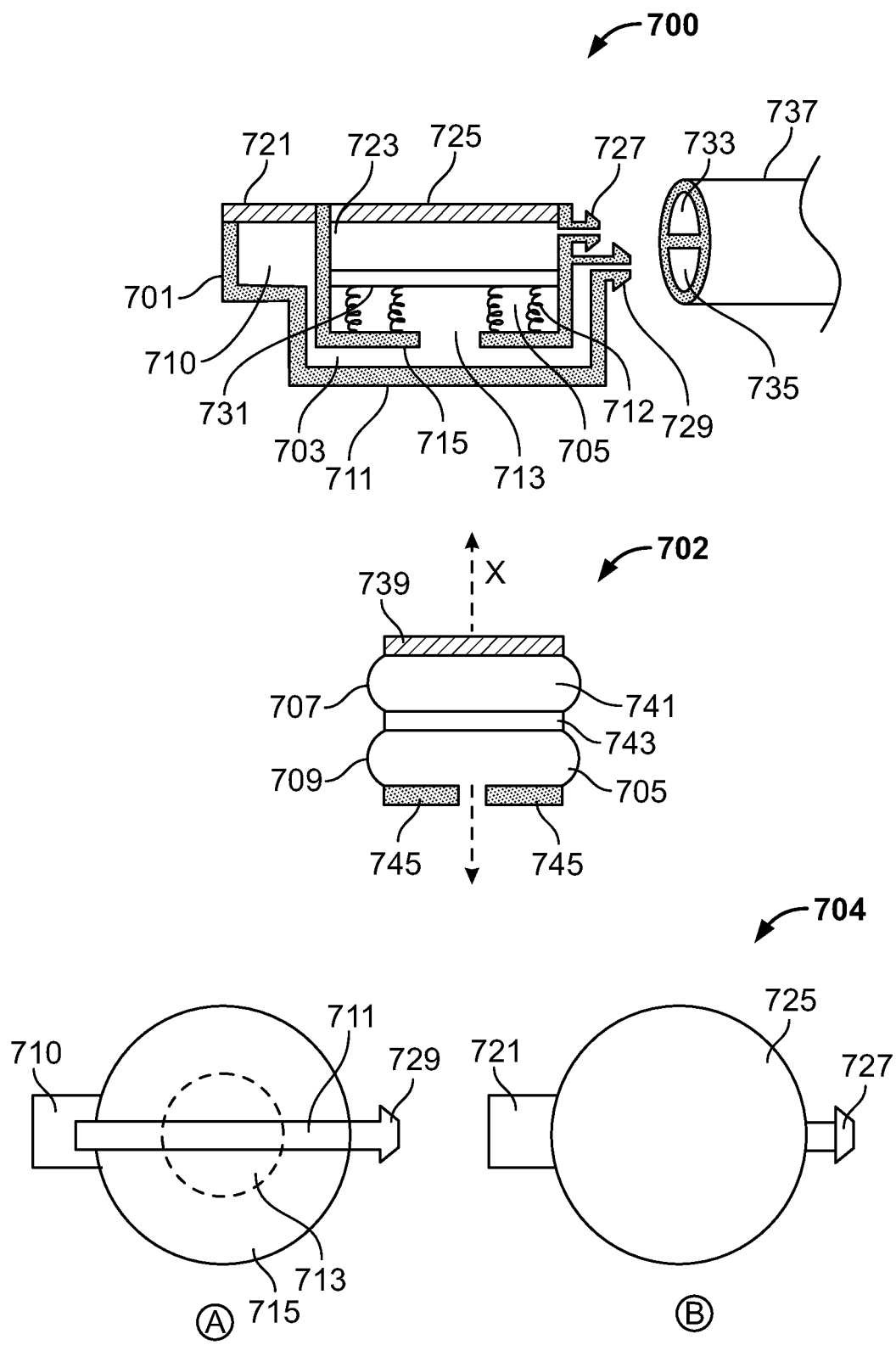
FIG. 7 shows illustrative apparatus in accordance with principles of the invention.

FIG. 7 shows illustrative apparatus 700, 702, 704A and 704B.

Apparatus 700 includes reservoir 701. Reservoir 701 may include one or more features of reservoir 223, reservoir 231 (shown in FIG. 2) or reservoir 109 (shown in FIG. 1). Apparatus 700 includes tubing 737. Tubing 737 may include one or more features of tubing 500 (shown in FIG. 5A), tubing 504 (shown in FIG. 5C), tubing 204 (shown in FIG. 2) or tubing 111 (shown in FIG. 1). A first end of tubing 737 may be joined to reservoir 701. A second end of tubing 737 may be joined to a port such as port 400 (shown in FIG. 4), port 300 (shown in FIG. 3A), port 302 (shown in FIG. 3B), port 202 (shown in FIG. 2) or port 107 (shown in FIG. 1).

Reservoir 701 includes self-sealing membranes 721 and 725. A needle may penetrate self-sealing membrane 721 and inject a medium into chamber 710. The injected medium may enter chamber 705 via channel 703 and orifice 713. Chamber 705 may be defined, at least in part, by floor 715. The injected medium may push platform 731 away from floor 715 and closer to self-sealing membrane 725.

Reservoir 701 may include biasing members 712 between platform 731 and floor 715. The biasing members may include a spring, elastic membrane or any other suitable biasing members. In response to reducing pressure applied to platform 731, platform 731 may translate towards membrane 725. A translation of platform 731 toward membrane 725 may collapse lumen 723. A collapsed lumen 723 may be expanded by inserted a needle (not shown) through membrane 725. The needle may apply pressure overcoming a biasing force of biasing members 712. Biasing members 712 may be insulated and/or sealed from a medium present in chamber 705.

Injecting the medium into chamber 710 may result in platform 731 translating towards self-sealing membrane 725. The translation of platform 731 may force a cleansing agent present in chamber 723 into lumen 733 and through passageway 207 (shown in FIG. 2). The flow of the cleansing agent through passageway 207 may sanitize lumen 733 and/or passageway 207.

Chamber 710 may be in fluid contact with lumen 735. The injected medium may flow through chamber 710 into lumen 735. Adapter 729 may fluidly join chamber 710 and lumen 735. Injection of the medium into chamber 710 may expand lumen 205 and rotate swing-arm 203 about hinge 233 (shown in FIG. 2).

In response to the injection of medium into chamber 710, platform 731 may be configured to translate and contract chamber 723. Chamber 723 may be contracted prior to the fluid exerting sufficient pressure to expand lumen 735. In response to the injection of medium into chamber 703, lumen 735 may expand, thereby sealing lumen 733. Lumen may be sealed prior the injected fluid exerting sufficient pressure to expand lumen 205 (shown in FIG. 2) and/or seal orifice 413 (shown in FIG. 4).

Apparatus 704 shows an illustrative component. Apparatus 704 included in a reservoir, such as reservoir 701, reservoir 223, reservoir 231 (shown in FIG. 2) or reservoir 109 (shown in FIG. 1). Apparatus 704 includes membrane 739. Membrane 739 may be a self-sealing membrane. Apparatus 704 may include platform 743. Platform 743 may be rigid.

Platform 743 may be configured to translate along axis X. A flow of fluid into chamber 705 may cause platform 743 to translate towards membrane 739. Translation of platform 743 toward membrane 739 may fold walls 707. Walls 707 may be biased to fold out of chamber 741. Translation of platform 743 toward membrane 739 may extend walls 709. Translation of platform 743 toward membrane 739 may expand chamber 705.

An extraction of fluid from chamber 705 may cause platform 743 to translate toward floor 745. An extraction of fluid from chamber 705 may create a negative pressure. The negative pressure may pull platform 743 toward floor 745.

Platform 743 may be biased along axis X. Platform 743 may be biased by one or more biasing members, such as biasing members 221 (shown in FIG. 2).

Translation of platform 743 toward floor 745 may fold walls 709. Walls 709 may be biased to fold out of chamber 705. Translation of platform 743 toward floor 745 may extend walls 707. Translation of platform 743 toward floor 745 may expand chamber 741.

Apparatus 704A shows an inferior view of reservoir 701. The inferior view shows an outer housing 711 of channel 703. The inferior view shows a circular area swept out by walls 715. In broken line, the inferior view shows a circular area swept out by orifice 713. The inferior view shows an underside of chamber 710. Channel 703 may terminate at adapter 729. The inferior view shows an underside of adapter 729. Channel 703 may be joined to tubing 737 using adapter 729.

Apparatus 704B shows superior view of reservoir 701. The superior view shows self-sealing membrane 725. Self-sealing membrane 725 may cap chamber 723. The superior view shows self-sealing membrane 721. Self-sealing membrane 721 may cap chamber 710. The superior view also shows a top of adapter 727. Adapter 727 may join chamber 723 and tubing 737.

Figure 8:
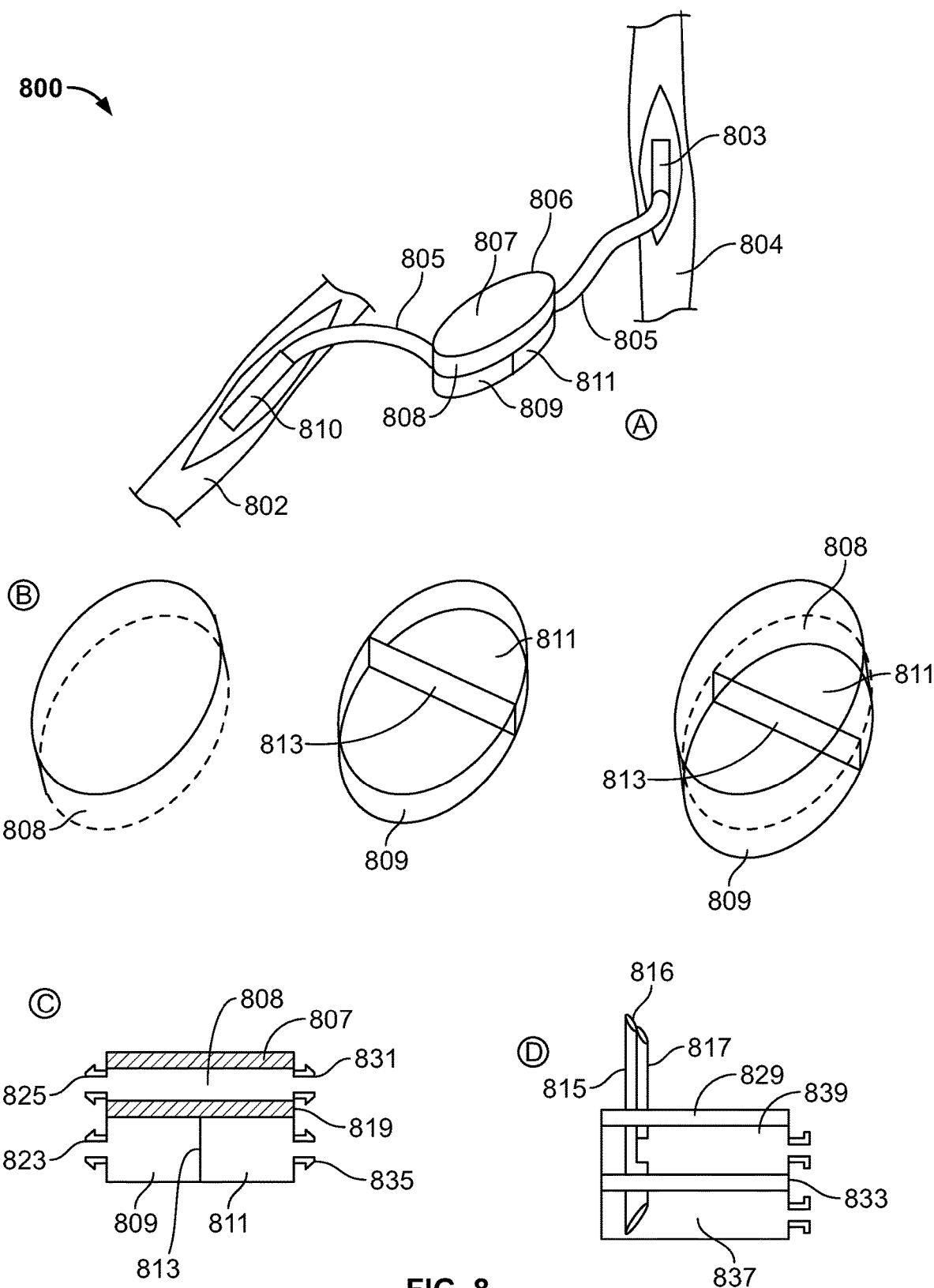
FIG. 8 shows illustrative apparatus in accordance with principles of the invention.

FIG. 8 shows illustrative apparatus 800A, 800B, 800C and exemplary therapeutic scenario 800D.

Apparatus 800A may be used to join blood vessel 802 and blood vessel 804. Apparatus 800A may provide a system that allows blood to be extracted from one of blood vessels 802 or 804 and returned to one of blood vessels 802 or 804. Blood extracted from blood vessel 802 or 804 may be processed before being reintroduced into circulation. The extracted blood may be dialysized before being returned to circulation. Apparatus 800A may provide a system that allows for blood to selectively flow between blood vessel 802 and blood vessel 804. Apparatus 800A may provide a system that prevents blood from continuously flowing between blood vessel 802 and blood vessel 804. For example, when blood is not being processed, blood may not flow through port 810, port 803, tubing 805 or reservoir 806.

Apparatus 800A includes port 803. Port 803 may include one or more features of port 202 (shown in FIG. 2), ports 300 and 302 (shown in FIG. 3) and port 400 (shown in FIG. 4). Apparatus 800A includes port 810. Port 810 may include one or more features of port 202 (shown in FIG. 2), ports 300 and 302 (shown in FIG. 3) and port 400 (shown in FIG. 4).

Port 803 may be affixed to blood vessel 802. Port 803 may be affixed to blood vessel 804. Port 803 may be affixed to blood vessel 802 or 804 using any suitable technique such as the techniques shown in FIG. 5G.

Port 803 may be joined to tubing 805. Tubing 805 may include one or more features of tubing 111 (shown in FIG. 1), tubing 204 (shown in FIG. 2) and any tubings shown in FIGS. 5A-5G. In some embodiments (not shown), tubing 805 may be joined to blood vessel 802 or 804 without port 803.

Tubing 805 may be joined to blood vessel 802 or 804 using any suitable technique such as the exemplary techniques shown in FIG. 5G.

Tubing 805 may join port 803 to reservoir 806. Tubing 805 may be joined to port 803 using adapters 239 or 241 (shown in FIG. 2), adapters 315 or 313 (shown in FIG. 3A), a "Christmas tree" type adapter, threaded screw or any suitable adapter. Tubing 805 may be fused to port 803.

Apparatus 800B and 800C show illustrative components of reservoir 806. Apparatus 800B includes chambers 808, 809 and 811. Chambers 809 and 811 may each include one or more features of reservoir 601. For example, each of chambers 809 and 811 may be biased with respect to chamber 808 by biasing members such as biasing members 619.

Chamber 808 may be stacked above chambers 809 and 811. In some embodiments (not shown), chambers 809 and 811 may be stacked above chamber 808. Chamber 808 may be capped with membrane 807 (shown in 800A). Membrane 807 may be a self-sealing membrane. Chambers 809 and 811 may be separated by dividing wall 813. Dividing wall 813 may be an impermeable barrier. Apparatus 800C shows that chamber 808 may be separated from chambers 809 and 811 by membrane 819. Membrane 819 may be a self-sealing membrane.

Tubing 805 may be coupled to chambers 808 and 811 via adapters 831 and 835. Tubing 805 may be coupled to chambers 808 and 809 via adapters 825 and 823.

Extracting a medium present in chamber 808 may unseal a swing-arm within port 803 (shown in 800A) and/or port 810. Extracting a medium present in chamber 808 may unseal a lumen in tubing 805. Unsealing the lumen within tubing 805 and the swing-arm within port 803 may allow blood to flow between port 803 and chamber 811. Unsealing the lumen within tubing 805 and the swing-arm within port 810 may allow blood to flow between port 810 and chamber 809.

A needle (not shown) may penetrate membranes 807 and 819 and extract blood from chamber 811. By accessing chamber 811, blood may be extracted from blood vessel 804 (shown in 800A). Blood vessel 804 may be an artery. A needle (not shown) may penetrate membranes 807 and 819 and inject filtered blood into chamber 809. By accessing chamber 809, blood may be injected into blood vessel 802 (shown in 800A). Blood injected into chamber 809 may flow through tubing 805, though port 810 and into blood vessel 802. Blood vessel 802 may be a vein. Blood vessel 802 may be a vein.

Blood extracted from chamber 811 may be filtered by dialysis machine 115 and returned to chamber 809. After a completion of a dialysis procedure, a medium, such as heparinized saline, may be injected into chamber 811 and/or chamber 809. Injection of the medium may flush any residual blood within chamber 811, chamber 809, tubing 805, port 810 and/or port 803.

A medium may be injected into chamber 808. Injecting the medium into chamber 808 may insulate tubing 805 and port 803 from blood flow in blood vessel 804. Tubing 805 may be constructing with varying degrees of bending resistance so that a first portion of tubing 805 closer to chamber 811 is sealed prior to a second portion of tubing 805 closer to port 803. Tubing 805 may be sealed prior to sealing port 803.

In some embodiments, a cleansing solution, such as heparinized saline may be injected into chamber 811. The heparinized saline may clear blood present in chamber 811, tubing 805 and/or port 803. Following injection of the heparinized saline, a medium may be injected into lumen 808 sealing the transport system.

Injecting the medium into chamber 808 may seal tubing 805 and port 810 from blood flow within blood vessel 802. Tubing 805 may be constructing with varying degrees of bending resistance so that a first portion of tubing 805 closer to chamber 811 is sealed prior to a second portion of tubing 805 closer to port 810. Tubing 805 may be sealed prior to sealing port 810.

A needle inserted into reservoir 806 may include a pressure gauge (not shown). When the pressure gauge registers a threshold pressure, tubing 805, port 803 and port 810 may all be sealed from blood flow in vessels 804 and 802. Membrane 807 and membrane 819 may maintain the threshold pressure within chamber 808 after needle 816 is withdrawn.

In some embodiments, reservoirs 808, 809 and 811 may be positioned adjacent to one another in a plane. For example, reservoirs 808, 809 and 811 may form a "three leaf clover" shape. Each of reservoirs 808, 809 and 811 may be a different shape. For example, reservoir 808 may have a circular shape. Reservoir 809 may have a square shape. Reservoir 811 may have a triangular shape. The different shapes may allow a practitioner accessing the reservoirs to identify each reservoir by feeling or palpitating each reservoir.

Scenario 800D shows an exemplary therapeutic scenario utilizing a "stacked" reservoir. The stacked reservoir may include one or more features of reservoir 806 (shown in 800A). In scenario 800D, double lumen needle 816 is inserted into chamber 837 by penetrating membranes 829 and 833. Membrane 829 may include one or more features of membrane 807 (shown in 800C). Membrane 833 may include one or more features of membrane 819 (shown in 800C). Lumen 817 may only penetrate membrane 829. Lumen 815 may penetrate both membrane 829 and 833. Lumen 817 may extract a medium from within chamber 839.

Extracting the medium from chamber 839 may unseal a swing-arm within a port such as port 803 and/or port 810 (shown in 800A). The swing-arm may include one or more features of swing-arm 203 (shown in FIG. 2), swing-arm 309 (shown in FIG. 3) or swing-arm 421 (shown in FIG. 4). For example, port 803 may be coupled to chamber 839 via a tubing connection such as tubing 805 (shown in 800A). Unsealing the swing-arm may allow blood to flow from blood vessel 804 (shown in 800A) into port 803. The swing-arm may seal an orifice (not shown) between blood vessel 804 and housing 803. The orifice may include one or more features of orifice 321 (shown in FIG. 3) or orifice 413 (shown in FIG. 4).

Extracting the medium from chamber 839 may unseal a lumen (not shown) within the tubing coupled to chamber 839. For example, tubing 805 may be coupled to chamber 839, and a lumen within tubing 805 may include one or more features of lumen 211 (shown in FIG. 2), lumen 501 (shown in FIG. 5A) or lumen 514 (shown in FIG. 5C). Unsealing the lumen may allow blood to flow into chamber 837. Blood flowing into chamber 837 may be extracted via lumen 815 of needle 816. Blood extracted via lumen 815 may be transferred to dialysis machine 115 using feeds 113 (shown in FIG. 1). Blood extracted via lumen 815 from chamber 837 may be filtered by dialysis machine 115 and returned to chamber 809 (shown in 800A) or a reservoir such as reservoir 223 (shown in FIG. 2).

Figure 9:
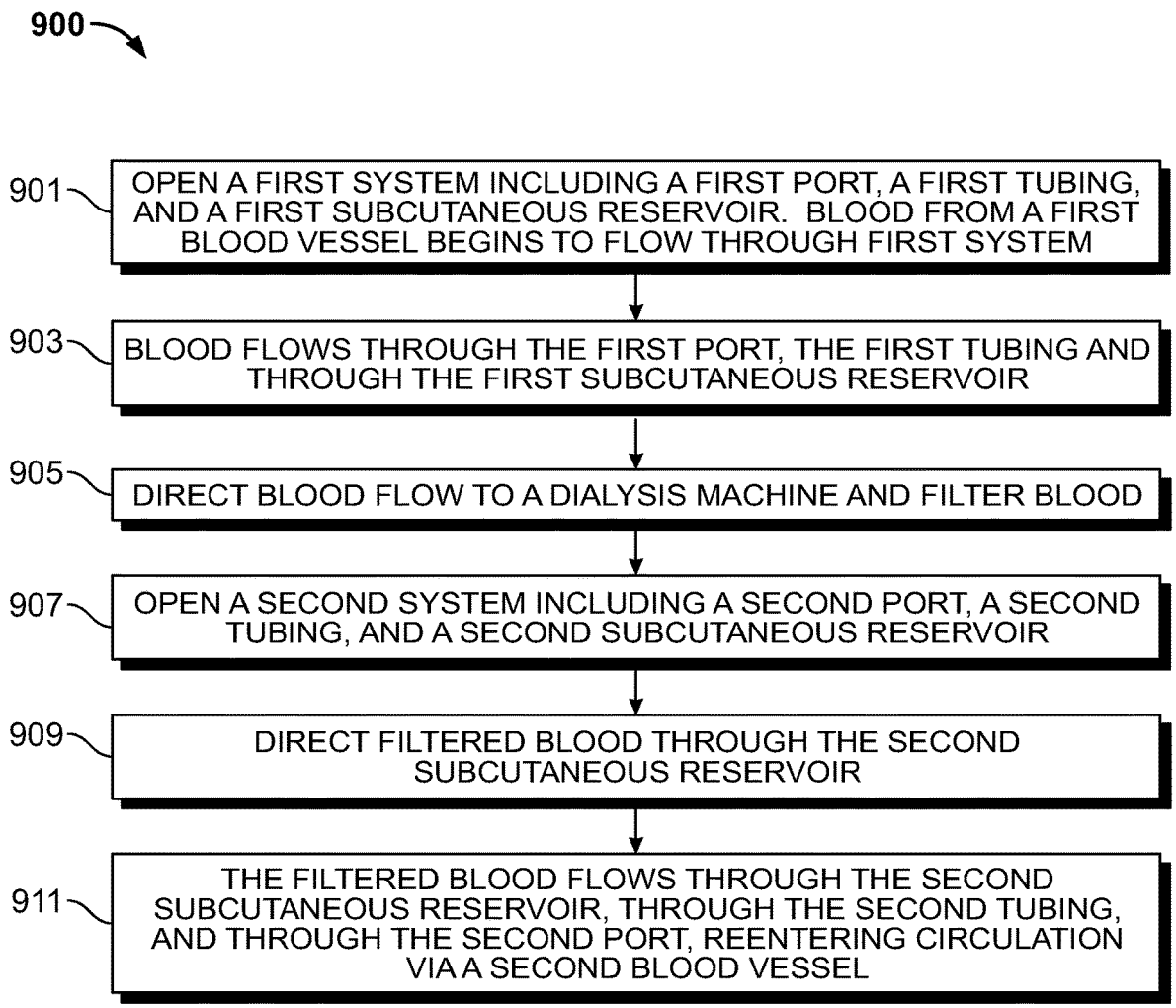
FIG. 9 shows an illustrative process in accordance with principles of the invention.

FIG. 9 shows illustrative process 900. Process 900 includes, at step 901, opening a first system. The first system may include a first port. The first port may include one or more features of port 803 (shown in FIG. 8), port 300 (shown in FIG. 3A), port 202 (shown in FIG. 2) or port 107 (shown in FIG. 1). The first system may include a first tubing. The first tubing may one or more features of tubing 805 (shown in FIG. 8), tubing 500 (shown in FIG. 5A), tubing 504 (shown in FIG. 5C), tubing 204 (shown in FIG. 2) or tubing 111 (shown in FIG. 1). The first system may include a first subcutaneous reservoir. The first reservoir may include one or more features of reservoir 806 (shown in FIG. 8), reservoir 231 (shown in FIG. 2) or reservoir 109 (shown in FIG. 1).

Opening the first system may allow blood from a first blood vessel to flow through the first system. At step 903, blood flows through the first port, the first tubing and through the first subcutaneous reservoir. At step 905, blood flowing through the first system is directed to a dialysis machine. The dialysis machine filters the blood.

At step 907, a second system is opened. The second system may include one or more features of the first systems. For example the second system may include a second port, a second tubing, and a second subcutaneous reservoir. At step, 909, filtered blood is transferred from the dialysis machine to the second subcutaneous reservoir. At step 911, the filtered blood flows through the second subcutaneous reservoir, through the second tubing, and through the second port. The second port returns the filtered blood circulation via a second blood vessel.

Figure 10:
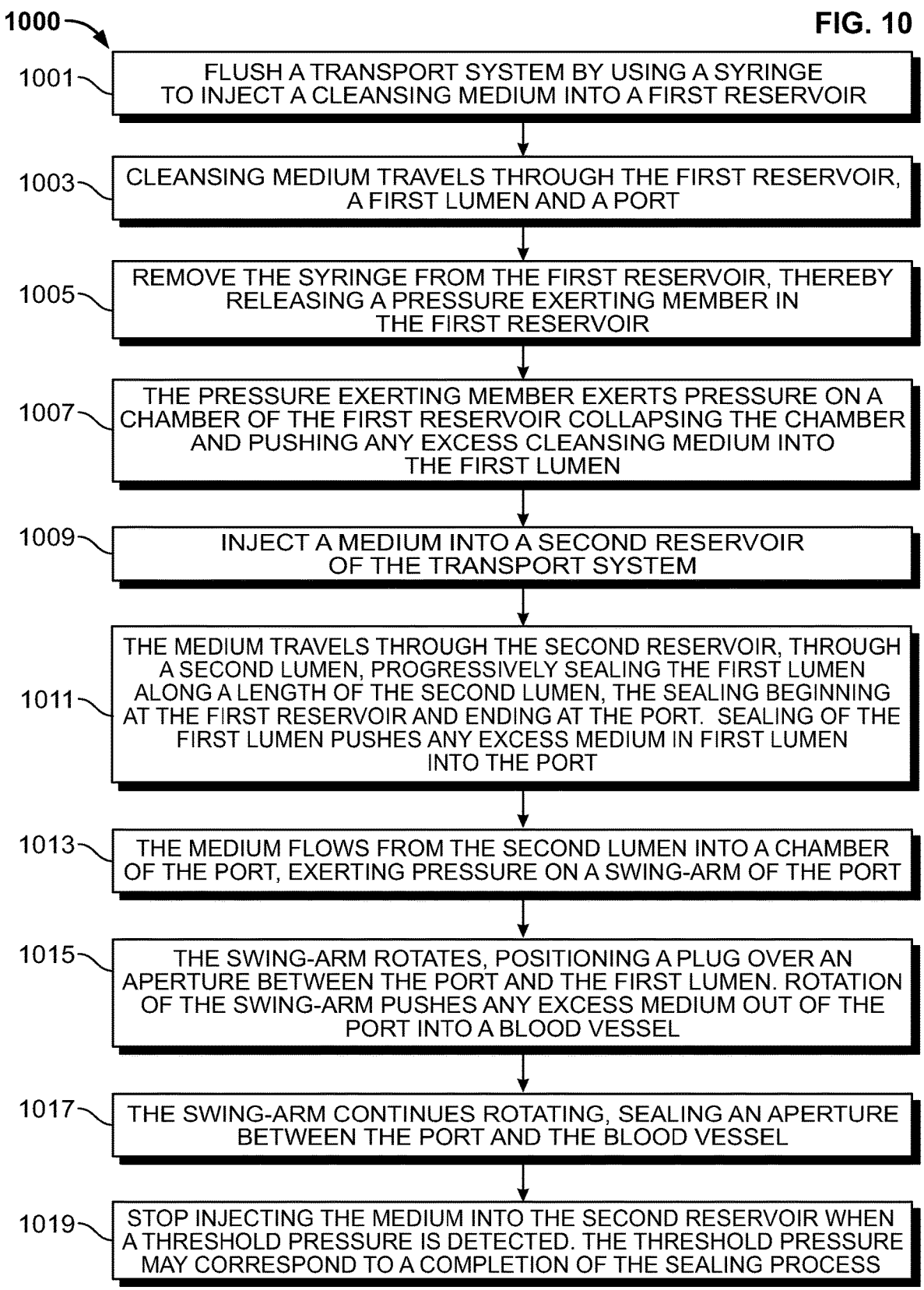
FIG. 10 shows an illustrative process in accordance with principles of the invention.

FIG. 10 shows illustrative process 1000. Process 1000 includes, at step 1001, flushing a transport system. The transport system may include one or more features of apparatus 800A (shown in FIG. 8) or apparatus 200 (shown in FIG. 2). For example the transport system may include a first reservoir such as reservoir 206 (shown in FIG. 2), a first lumen such as lumen 501 (shown in FIG. 5) and a port such as port 400 (shown in FIG. 4). The first lumen may be coupled to the first reservoir. The flushing may include, using a syringe, injecting a cleansing medium into a first reservoir.

At step 1003, the cleansing medium travels through the first reservoir, the first lumen and the port. At step 1005, a needle is removed from the first reservoir. Removing the needle releases a pressure exerting member in the first reservoir. For example, the pressure exerting member may correspond to spring 221 (shown in FIG. 2). At step 1007, the pressure exerting member exerts pressure on a chamber of the first reservoir and collapses the chamber. For example, the chamber may correspond to chamber 213 (shown in FIG. 2), chamber 723 (shown in FIG. 7) or chamber 809 (shown in FIG. 8). Collapsing the chamber pushes any excess cleansing medium out of the chamber into the first lumen.

At step 1009, a medium is injected into a second reservoir of the transport system. The second reservoir may include one or more features of reservoir 231 (shown in FIG. 2), reservoir 701 (shown in FIG. 7) or reservoir 806 (shown in FIG. 8).

At step 1011, the medium travels through the second reservoir and through a second lumen. The second lumen may be coupled to the second reservoir. As the medium travels through the second lumen, the second lumen may expand progressively sealing the first lumen. For example, the second lumen may correspond to lumen 735 and the first lumen may correspond to lumen 733 (shown in FIG. 7).

Expansion of the second lumen may progressively seal the first lumen along a length of the second lumen. The second lumen may be configured to seal the first lumen beginning at a point the first lumen is coupled to the first reservoir and ending at a point the first lumen is coupled to the port. Progressively sealing of the first lumen pushes any excess medium in first lumen into the port.

At step 1013, the medium injected into the second reservoir flows from the second lumen into a chamber of the port. The flow of medium into the port exerts pressure on a swing-arm of the port. The swing-arm may include one or more features of swing-arm 203 (shown in FIG. 2), sealing member 309 (shown in FIG. 3A) or sealing member 421 (shown in FIG. 4).

In response to the pressure exerted on the swing-arm, the swing-arm rotates, positioning a plug over an aperture between the port and the first lumen. Rotation of the swing-arm pushes any excess medium out of the port into a blood vessel. At step 1017, in response continued flow of medium into the chamber and corresponding pressure exerted on the swing-arm, the swing-arm continues rotating, sealing an aperture between the port and the blood vessel. The aperture may include one or more features of orifice 419 (shown in FIG. 4) or orifice 305 (shown in FIG. 3A) orifice.

At step 1019, a threshold pressure is monitored at the point of injection into the second reservoir. In response to detection of the threshold pressure, the needle is withdrawn from the second reservoir. The threshold pressure may correspond to a completion of the sealing process. A self-sealing membrane may prevent a change in pressure after withdrawing the needle.

Figure 11:
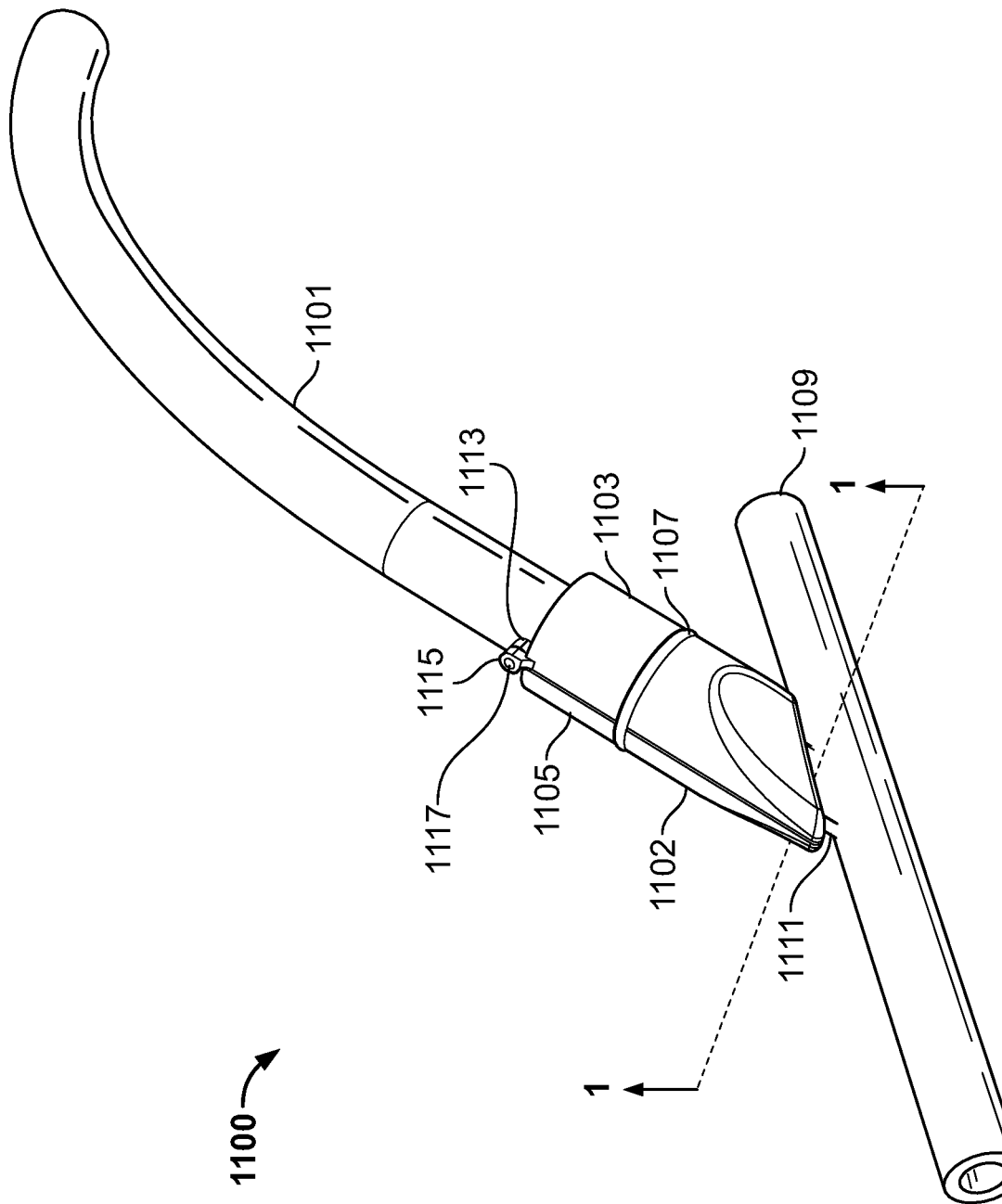
FIG. 11 shows an illustrative therapeutic scenario and associated apparatus in accordance with principles of the invention.

FIG. 11 shows illustrative apparatus 1100. Apparatus 1100 includes tubing 1101. Apparatus 1100 includes clamp 1102. Clamp 1102 includes first rotatable arm 1103 and second rotatable arm 1105. First rotatable arm 1103 is affixed to tubing 1102 via hinge 1115. Second rotatable arm 1105 is affixed to tubing 1101 via hinge 1113.

Hinges 1113 and 1115 may be aligned over pivot 1117. Pivot 1117 may protrude from tubing 1101. Hinges 1113 and 1115 may be configured to rotate about pivot 1117. Clamp 1102 may be affixed to tubing 1101 after tubing 1101 is anastomized to blood vessel 1109. Hinges 1113 and 1115 may be fitted over a pivot 1117 after tubing 1101 is anastomized to blood vessel 1109. In some embodiments, clamp 1102 may be manufactured as part of tubing 1101.

Clamp 1102 includes O-ring 1107. O-ring 1107 may bias rotatable arms 1103 and 1105 to compress flexible tubing portion 1111. FIG. 11 shows clamp 1102 in a closed position. O-ring 1107 may maintain clamp 1102 in the closed position. In the closed position, clamp 1102 compresses flexible portion 1111 of tubing 1101.

When clamp 1102 compresses flexible portion 1111, tubing 1101 is insulated from blood or any other medium flowing through vessel 1109. When clamp 1102 compresses flexible portion 1111, fluid present in tubing 1101 is insulated from vessel 1109. When clamp 1102 compresses flexible portion 1111 of tubing 1101, fluid flowing through vessel 1109 may flow across an anastomization site unimpeded by any portion of tubing 1101.

Figure 12:
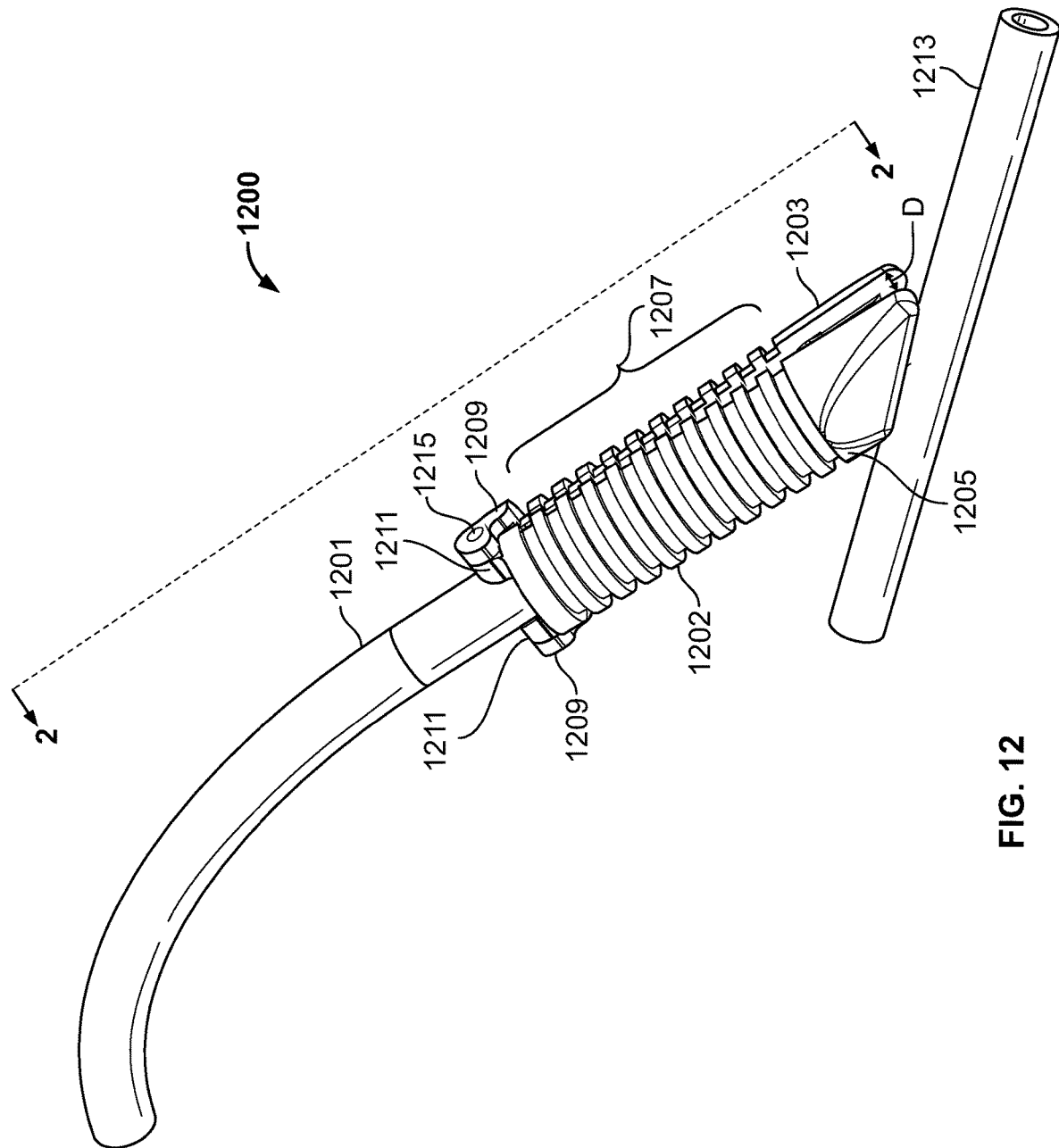
FIG. 12 shows an illustrative therapeutic scenario and associated apparatus in accordance with principles of the invention.

FIG. 12 shows illustrative apparatus 1200. Apparatus 1200 includes tubing 1201. Tubing 1201 may be anastomized to conduit 1213. Conduit 1203 may be any fluid carrying medium such as an artery or vein. Apparatus 1200 includes clamp 1202. Clamp 1202 may include one or more features of clamp 1102 (shown in FIG. 11).

Clamp 1202 includes rotatable arms 1203 and 1205. Hinges 1211 may rotatably fix rotatable arm 1203 to tubing 1201. Hinges 1209 may rotatably fix rotatable arm 1205 to tubing 1201. Rotatable hinges 1211 and 1209 may rotate about pivot 1215. Some embodiments may not include hinges. For example, rotatable arms 1203 and 1205 may be clipped or otherwise affixed to tubing 1201. A bending resistance of rotatable arms 1203 and 1205 may provide flexibility for clamp 1202 to expand and contract.

Clamp 1202 includes O-ring positions 1207. Each of O-ring positions 1207 may be configured to position an O-ring around clamp 1202. An O-ring position may be selected based on a property of the conduit, tubing, anastomosis, clamp or any suitable requirement. In some embodiments, the clamp may include one pre-determined O-ring position.

FIG. 12 shows clamp 1202 in an open position. In the open position, rotatable arms 1203 and 1205 are separated by distance D. Opening clamp 1202 may pivot rotatable arms 1203 and 1205 about pivot 1215. An amount of force needed to open clamp 1202 may depend on a seating of O-ring(s) within one or more of O-ring positions 1207.

Opening clamp 1202 a distance D may allow fluid flowing thorough conduit 1213 to enter tubing 1201.

Figure 13A:
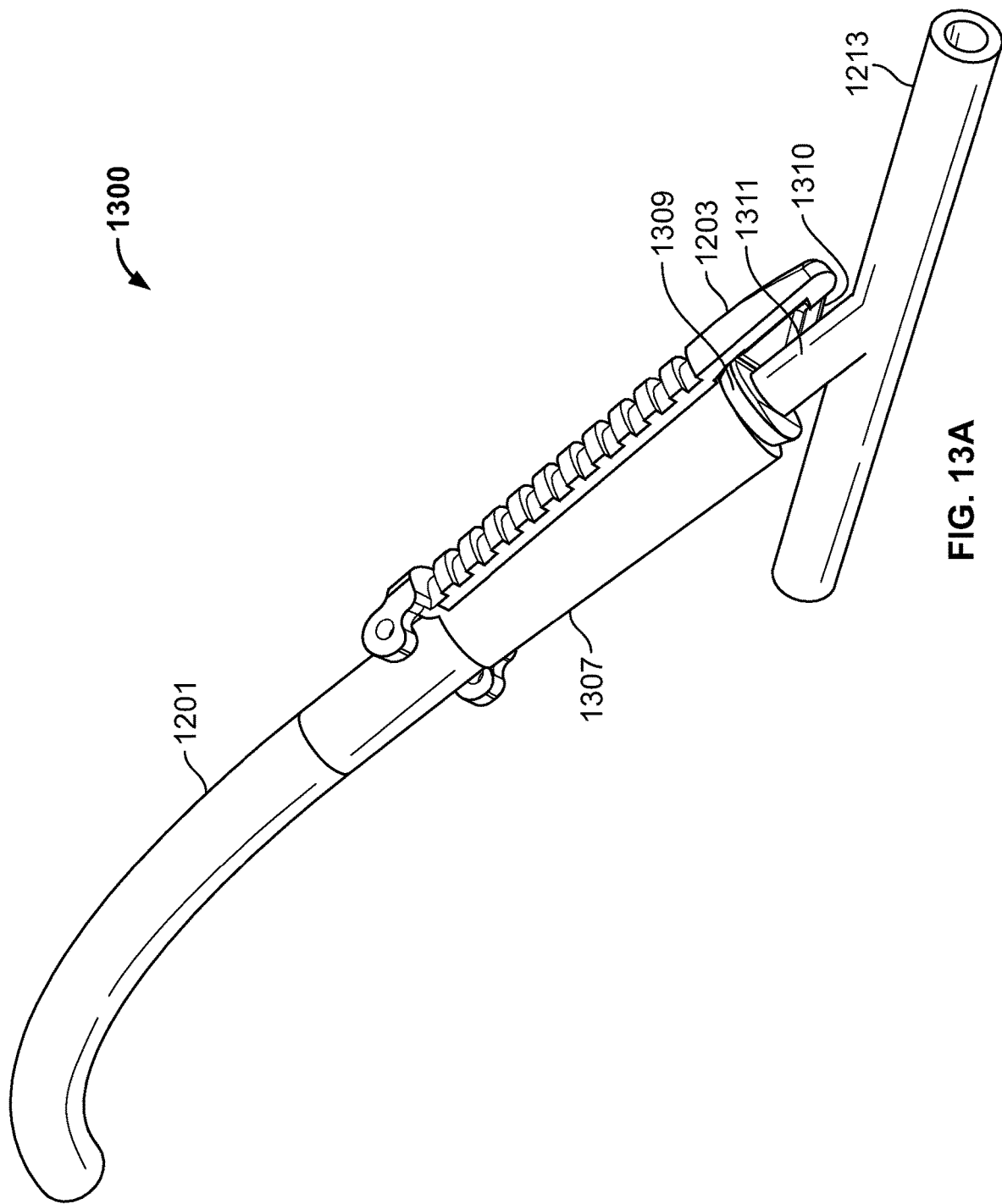
FIG. 13A shows an illustrative therapeutic scenario and associated apparatus in accordance with principles of the invention.

FIG. 13A shows illustrative apparatus 1300. Apparatus 1300 shows apparatus 1200 without rotatable arm 1205 exposing balloon 1307, end cap 1309, shoulder 1310 and tubing section 1311.

Balloon 1307 may encircle tubing section 1311. Tubing section 1311 may extend concentrically though tubing section 1201. Tubing section 1311 may include a compressible segment. Tubing section 1311 may include a non-compressible segment. Balloon 1307 may completely or partially encircle the non-compressible segment of tubing 1310. Balloon 1307 may be in fluid communication with fluid carried in tubing 1201. The fluid flowing through tubing 1201 may be used to inflate balloon 1307. End cap 1309 may prevent the fluid from leaking out of balloon 1307 and tubing 1201.

Inflating balloon 1307 may rotate rotatable arm 1203 and 1205 (shown in FIG. 12) opening clamp 1202 (shown in FIG. 12). Balloon 1307 may be deflated by allowing fluid to exit balloon 1307 through tubing 1201. Deflating balloon 1307 may allow clamp 1202 to compress tubing section 1311. Shoulder 1310 may compress a portion of tubing section 1311. A portion of tubing section 1311 extending through end cap 1309, balloon 1307 and tubing 1201 may retain a circular cross section even when clamp 1202 is closed.

Figure 13B:
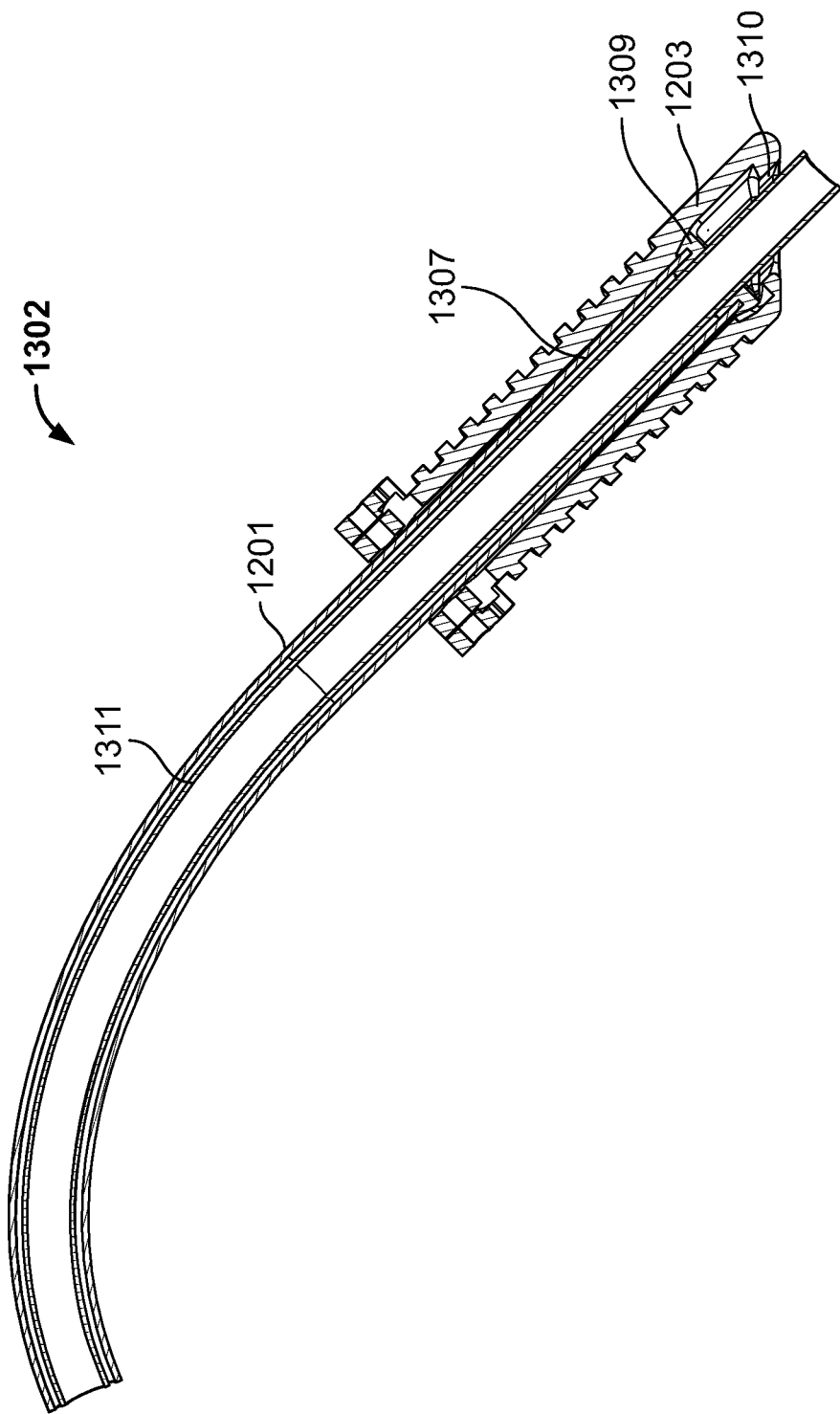
FIG. 13B shows illustrative apparatus in accordance with principles of the invention.

FIG. 13B shows illustrative apparatus 1302. Apparatus 1302 shows a cross-section of apparatus 1300 taken along lines 2-2 shown in FIG. 12. Apparatus 1302 shows outer tubing 1201 and inner tubing 1311. Fluid for inflating balloon 1307 may flow in a space between outer tubing 1201 and inner tubing 1311.

Inner tubing 1311 may include a compressible segment and a non-compressible segment. Balloon 1307 may extend along a non-compressible segment of inner tubing 1311. A shoulder 1310 may be positioned about a compressible segment of inner tubing 1311. A compressible segment of inner tubing 1311 may be anastomized to conduit 1213 (shown in FIG. 12).

Apparatus 1302 shows end cap 1309 sealing and end of balloon 1307. Apparatus 1302 shows that end cap 1309 may provide a "seat" for positioning rotatable arm 1203 relative to an anastomosis site.

Figure 14:
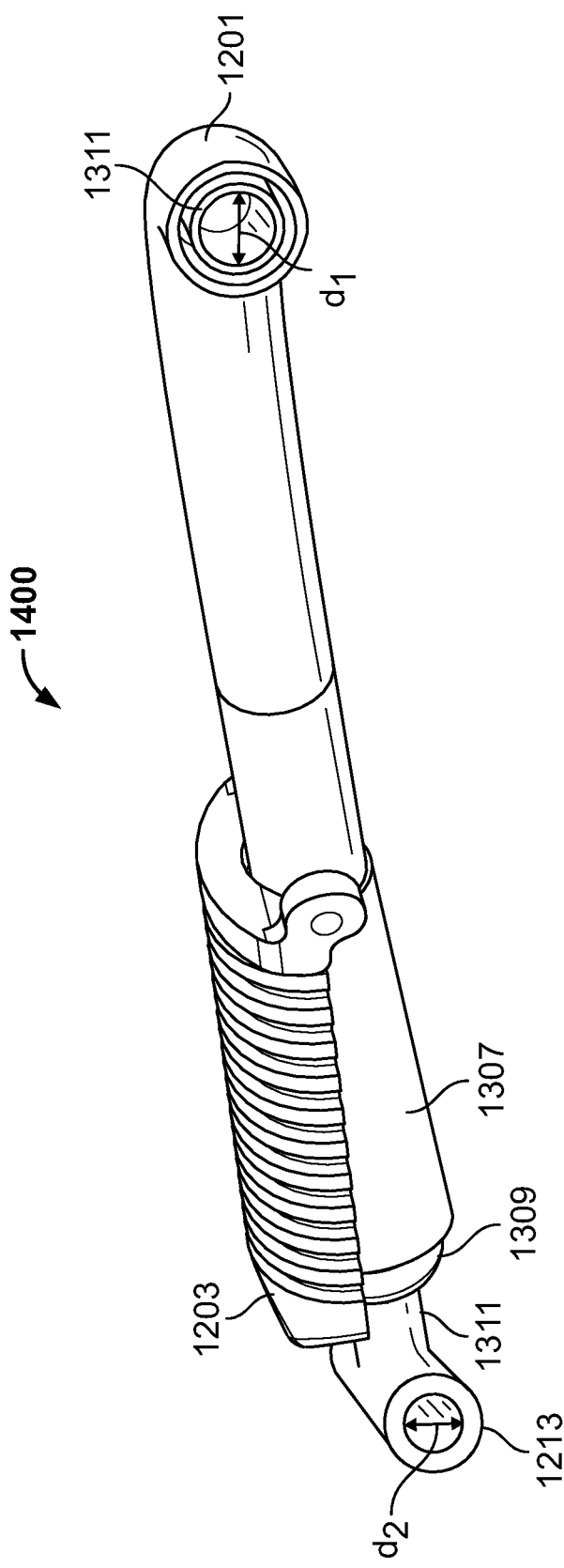
FIG. 14 shows an illustrative therapeutic scenario and associated apparatus in accordance with principles of the invention.

FIG. 14 shows illustrative view 1400 of apparatus 1301 (shown in FIG. 13A). View 1400 shows a first segment of inner tubing 1311 having a tubular diameter of d1. Inner tubing 1311 may be configured to transport fluid siphoned off from conduit 1213. Diameter d1 may be selected based on a diameter of d2 of conduit 1213. Diameter d1 may be selected to obtain a target throughput of fluid when clamp 1203 is open.

Fluid may be present in a space between outer tubing 1201 and inner tubing 1311. The fluid present in the space may be saline, water or any suitable fluid for inflating balloon 1307.

Figure 15A:
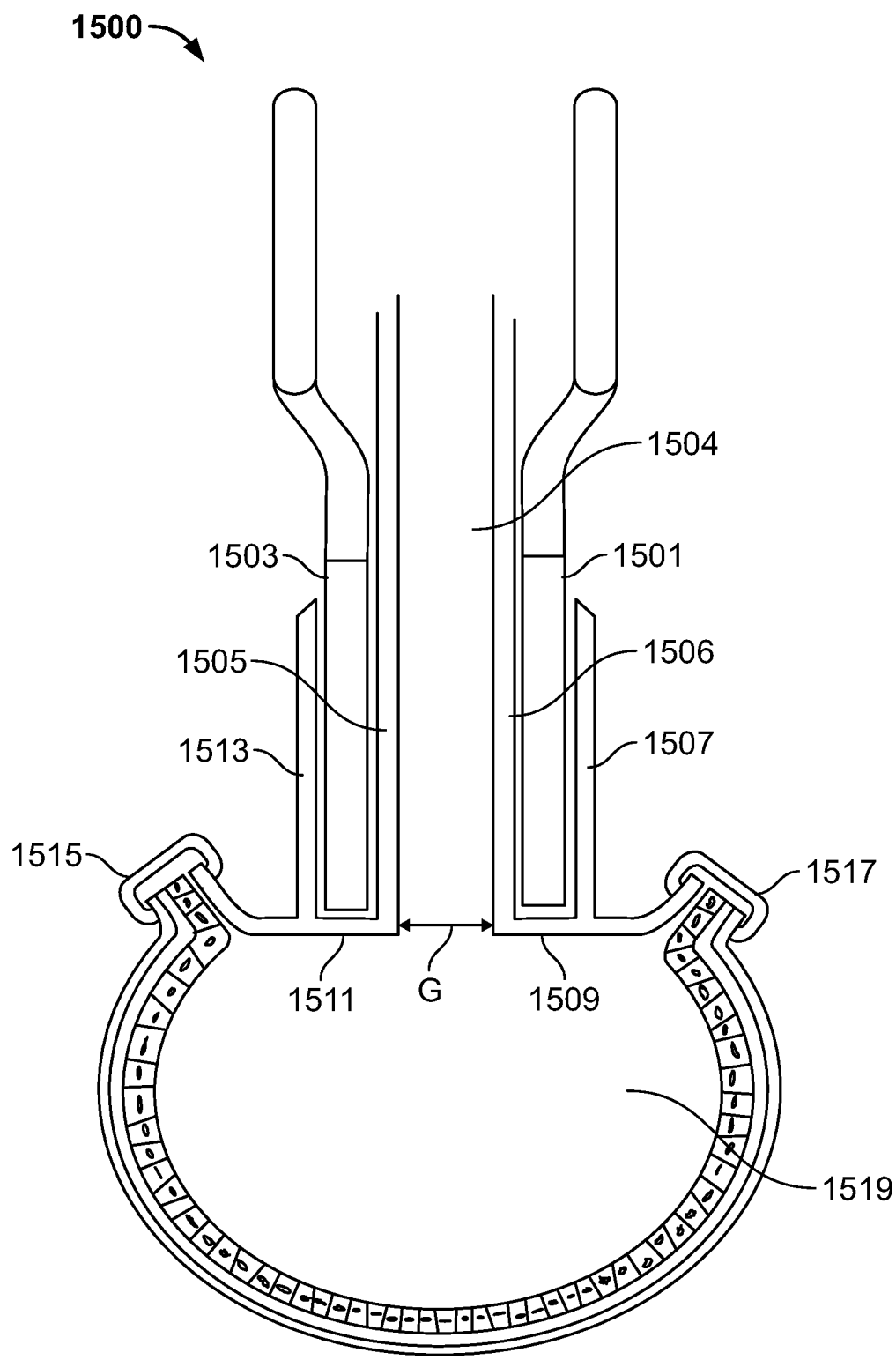
FIG. 15A shows an illustrative therapeutic scenario and associated apparatus in accordance with principles of the invention.

FIG. 15A shows illustrative therapeutic scenario 1500. Scenario 1500 shows an illustrative anastomization of tubing 1504 to conduit 1519. Conduit 1519 may be a blood vessel. Tubing 1504 may include flared ends 1509 and 1511. Flared ends 1509 and 1511 may be anastomized to conduit 1519 using sutures 1515 and 1517.

Scenario 1500 shows a portion of a clamp positioned over tubing 1504. The clamp includes rotatable arms 1503 and 1501. Rotatable arm 1503 is positioned within sleeve 1513. Sleeve 1513 is formed from flared end 1511 and outer wall 1505 of tubing 1504. Sleeves may be formed from any suitable material such as Dacron, Gore-Tex, polytetrafluoroethylene ("PTFE"), fluoropolymer products and any material suitable for implantation in a human body. Flared end 1511 may include material substantially perpendicular to outer wall 1505 and material substantially parallel to outer wall 1505.

Rotatable arm 1501 is positioned within sleeve 1507. Sleeve 1507 may be formed from flared end 1509 and outer wall 1506 of tubing 1504. Flared end 1509 may include material substantially perpendicular to outer wall 1506 and material substantially parallel to outer wall 1506.

A sleeve may take on different shapes. A sleeve may be constructed with a shape to decrease its footprint in a transverse dimension. For example, arms 1501 and 1503 may each be retracted slightly superiorly to the anastomosis site. Inferior aspects of outer wall 1505 may be fused to material 1513. Inferior aspects of outer wall 1506 may fused to material 1507. This would allow the device to have a thinner overall transverse dimension at the anastomotic site but still maintain a tight seal when arms 1501 and 1503 close about tubing 1504.

When the clamp is in an open position, rotatable arms 1503 and 1501 may be separated by gap G. Gap G may allow a fluid carried by conduit 1519 to enter tubing 1504. When the clamp is in a closed position, outer walls 1505 and 1506 may be compressed to eliminate gap G. Outer walls 1505 and 1506 may be compressed so that flared end 1511 is substantially flush with flared end 1509.

Figure 15B:
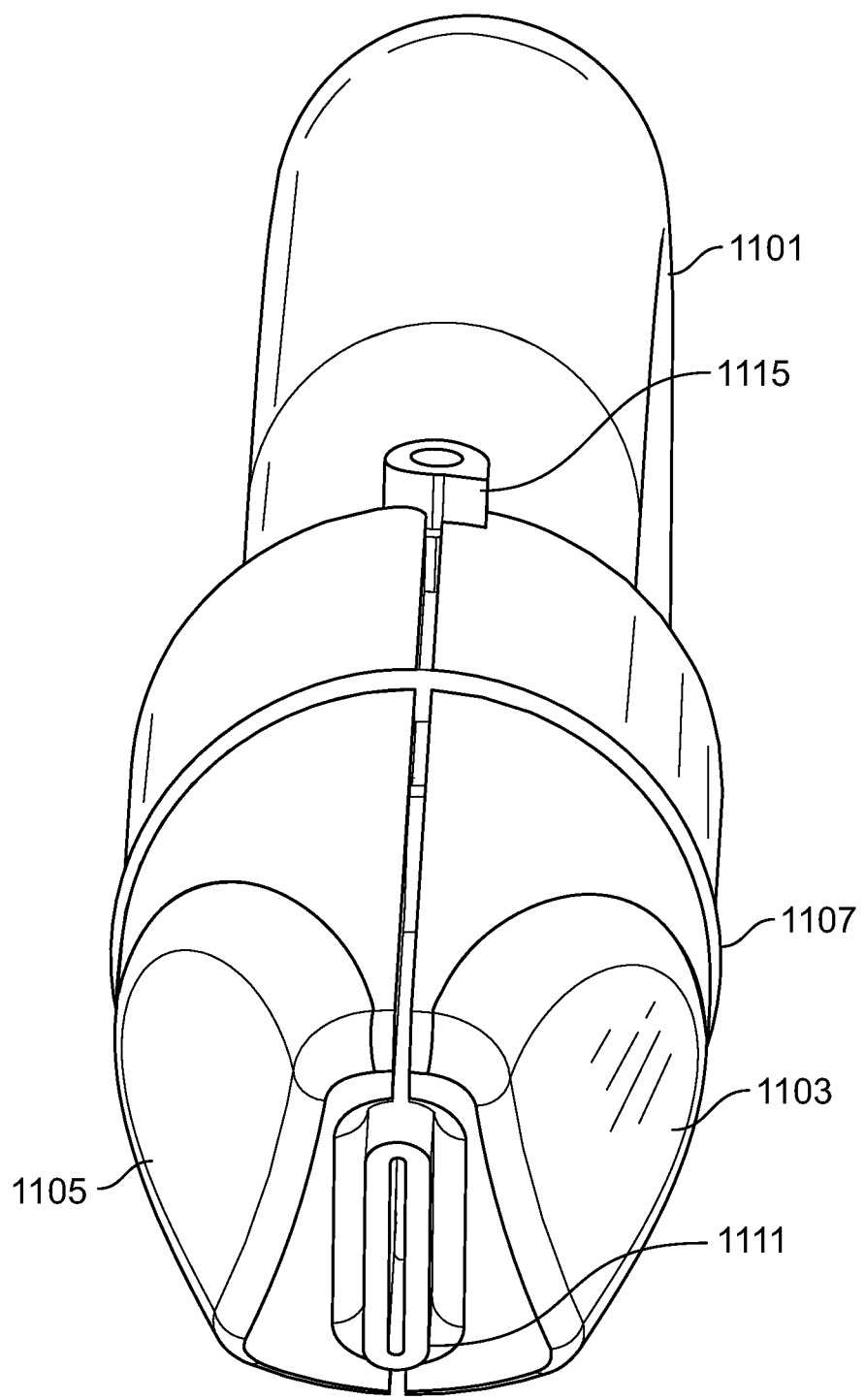
FIG. 15B shows illustrative apparatus in accordance with principles of the invention.

FIG. 15B shows illustrative view 1502 taken along line 2-2 shown in FIG. 11. View 1502 shows rotatable arms 1103 and 1105 crimping tubing 1111. O-ring 1107 may bias rotatable arms 1103 and 1105 to crimp tubing 1111. The crimping of tubing 1111 may collapse a lumen of tubing 1111. The crimping of tubing 1111 may seal tubing 1111 by pressing outer walls of tubing 1111 flush with each other.

Inflating a balloon positioned underneath rotatable arms 1103 and 1105 may allow tubing 1111 to expand and reopen a lumen through tubing 1111.

Figure 16:
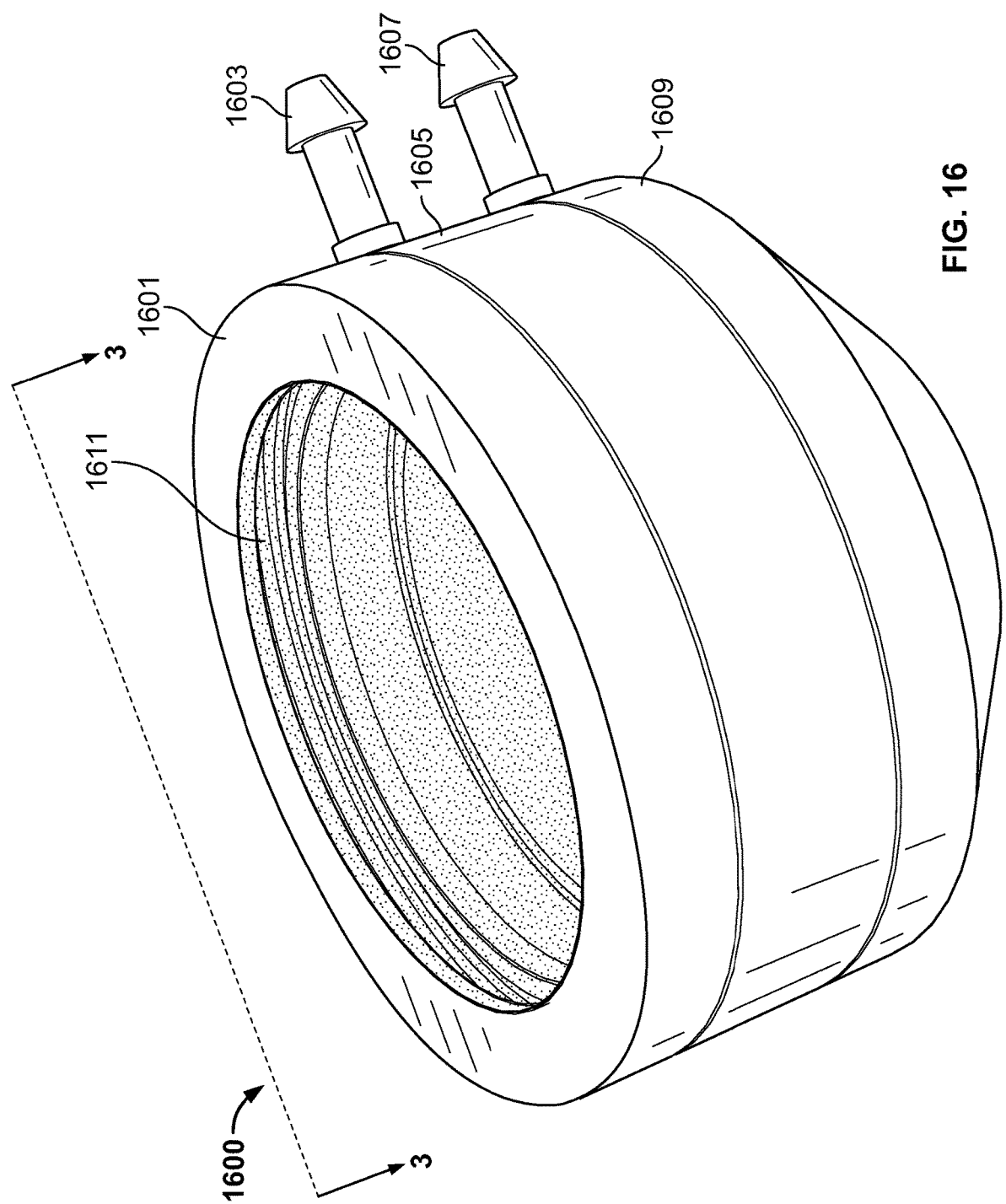
FIG. 16 shows illustrative apparatus in accordance with principles of the invention.

FIG. 16 shows illustrative reservoir 1600. Reservoir 1600 may be implanted in a human body. Reservoir 1600 includes septum 1611. Septum 1611 may include a self-sealing membrane. A needle may penetrate septum 1611 to access contents of reservoir 1600. Reservoir 1600 may be implanted subcutaneously. The needle may penetrate human tissue before penetrating septum 1611. Retainer ring 1601 may secure septum 1611 to reservoir 1600.

Fluid may pool in a first chamber of reservoir 1600. The first chamber may be defined, at least in part, by housing 1605. Retainer ring 1601 may secure septum 1611 to reservoir 1600 and prevent a leakage of contents out of the first chamber.

Reservoir 1600 includes barb 1603. Barb 1603 provides fluid communication into housing 1605. Barb 1603 may be inserted into tubing, such as tubing 1101 (shown in FIG. 11). Fluid may be inserted into the first chamber via barb 1603. Fluid may be extracted from first chamber via barb 1603.

Fluid may pool in second chamber enclosed, at least in part, by housing 1609. The second chamber may not be in fluid communication with first chamber. A platform (not shown) may fluidly seal the first chamber from the second chamber.

Fluid may be inserted into the second chamber via barb 1607. Fluid may be extracted from the second chamber via barb 1607. Barb 1607 may be inserted into tubing, such as tubing 1201.

Figure 17:
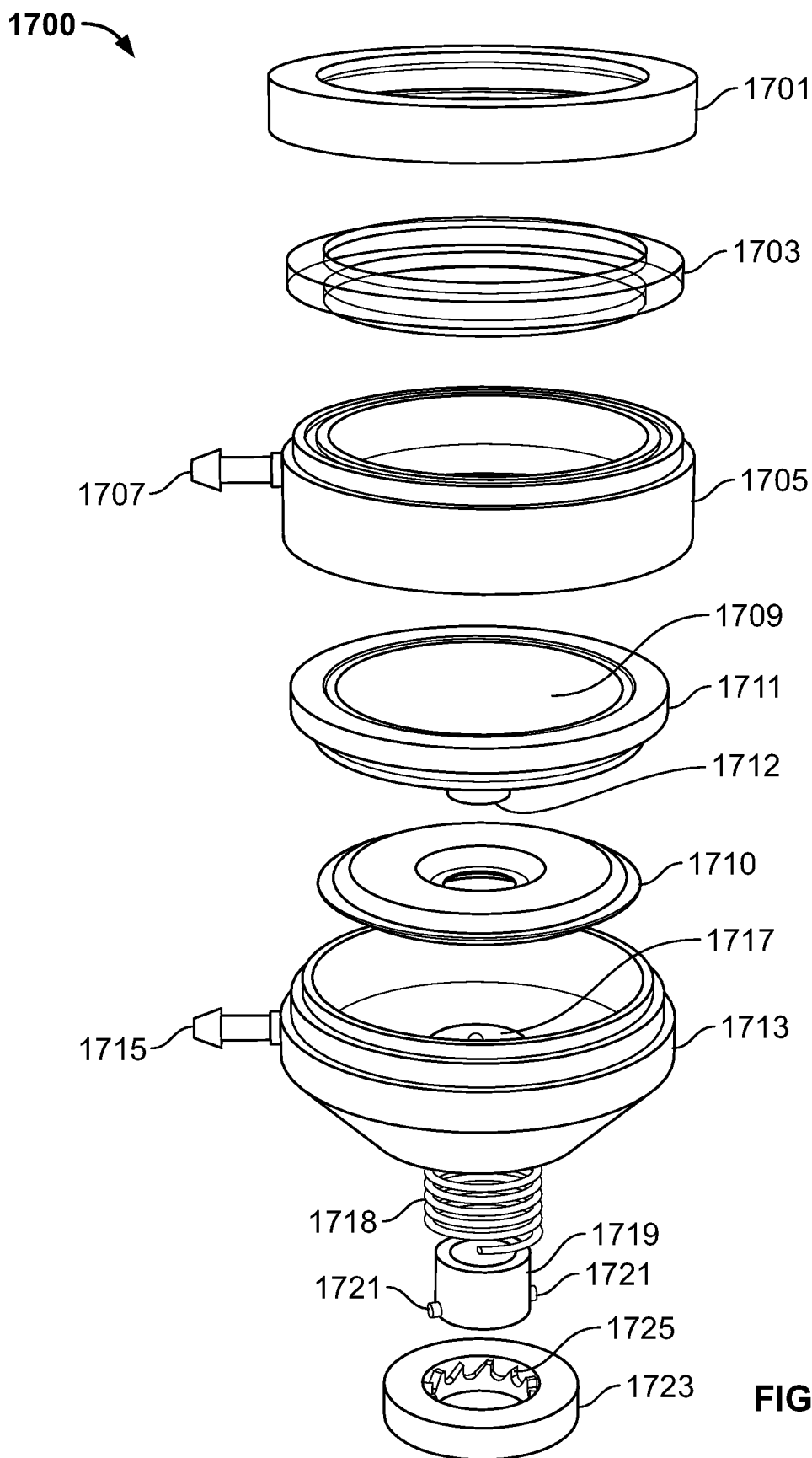
FIG. 17 shows illustrative apparatus in accordance with principles of the invention.

FIG. 17 shows exploded view 1700 of reservoir components. View 1700 includes retainer ring 1701.

Retainer ring 1701 may be positioned over septum 1703. Retainer ring 1701 may fluidly seal septum 1703 to housing 1705. Septum 1703 may be positioned over first housing 1705. First housing 1705 may define, at least in part, a first chamber of a reservoir. Fluid contents of the first chamber may be accessed using barb 1707.

View 1700 includes platform 1709. Platform 1709 may be moveable. Platform 1709 may translate within housing 1705. Platform 1709 may translate within housing 1713. Movement of platform 1709 may expand the first chamber. Movement of platform 1709 may contract the second chamber. Movement of platform 1709 may draw fluid into housing 1705 via barb 1707. Movement of platform 1709 may expel fluid from housing 1713 via barb 1715. Expelling fluid from housing 1713 may induce hydraulic pressure in a tubing connected to barb 1715. The hydraulic pressure may be directed by the tubing to inflate a balloon affixed to the tubing.

Platform 1709 may be encircled by sealing ring 1711. Sealing ring 1711 may prevent housing 1705 from mixing with fluid in housing 1713. Sealing ring 711 may fluidly seal a first chamber of the reservoir from a second chamber of the reservoir.

Platform 1709 includes extension 1712. Extension 1712 may fit into bore 1717. Extension 1712 and bore 1717 may center platform 1709 with respect to housing 1713. Extension 1712 and bore 1717 may maintain contact between sealing ring 1711 and an inner wall of housing 1713.

Extension 1712 may be configured to translate within bore 1717. Extension 1712 may translate within bore 1717 in response to pressure applied to platform 1709. For example, a needle that penetrates septum 1703 may apply pressure to platform 1709. The pressure may expand a first chamber of the reservoir and contract a second chamber of the reservoir.

Extension 1712 may translate within bore 1717 in response to pressure exerted by spring 1718. Spring 1718 may bias platform 1709 against septum 1703. For example, a needle that penetrates septum 1703 may apply pressure to platform 1709. In response to a decrease in pressure applied to platform 1709 by the needle, platform 1709 may be pushed toward septum 1703 by spring 1718.

Reservoir 1700 includes bladder 1710. Bladder 1710 may be filled with a fluid. The fluid may be water, saline or any suitable fluid. Bladder 1710 may be compressible. Bladder 1710 may be compressed by movement of platform 1709. Platform 1709 may compress bladder 1710 against a floor and/or inner wall of housing 1713.

Compression of bladder 1710 may expel fluid from bladder 1710. The expelled fluid may exit housing 1713 through barb 1715. The expelled fluid may pressurize a tube connected to barb 1715.

Reservoir 1700 includes bushing 1719. Bushing 1719 includes protrusions 1721. Protrusions 1721 may be configured to engage guide 1725 in washer 1723. Protrusions 1721 may be configured to engage teeth (not shown) in bore 1717. Protrusions 1721 may lock a position of platform 1709 with respect to septum 1703. Bushing 1719 may be configured to rotate about extension 1712.

Figure 18:
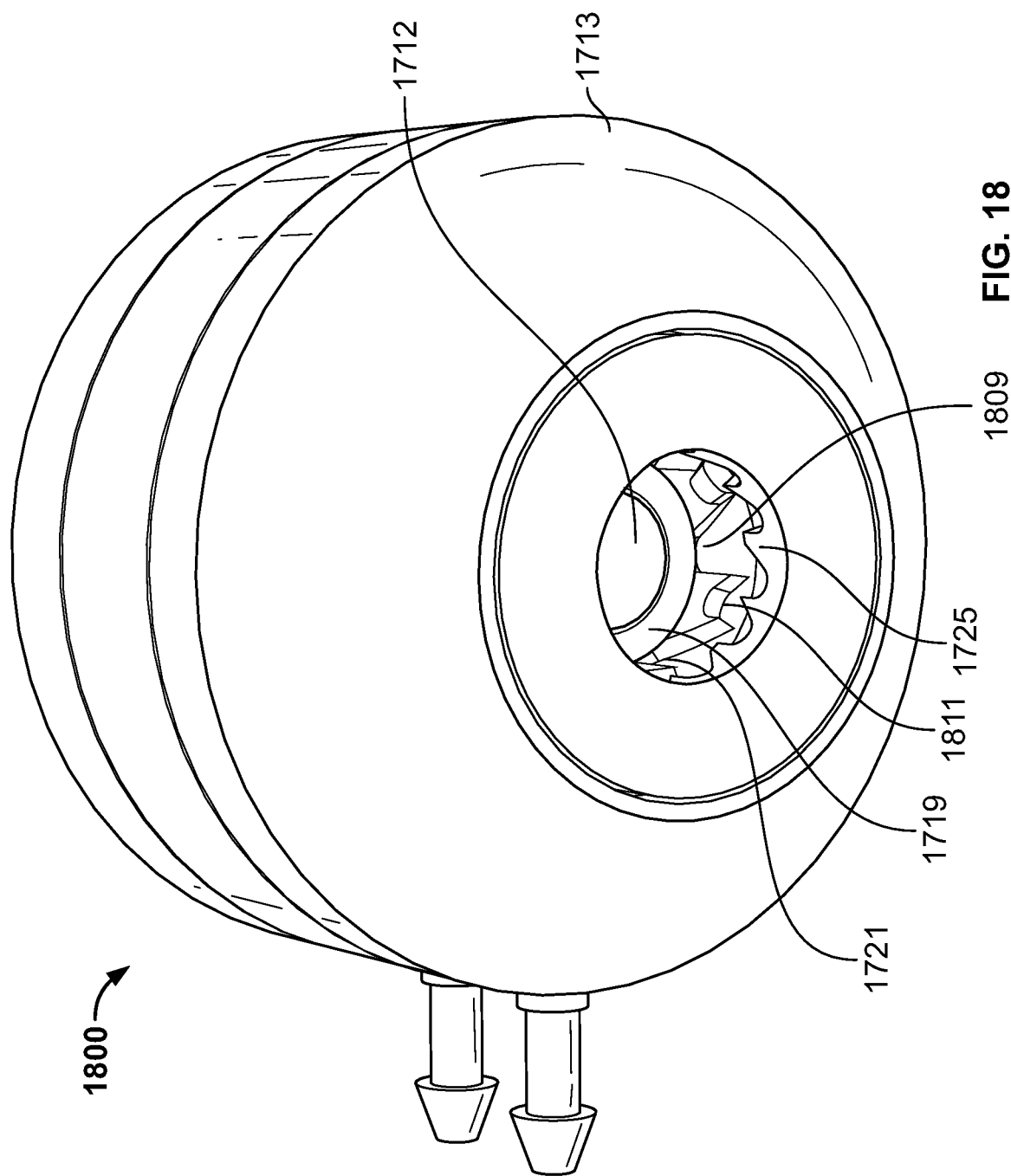
FIG. 18 shows illustrative apparatus in accordance with principles of the invention.

FIG. 18 shows illustrative view 1800 of reservoir 1700. View 1800 includes extension 1712. View 1800 shows bushing 1719. Busing 1719 includes protrusion 1721. Housing 1713 includes deep wells 1809 and shallow wells 1811. When protrusion 1721 is seated in a deep well, platform 1709 may be pressed against septum 1703. When protrusion 1721 is seated in a shallow well, platform 1709 may compress bladder 1710.

Protrusion 1721 may be moved from a deep well by pressure applied to platform 1709. For example, a needle inserted through septum 1703 may apply pressure to platform 1709. In response to the pressure, protrusion 1721 may be shifted from a deep well to a shallow well by guide 1725.

Figure 19:
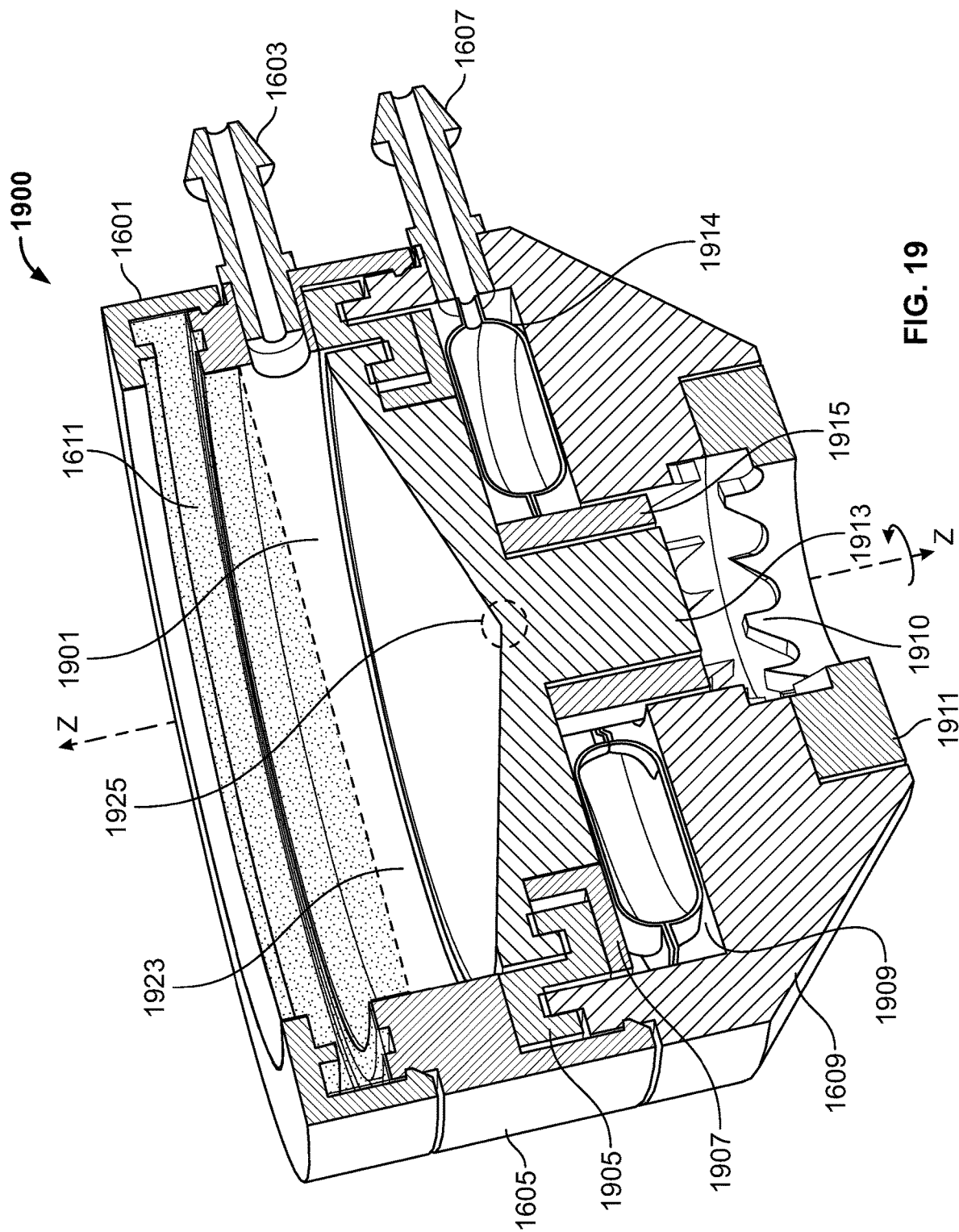
FIG. 19 shows illustrative apparatus in accordance with principles of the invention.

FIG. 19 shows illustrative cross-sectional view 1900 taken along lines 3-3 shown in FIG. 16. View 1900 includes septum 1611. Septum 1611 may be fluidly sealed to housing 1605 by retainer ring 1601.

Platform 1909 may receive a needle inserted through septum 1611 in depression 1925. The needle may push platform 1901 toward floor 1909 of housing 1609. Movement of platform 1901 may expand chamber 1923. Movement of platform 1901 may compress bladder 1914 against floor 1923.

Fluid may pool in chamber 1923. Fluid may be prevented from leaking out of chamber 1923 by a seal formed by septum 1611 and retainer 1601.

The fluid in chamber 1923 may include blood that enters chamber 1923 from a tubing (not shown) affixed to barb 1603. Barb 1603 may be inserted into a bore in housing 1605. Fluid in chamber 1923 may be prevented from leaking in to housing 1609 by seal 1905. Seal 1905 may be secured by retainer 1907. In some embodiments, platform 1901 may include retainer 1907.

View 1900 includes bladder 1914. Bladder 1914 may be filled with a liquid. Bladder 1914 may be compressed between platform 1901 and floor 1909 of housing 1609.

View 1900 shows extension 1913 of platform 1901. Extension 1913 may be configured to fit into bushing 1915. Bushing 1915 may include protrusions, such as protrusions 1721 of bushing 1719 (shown in FIG. 17). Bushing 1915 may rotate about axis Z when protrusions of bushing 1915 are shifted between deep wells and shallow wells of housing 1609. Movement of platform 1901 may shift the protrusions between deep and shallow wells.

In some embodiments, extension 1913 may include a flange. The flange may keep bushing 1915 fixed longitudinally along axis z with respect to extension 1913. The flange may allow bushing 1915 to rotate about axis Z in response to a shifting of the protrusion between deep and shallow wells.

View 1900 includes washer 1911. Washer 1911 includes guides 1910. Guides 1910 align a protrusion of bushing 1915 with a deep or shallow well of housing 1609.

When a protrusion of bushing 1915 is positioned in a deep well, bladder 1914 may expand to default size. When a protrusion of bushing 1915 is positioned in a shallow well, bladder 1914 may be compressed. When a protrusion of bushing 1915 is positioned in a shallow well, platform 1901 may be locked in a position that compresses bladder 1914. Pressure applied to platform 1901 may shift a protrusion of bushing 1915 into a deep well, unlocking platform 1901. When unlocked, a spring or other suitable biasing member (not shown) may push platform 1901 toward septum 1611 and contract chamber 1923.

In some embodiments, prior to unlocking platform 1901, chamber 1923 may be filled with fluid. The fluid within chamber 1923 may prevent platform 1901 from contacting septum 1611. For example, blood may pool in chamber 1923. The blood may be extracted from chamber 1923 during a dialysis procedure. At a conclusion of the dialysis procedure, hepranized saline may be injected into chamber 1923 and tubing affixed to barb 1603. The hepranized saline may prevent clots from forming in chamber 1923 and the tubing affixed to barb 1603.

Figure 20:
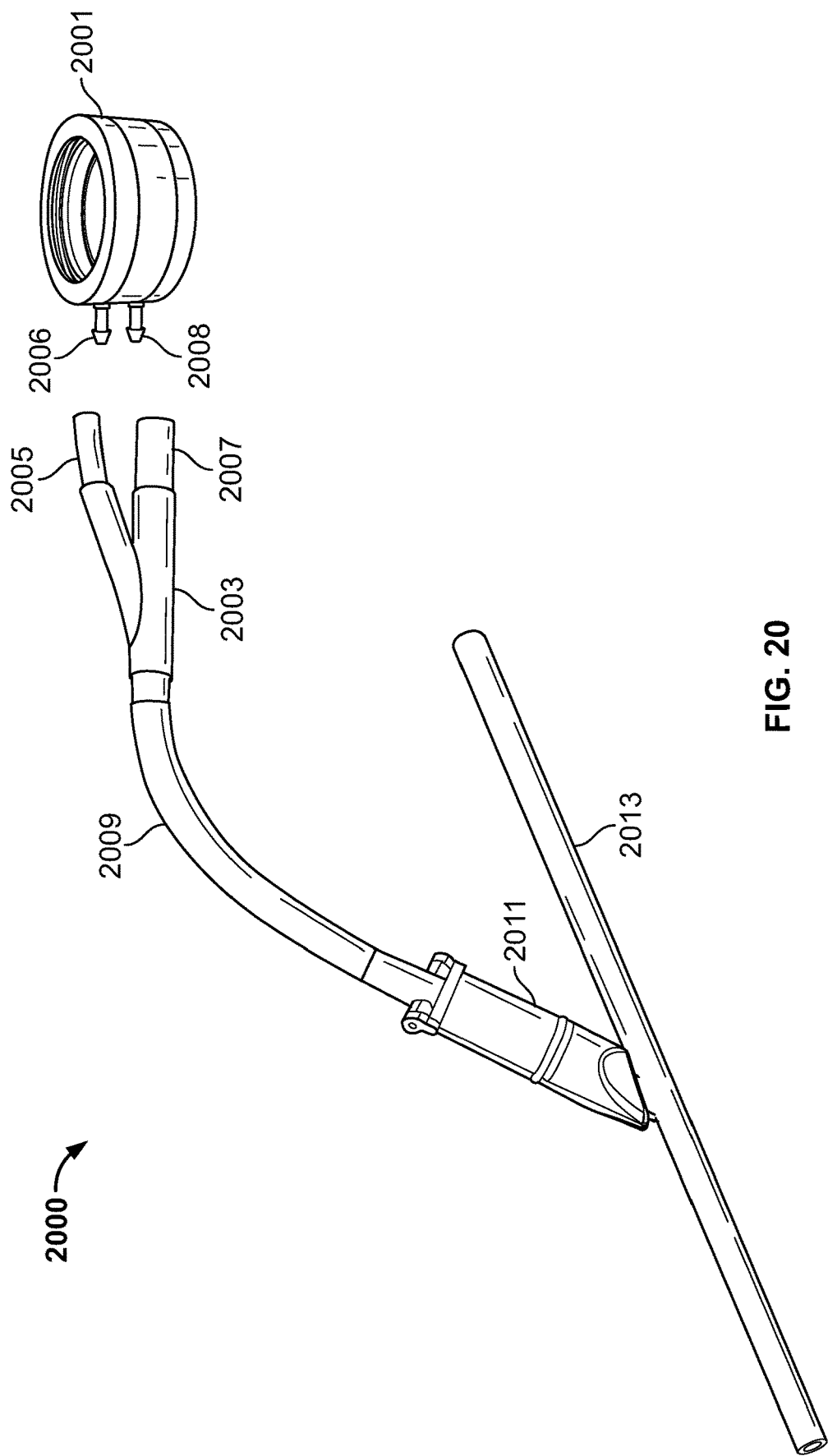
FIG. 20 shows an illustrative therapeutic scenario and associated apparatus in accordance with principles of the invention.

FIG. 20 shows illustrative system 2000. System 2000 includes clamp 2011. System 2000 includes tubing 2009. System 2000 includes adapter 2003. Adapter 2003 includes branch 2005 and branch 2007. Branch 2005 may be affixed to barb 2006 of reservoir 2001. Branch 2007 may be affixed to barb 2008 of reservoir 2001.

A needle may be inserted through a septum in reservoir 2001. The needle may apply pressure to a moveable platform within reservoir 2001 and thereby compress a bladder within reservoir 2001. Compression of the reservoir may expel fluid from the bladder into branch 2007 and tubing 2009.

The expelled fluid may inflate a balloon and open clamp 2011. Opening clamp 2011 may open a portion of tubing 2009 anastomized to conduit 2013. Opening clamp 2011 may allow blood or other fluid flowing within conduit 2013 to enter tubing 2009. The blood or other fluid may be drawn from conduit 2013 into tubing 2009. The blood or other fluid may flow through branch 2005 and into reservoir 2001. The needle may be used to extract the blood or other fluid from reservoir 2001. A system may include one or more of systems 2000.

Figure 21:
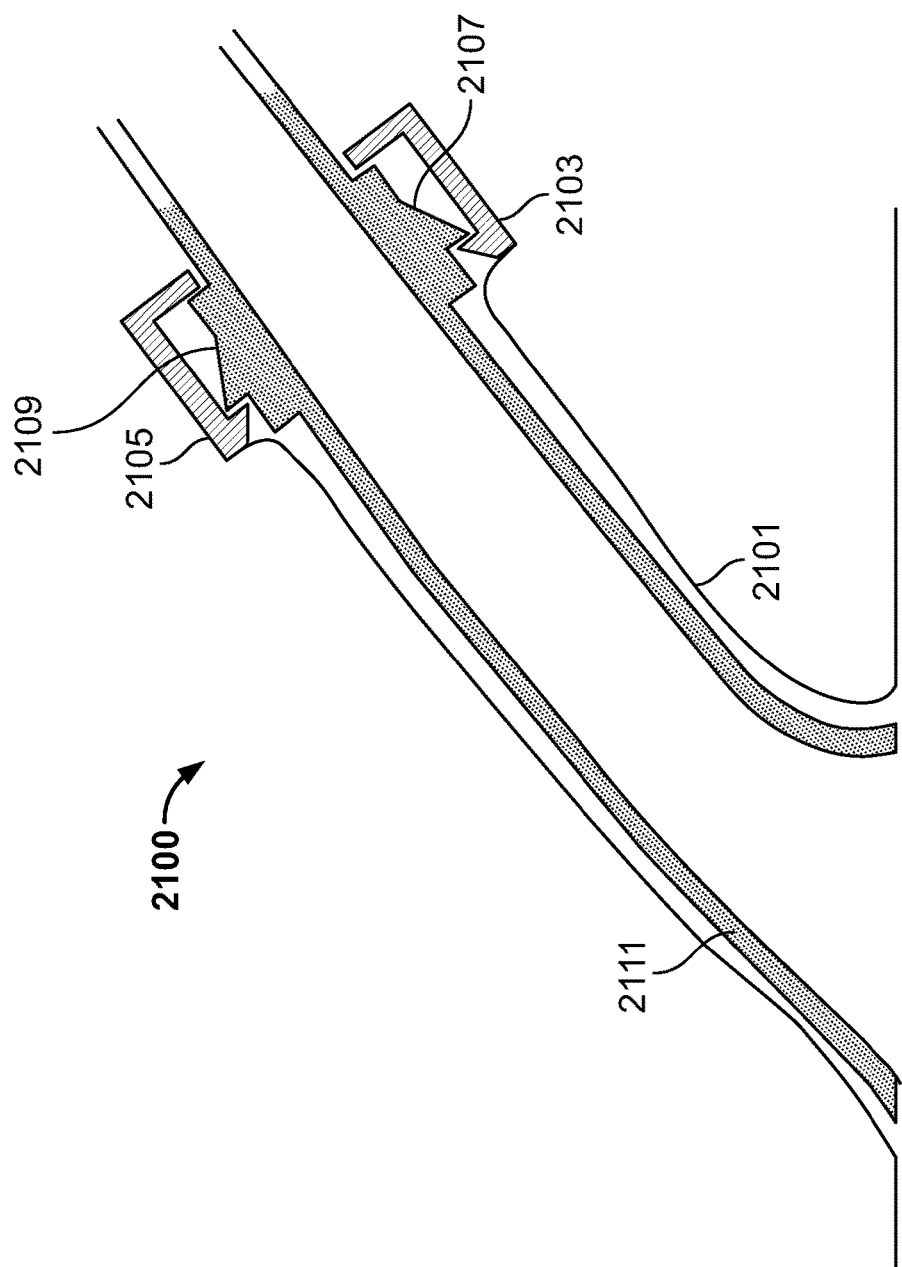
FIG. 21 shows an illustrative therapeutic scenario and associated apparatus in accordance with principles of the invention.

FIG. 21 shows illustrative apparatus 2100. Apparatus 2100 includes clips 2109 and 2107. Clips 2109 and 2107 are affixed to tubing 2111. Apparatus 2100 includes clamp 2101. Clamp 2101 includes clips 2103 and 2105. In some embodiments, tubing 2111 may be anastomized to a conduit. After the anastomization procedure, clamp 2101 may be slipped over tubing 2111 and positioned relative to the conduit. The clamp may be positioned abutting the conduit or near the conduit.

The clamp may be locked in a position relative to the conduit by engagement of clip 2103 of the clamp and clip 2107 of the tubing. The clamp may be locked in a position relative to the conduit by engagement of clip 2105 of the clamp and clip 2109 of the tubing. Some embodiments may only include one set of clips such as clips 2109 and 2105. Some embodiments may include two or more sets of clips.

Figure 22B:
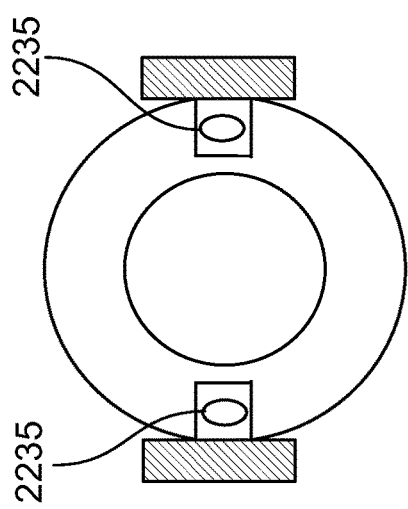
FIGS. 22A-22C show an illustrative therapeutic scenario and associated apparatus in accordance with principles of the invention.
Figure 22C:
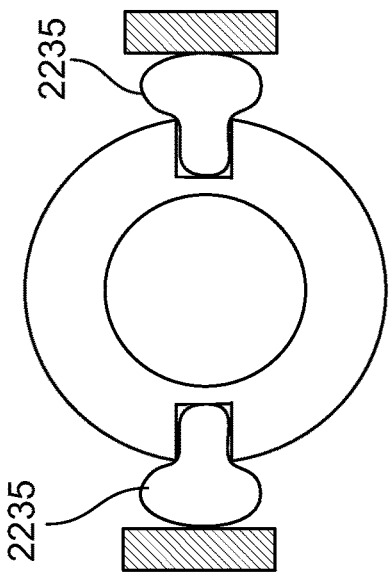
Figure 22A:
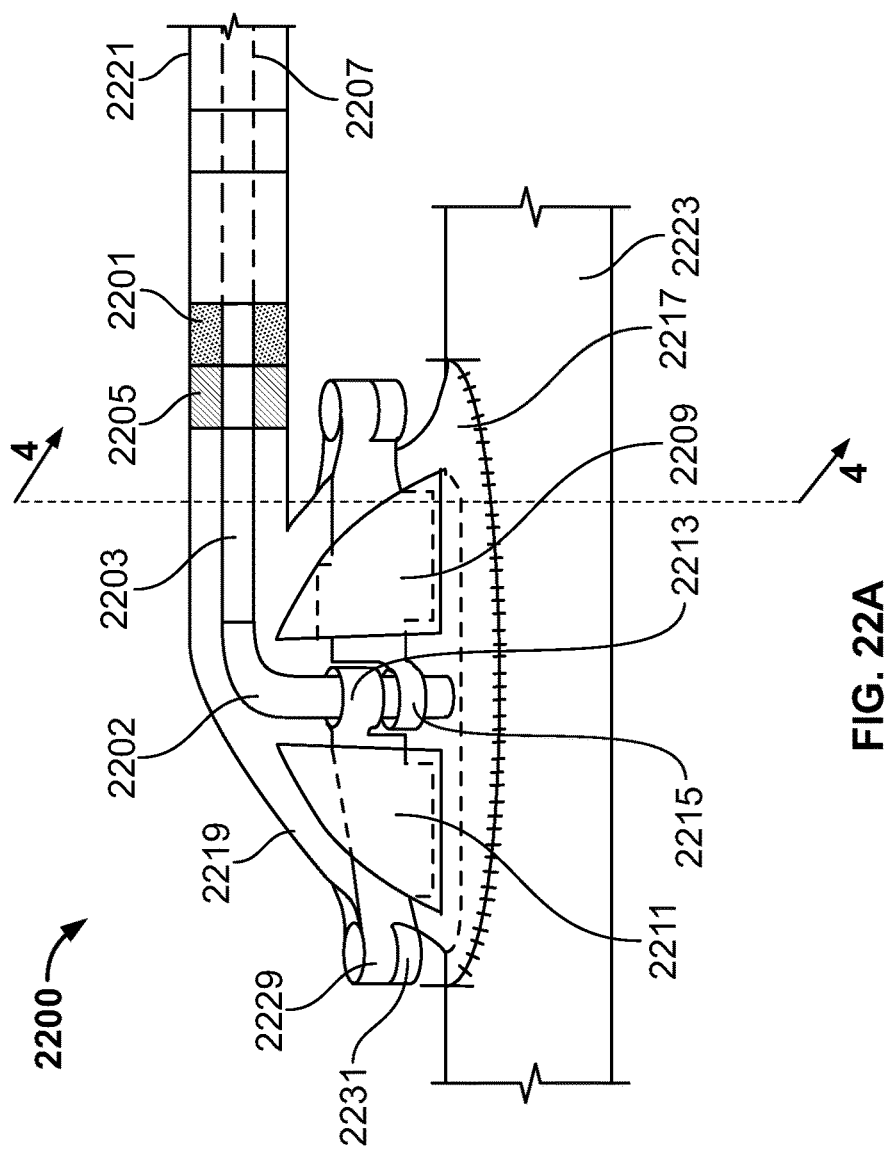

FIG. 22A shows illustrative apparatus 2200. Apparatus 2200 includes pocket 2201. Cantilever arm 2203 may be positioned inside pocket 2201. Pocket 2201 may position cantilever rod 2203 against tubing 2221. Apparatus 2200 includes annular ring 2205. Annular ring 2205 may press cantilever arm 2203 against tubing 2221. Tubing 2221 may include a non-compressible segment underneath annular ring 2205.

Tubing 2221 may include a compressing segment 2219. Pressing cantilever arm 2203 against compressible segment 2219 may close a lumen of tubing 2221. Closing the lumen of tubing 2221 may seal tubing 2221 from fluid flowing in conduit 2223.

Cantilever arm 2203 includes angled segment 2202. Angled segment 2202 may be fitted into hinges 2213 and 2215. Hinges 2213 and 2215 may be affixed to panels 2211 and 2209. In some embodiments, panels 2211 and 2209 may be inserted into a sleeve affixed to the anastomosis site. The sleeve may prevent components of apparatus 2200 from contacting bodily tissue. The sleeve may position cantilever arm 2203 and angled segment 2202 relative to tubing 2221 and/or conduit 2223.

Apparatus 2200 includes hydraulic tract 2207. Hydraulic tract may carry a hydraulic fluid such as water. Hydraulic tract 2207 may terminate in a balloon segment (not shown). The balloon segment may be inflated by increasing hydraulic pressure inside hydraulic tract 2207. The balloon segment may extend between tubing 2221 and annular ring 2205. The balloon segment may extend alongside tubing 2221 from annular ring 2205 to a junction of cantilever arm 2203 and angled segment 2202.

When the balloon segment is inflated, cantilever arm 2203 may push angled segment 2202 away from tubing 2221. Angled segment 2202 move away from tubing 2221 by rotating panels 2211 and 2209 about hinges 2213, 2215, 2225, 2227, 2229 and 2231. Pushing angled segment 2202 away from tubing 2221 may open a lumen in tubing 2221 placing tubing 2221 in fluid communication with contents of conduit 2223. Apparatus 2200 may include two or more cantilever arms and associated angled segments.

FIG. 22B shows an illustrative cross-section of apparatus 2200 taken along lines 4-4 when balloon segment 2235 is in a deflated state. FIG. 22C shows an illustrative cross-section of apparatus 2200 taken along lines 4-4 when the balloon segment 2235 is in an inflated state.

Figure 23A:
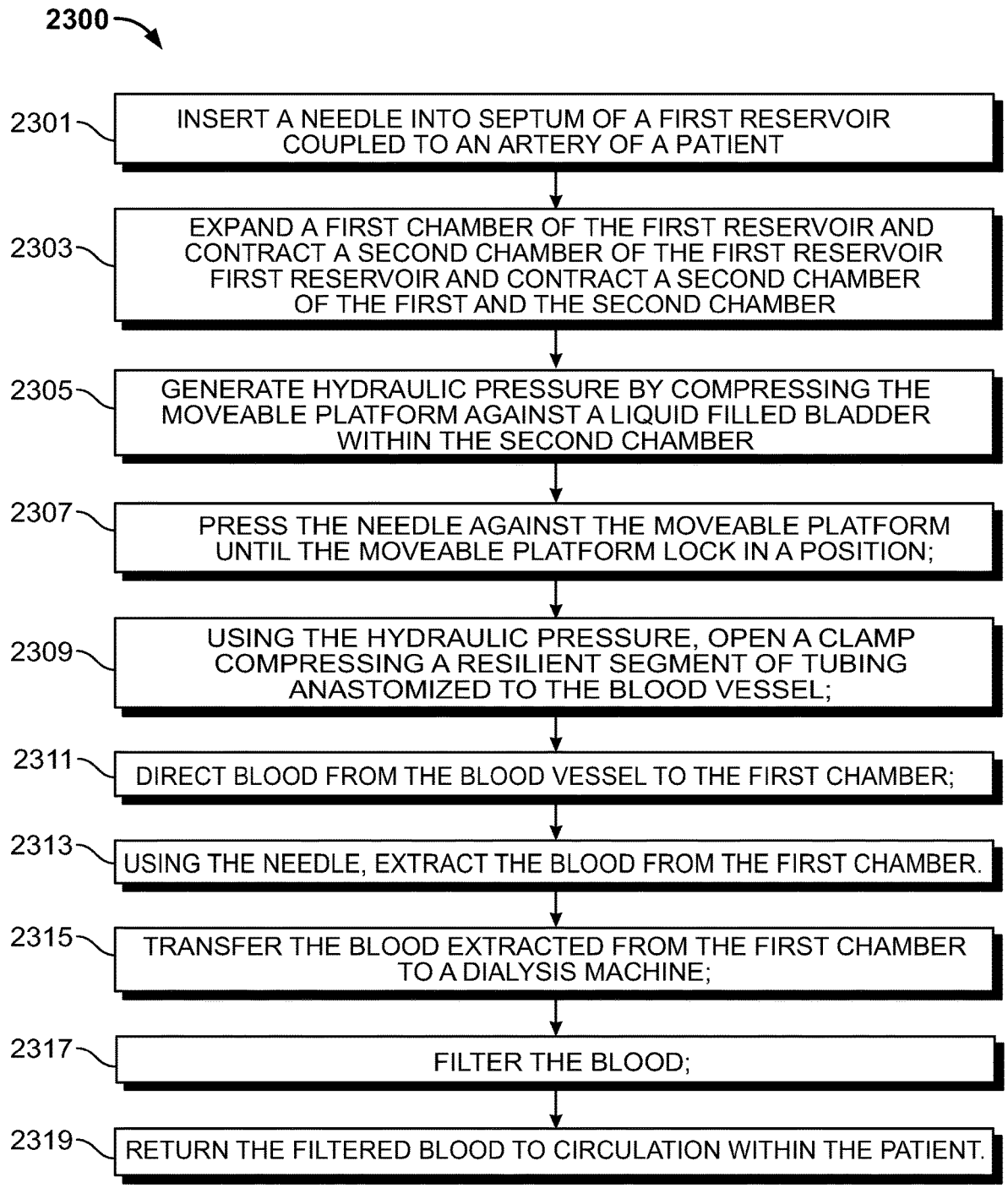
FIGS. 23A-23B show an illustrative process in accordance with principles of the invention.
Figure 23B:
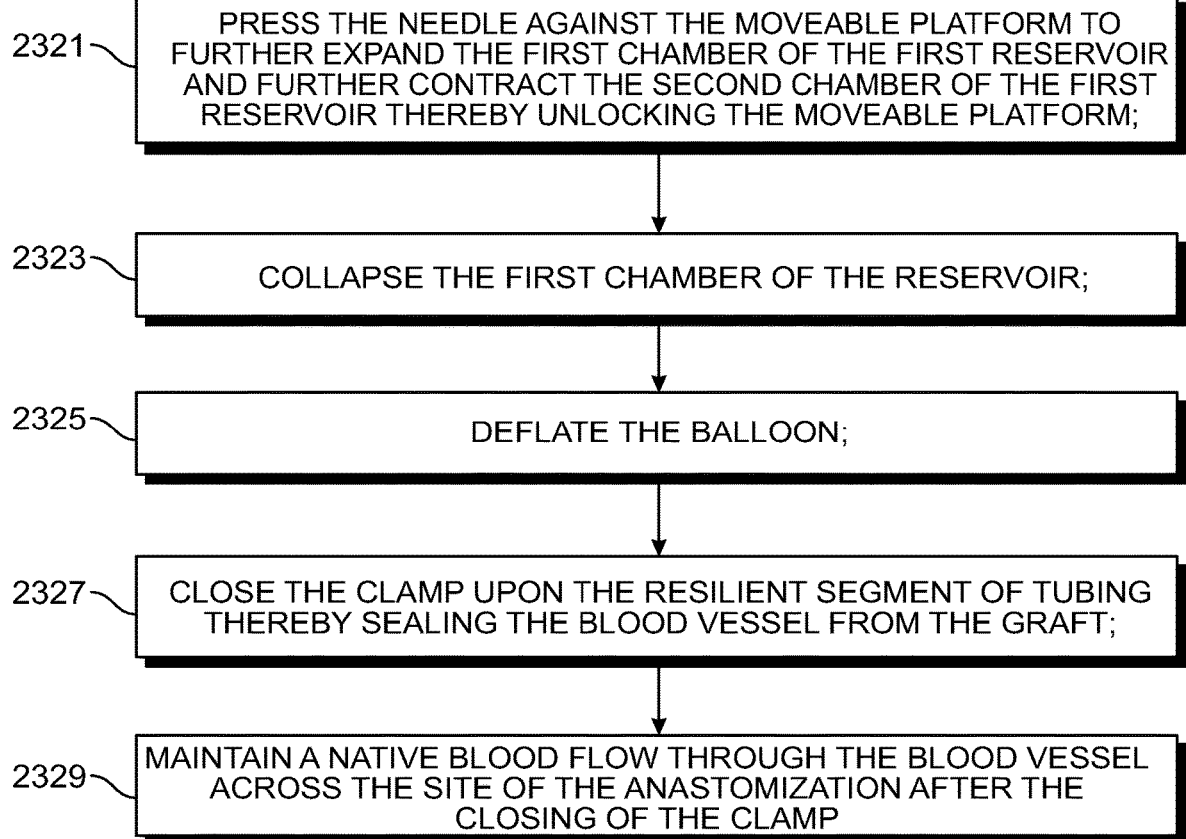

FIGS. 23A-23B show illustrative process 2300. For the sake of illustration, one or more of the steps of the process illustrated in FIG. 23 will be described as being performed by a "system." The "system" may include one or more of the features of the apparatus, arrangements information or processes shown in FIGS. 1-22 and/or any other suitable device or approach.

The "system" may be a computer or robotic system. For example, a subcutaneous reservoir may include circuitry for directing a robotically controlled needle into a septum of the reservoir. The system may provide automated dialysis of a patient's blood.

Process 2300 begins at step 2301. At step 2301, the system inserts a needle into septum of a first reservoir coupled to an artery of a patient. At step 2303, the system expands a first chamber of the first reservoir and contracts a second chamber of the first reservoir by pressing the needle against a moveable platform between the first chamber and the second chamber.

At step 2305, hydraulic pressure is generated by compressing the moveable platform against a liquid filled bladder within the second chamber. At step 2307, the system continues to press the needle against the moveable platform until the moveable platform locks in position compressing the bladder.

At step 2309, the hydraulic pressure opens a clamp that is biased to compress a resilient segment of tubing anastomized to the blood vessel.

At step 2311, blood begins to flow from the blood vessel into the first chamber. At step 2313, using needle, the system extracts blood from the first chamber. At step 2315, the system transfers the blood extracted from the first chamber to a dialysis machine. At step 2317, the system filters the extracted blood. At step 2319, the system transfers the filtered blood to a second reservoir. The first and second reservoir may be coupled to arteries, veins or any suitable combination of blood vessels. At step 2321, the system returns the filtered blood to circulation within the patient via hydraulically controlled access coupled to the second reservoir.

At step 2321, the system presses a needle against the moveable platform to further expand the first chamber of the first reservoir and further contract the second chamber of the first reservoir thereby unlocking the moveable platform. At step 2323, a biasing member of the reservoir collapses the first chamber of the reservoir. At step 2325, as a result of the expansion that second chamber, the bladder fills with fluid and decreases the hydraulic pressure allowing the balloon to deflate. At step 2327, the clamp closes upon a resilient segment of tubing thereby sealing the blood vessel from the graft. The clamp may be positioned to seal the tubing in a manner that preserves substantially uniform blood flow through the blood vessel across the site of the anastomization at step 2329.

Figure 24:
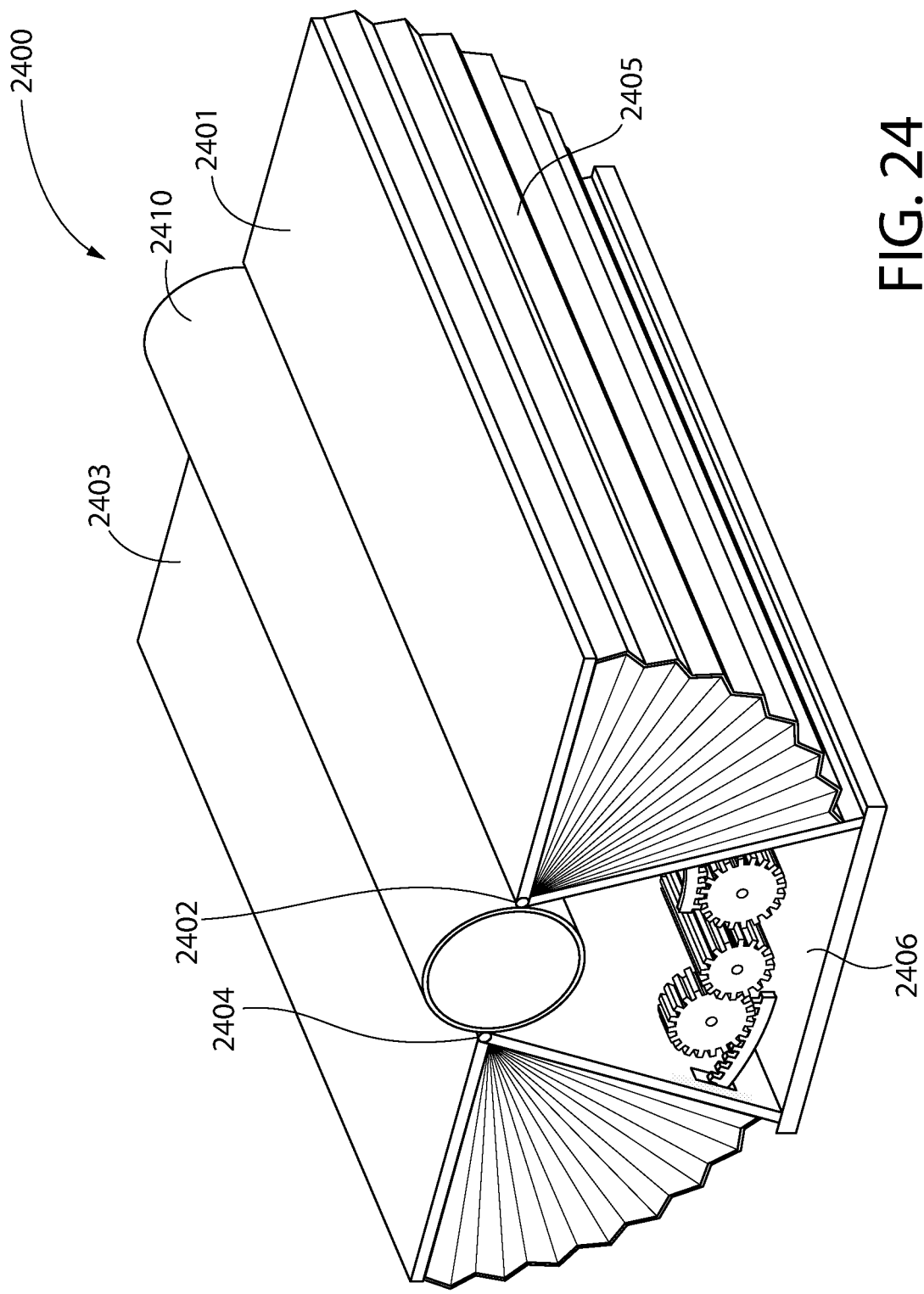
FIG. 24 shows illustrative apparatus in accordance with principles of the invention.

FIG. 24 shows an illustration of a clamp manipulator 2400, which alone or as a component of an overall lumen clamping means, comprises a first tab 2401 which may be rotatably attached to an axial support member 2402, and in a preferred embodiment contains a second tab 2403 which may also be rotatably attached to an axial support member 2404. There may be an elastic, or other suitable material, tab shield 2405 serving as a covering for the purpose of shielding the area traversed by said tabs 2401 and 2403. Additionally, the tab shield 2405 may serve to provide retractive forces, causing the tabs 2401 and 2403 to return to their initial position, following use. The tabs may be arranged to be coupled with, or to engage a gear assembly 2406.

This figure shows first tab 2401 and second tab 2403 as rectangular in primary shape, however, this shape is only for illustrative purposes to be able to clearly show the structure of the tab as well as the tab shield 2405. It can be appreciated by those skilled in the art, that the shape may well be a semicircle or an irregular parabolic-type of design with straying from the concept of this component disclosure; the ease of use, patient comfort, and ease of manufacture will lead to various satisfactory shapes contemplated by this disclosure.

Figure 25:
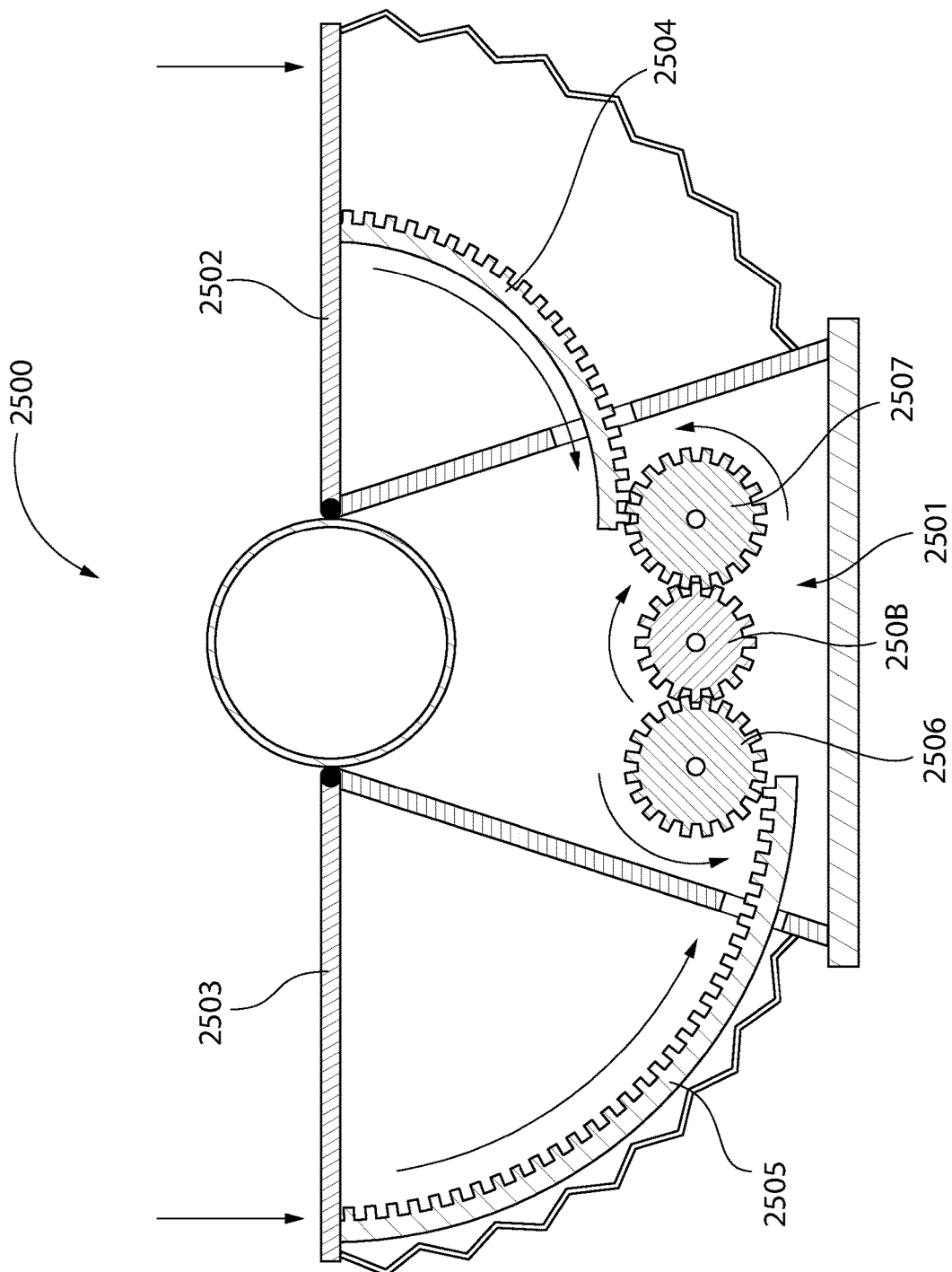
FIG. 25 shows illustrative apparatus in accordance with principles of the invention.

FIG. 25 shows an end view illustration of a clamp manipulator 2500, which may have one or more features of the clamp manipulator 2400 (shown in FIG. 24) and the gear assembly 2501, which may have one or more features of the gear assembly 2406 (shown in FIG. 24). The directions of pressing the first tab 2502 and the second tab 2503 can be seen. The tab may have a substructure suitable for the transfer of the tabs to the gear assembly 2501. In a preferred embodiment, the substructure may include an inner gear assembly 2504 or an outer gear assembly 2505, or both. Additionally, the gear assembly 2501 may have a left-side drive gear 2506 and a right-side drive gear 2507, arranged to take power from the outer gear assembly 2505 or the inner gear assembly 2504, or both. The left-side drive gear 2506 and right-side drive gear 2507 are both arranged to drive central gear 2508. This gear arrangement is meant to describe possible motion, and placement of power transfer mechanisms. Those skilled in the art can appreciate the various mechanisms and gear combinations that might achieve this basic goal, and those embodiment are intended to be encompassed in this disclosure.

Figure 26:
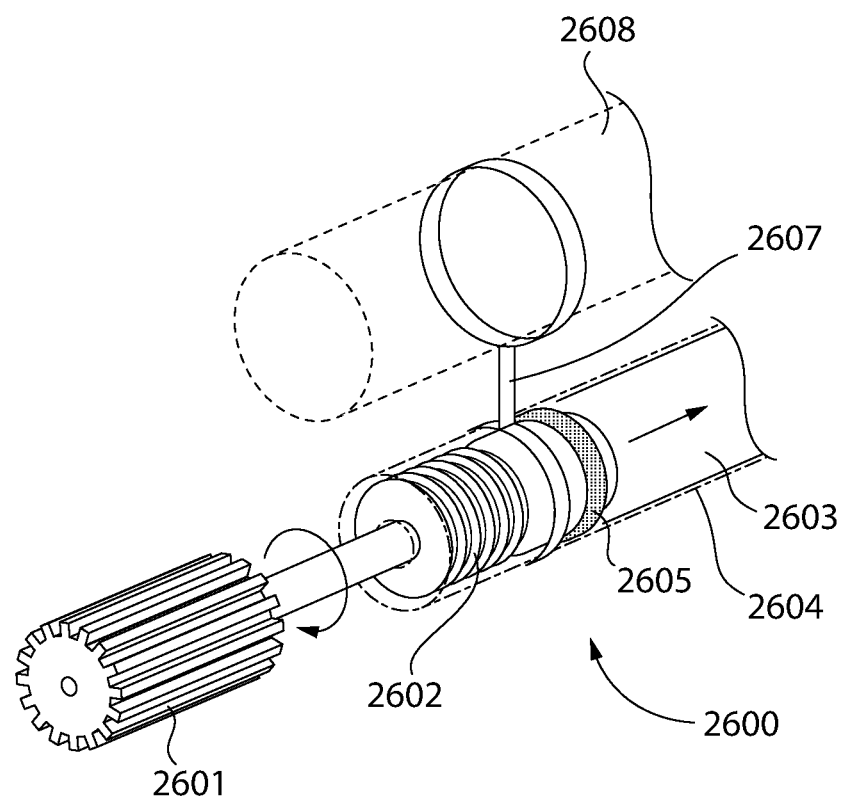
FIG. 26 shows illustrative apparatus in accordance with principles of the invention.

FIG. 26 shows an illustration of a fluid driven member 2600, which may have one or more features of the clamp manipulator 2500 (shown in FIG. 25). Specifically, a central gear 2601 is arranged (similarly to central gear 2508, shown in FIG. 25) to drive or otherwise energize the fluid driven member 2600. The central gear 2601 is arranged in a preferred embodiment to couple with a longitudinal screw gear 2602, wherein the longitudinal screw gear 2602 acts on the pressurized fluid 2603 contained in said fluid housing tube 2604. The pressure is modulated by the movement of a plunger 2605, or other moveable sealing apparatus. The structure of the assembly may be reinforced through components such as central cross-member 2607; such central cross member 2607 may be affixed to the device lumen 2608 (see 2410, for example; in FIG. 24).

Figure 27A:
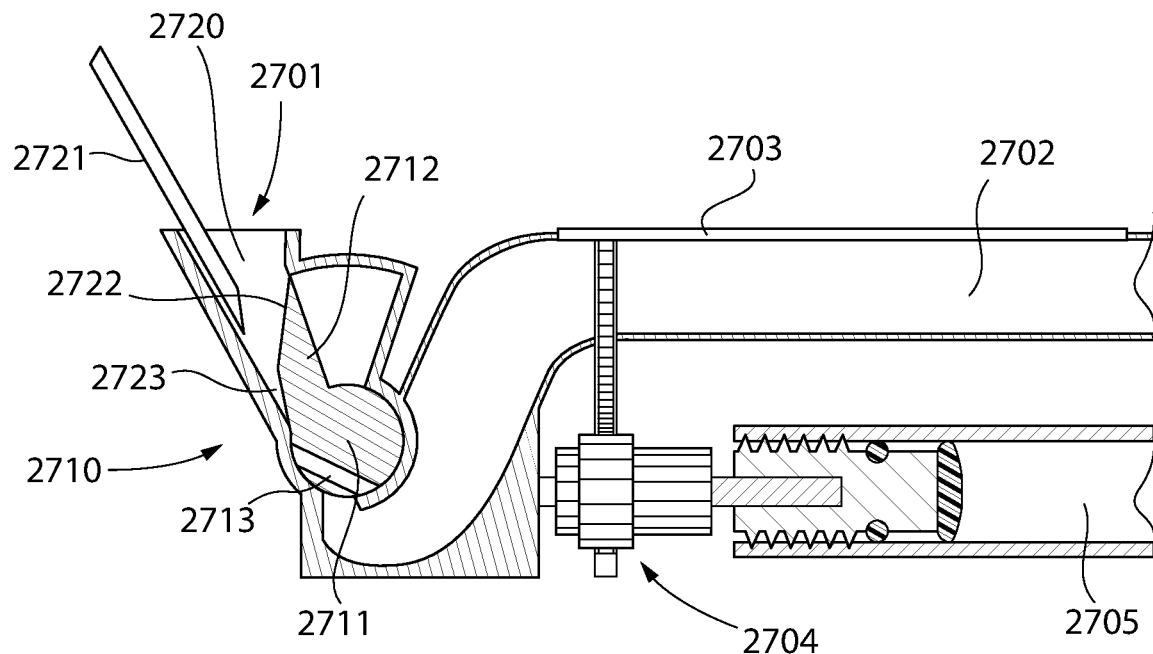
FIGS. 27A-27B show illustrative apparatus in accordance with principles of the invention.

FIG. 27A shows an illustration of the needle receptor 2701 coupled with the device lumen 2702, wherein the device lumen is shown traversing the tabs 2703 (see the similar tabs also at number 2401 and 2403, in FIG. 24; and tabs also at number 2502 and 2503, in FIG. 25) and the tabs are coupled to the gearing means 2704 (see also the similar gearing means at number 2406, in FIG. 24) which is in-turn coupled to the fluid driven member 2705 (see also the fluid driven member 2600, in FIG. 26). This embodiment may contain one or more features of each of these referenced figures and the embodiments related thereto.

Additionally, this embodiment shows the needle receptor 2701 with its positioning means 2710 component. The positioning means 2710 includes in a preferred embodiment, a rotating member 2711 which in-turn has an angular protrusion 2712 and a channel 2713. The needle receptor 2701 has a funnel-shaped entry site 2720, which is wide enough to provide a broad zone for a successful needle stick. Once the needle 2721 is passed through the skin and into the funnel-shaped entry site 2720 it is guided as it progresses toward the angular protrusion 2712. The surface that engages the needle 2721 first upon a nearly perpendicular (a high angle with the skin surface) may include an irregularity in the form of a sloping inclination 2722, this irregularity serves to direct the needle 2721 toward the conic-base of the funnel-shaped entry site 2720. Following the leading edge of the angular protrusion 2712, the needle next encounters a channel directing detente 2723. This detent 2723 serves the further guide the needle into the channel 2713 by causing a slight rotation of the rotating member 2711; thereby ensuring that the tip of needle 2721 will intersect the channel 2713 opening.

Once the needle 2721 begins to enter the channel 2713, the needle 2721 causes the continued rotation of the rotating member 2711. At the instance of near total alignment of the needle 2721 with the channel 2713, the needle 2721 will slide into the tight-fitting channel 2713; thereby causing a friction fit seal. It is also contemplated that coatings, sealing agents, and dissimilar materials (these various additions are not shown here) may be beneficial to this sealing action, and they are within the contemplation of this disclosure.

Figure 27B:
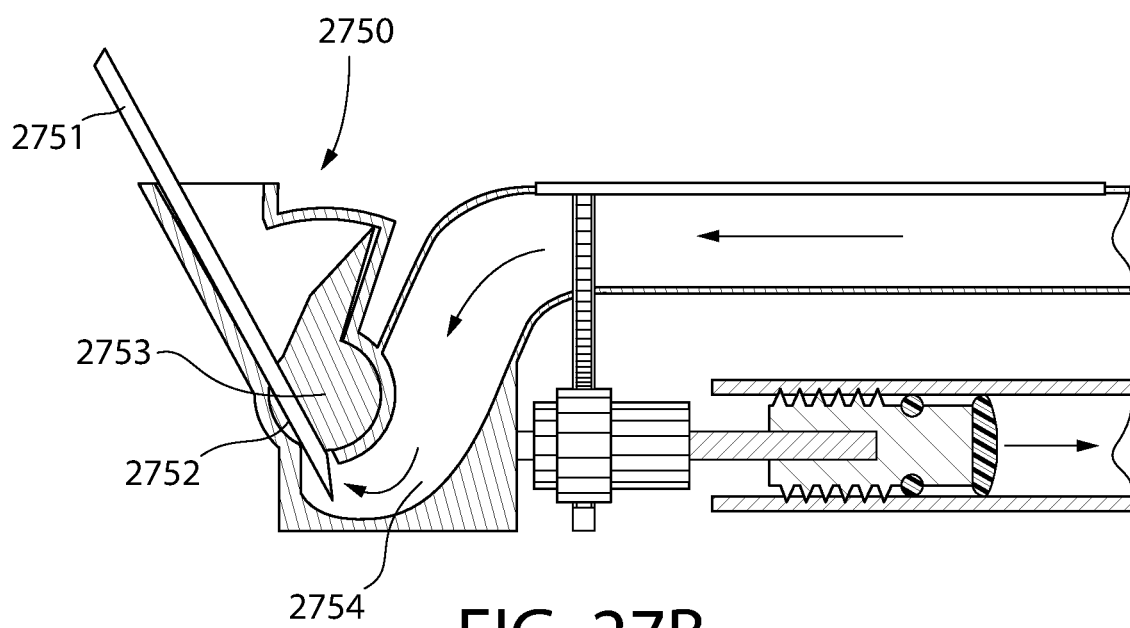

FIG. 27B shows an illustration of the needle receptor 2750, which may have one or more features of the needle receptor 2701 (shown in FIG. 27A). This illustration shows the needle 2751 after it has come into alignment with the channel 2752 following the rotation of the rotating member 2753. The needle 2751 is in fluid communication with the device lumen 2754. In this position the needle 2751 should be in substantial contact with the channel 2752, such that there is no fluid leakage from the device lumen 2754.

Figure 28:
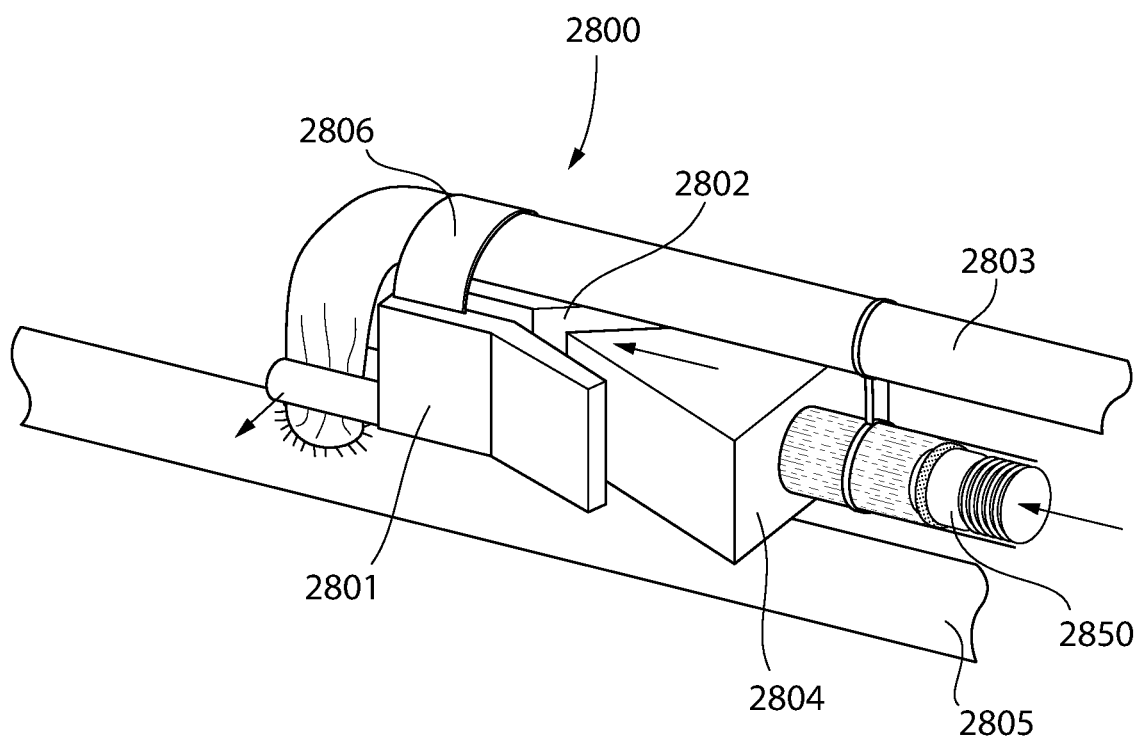
FIG. 28 shows illustrative apparatus in accordance with principles of the invention.

FIG. 28 shows an illustration of the lumen clamping means 2800. This illustration shows a first clamp arm 2801 acting in concert with a second clamp arm 2802, to compress a device lumen 2803. The device lumen 2803 is released from the first clamp arm 2801 and the second clamp arm 2802, and open to flow from the native lumen 2805, as the wedge member 2804 is pressed between the first clamp arm 2801 and the second clamp arm 2802. The wedge member 2804 is driven by the fluid driven member 2850. The fluid driven member 2850 may have many of the characteristics and elements of fluid driven member 2600 (see FIG. 26).

Figure 29:
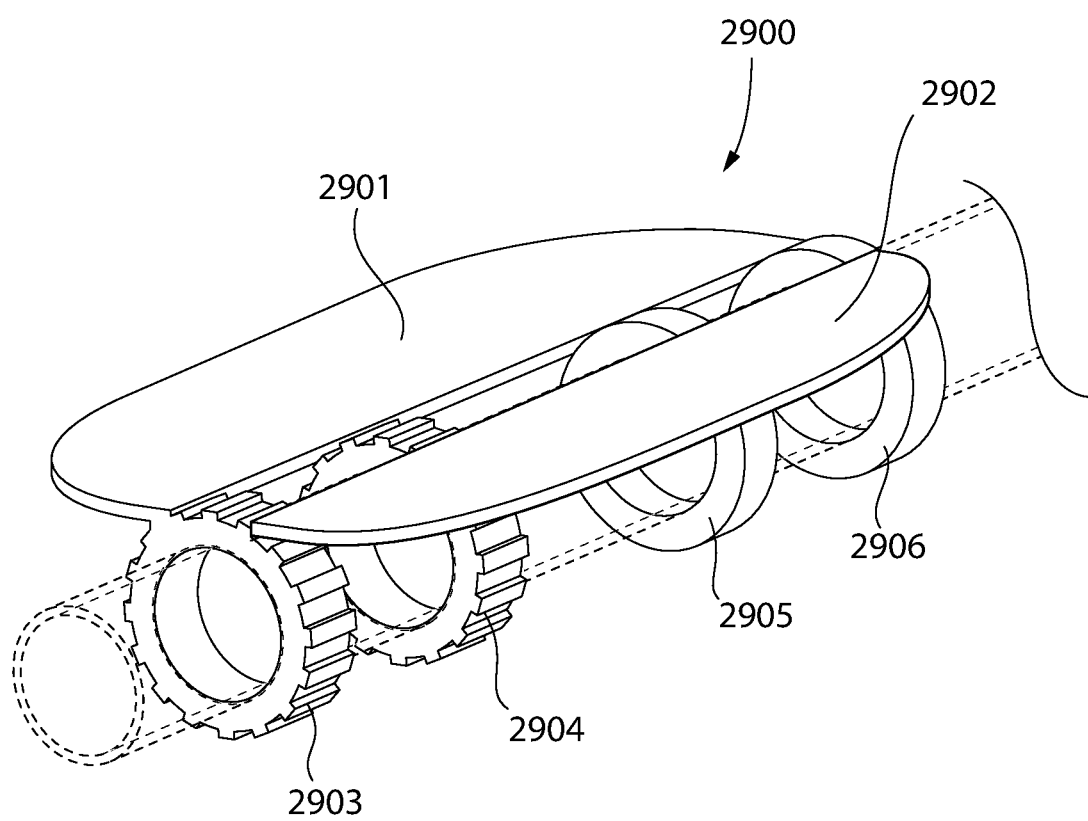
FIG. 29 shows illustrative apparatus in accordance with principles of the invention.

FIG. 29 shows an illustration of a preferred embodiment of a clamp manipulator 2900. This clamp manipulator may have many features and characteristics of clamp manipulator 2400 (see FIG. 24).

This clamp manipulator 2900 may be activated by pressing tab 2901 simultaneously with tab 2902. A first external ring-gear 2903 is coupled with tab 2901 (coupling is not shown) such that the angular motion of tab 2901 is translated as circular motion of said first external ring-gear 2903. Similarly, second external ring-gear 2904 is coupled with tab 2902 (coupling is not shown) such that the angular motion of tab 2902 is translated as circular motion of said second external ring-gear 2904. A gearing mechanism is arranged to combine the power of said first external ring-gear 2903 with the power of said second external ring-gear 2904 (not shown). A follower ring 2905 may be used to support the tab 2901 at the end opposite from external ring-gear; similarly, a follower ring 2906 may be used to support the tab 2902 at the end opposite from external ring-gear 2904.

Figure 30A:
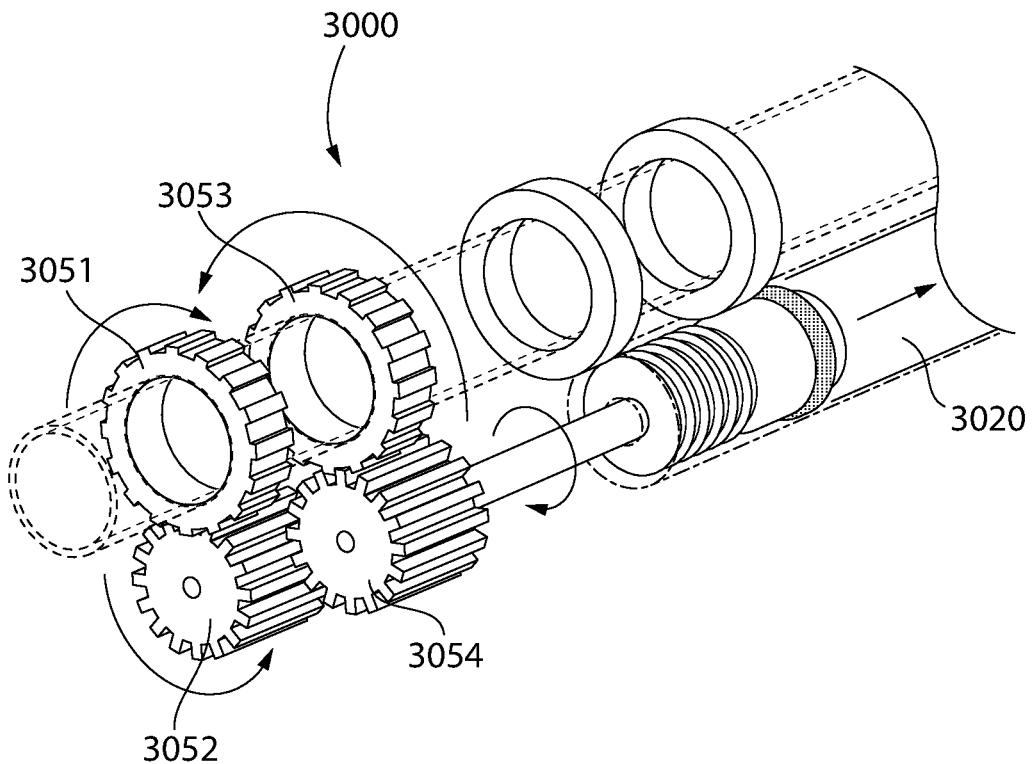
FIGS. 30A-30B show illustrative apparatus in accordance with principles of the invention.

FIG. 30A shows an illustration of the gear means 3000. The gear means 3000 may share one of more features of the first external ring-gear 2903 and the second external ring-gear 2904 (shown in FIG. 29). This gear means 3000 is arranged to transfer power from the tabs (not shown) to the fluid driven member 3020. This energy transfer is accomplished via the rotation of first external ring-gear 3051 and the second external ring-gear 3053, because of the orientation with the tabs (not shown, but see FIG. 29) the first external ring-gear 3051 and the second external ring-gear 3053 rotate in opposite directions. The rotative power becomes cumulative after the first external ring-gear 3051 and the second external ring-gear 3053 mesh with the slave gear 3052 and the primary drive gear 3054, respectively; whereupon the slave gear 3052 further meshes with the primary drive gear 3054. Thus, the power is cumulated by the gear means 3000 and delivered to the fluid driven means 3020.

Figure 30B:
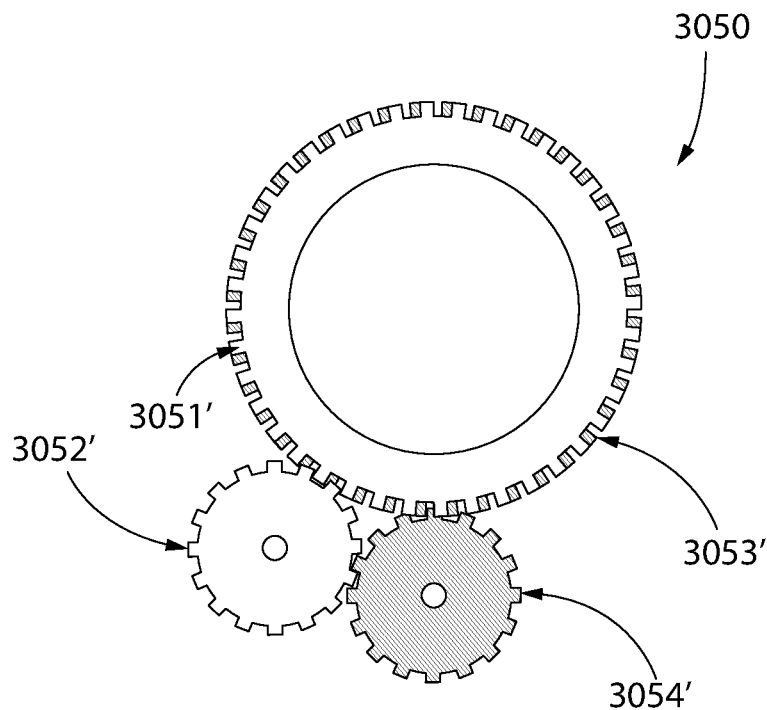

FIG. 30B shows an end-view illustration of the gear means 3050. This illustration repeats many elements of FIG. 30A, for the purposes of general illustration as well as a clarification of the spatial relationship of the individual component gears and their interactions. Elements depicting the same component are numbered the same as in FIG. 30A, however a prime indicator has been added to enable continuity from figure to figure while having a distinction. This view shows clearly the meshing of the first external ring-gear 3051' with the slave gear 3052'; this view together with the view of the slave gear 3052 (see FIG. 30A) demonstrates that the slave gear 3052' does not contact or mesh with the second external ring-gear 3053. However, this figure demonstrates that the slave gear 3052' does mesh with the primary drive gear 3054'; which primary drive gear 3054' does mesh with the second external ring-gear 3053.'

Figure 31:
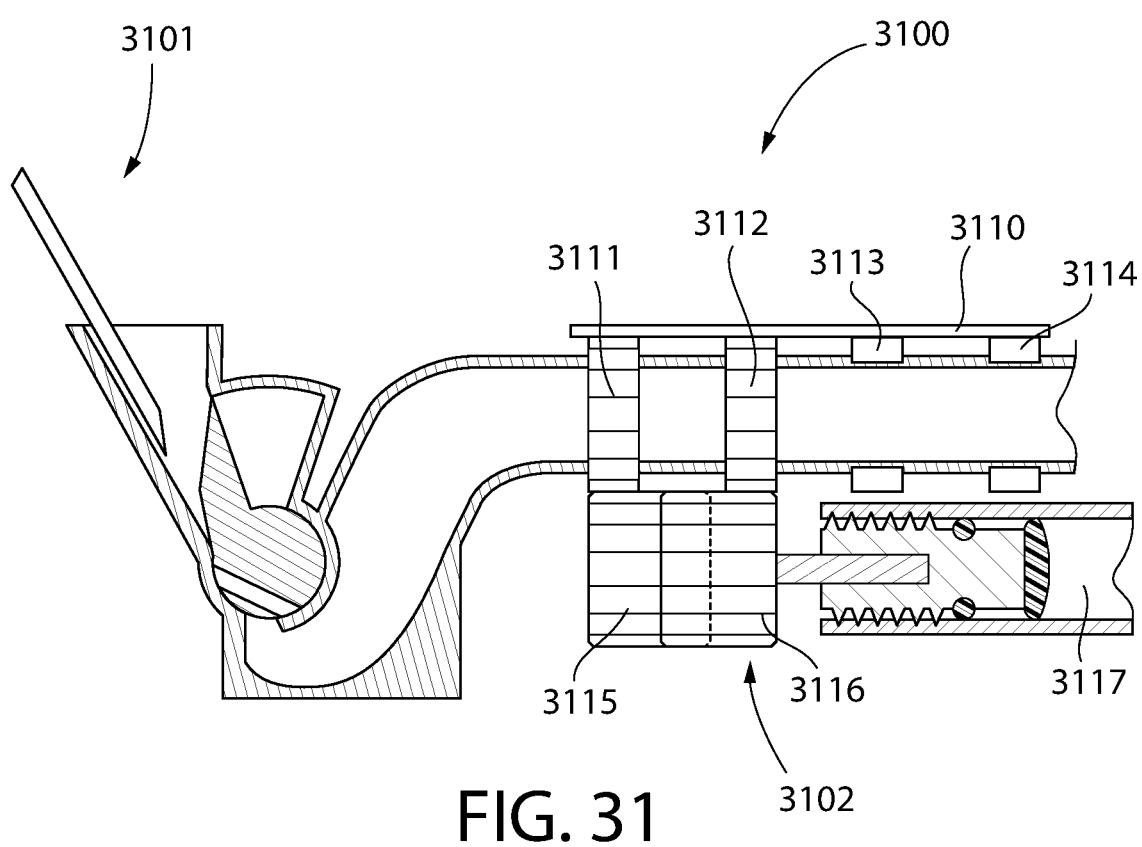
FIG. 31 shows illustrative apparatus in accordance with principles of the invention.

FIG. 31 shows an illustration of the needle receptor 3101, the clamp manipulator 3100, and the portion of the clamp manipulator 3100 referred to in certain embodiments as the gear means 3102 (see, for example, element 3000, at FIG. 30A, and element 3050, at FIG. 30B); the clamp manipulator repeats many features and characteristics of these referenced elements. This figure demonstrates the configuration of assembly and interrelatedness of the clamp manipulator 2900 (see FIG. 29) with the gear means 3000 (see FIG. 30A and FIG. 30B) and how they perform together to drive the fluid driven member 3020 (see FIG. 30A). The tab 3110 can be seen relative to first external ring-gear 3111, which transfer the downward force from the fingers of the operator (not shown); which will travel to the slave gear 3115, and then to the primary drive gear 3116. The primary drive gear also receives force from the second external ring-gear 3112, which is transferred unto it from the second tab (not shown, but see tab 2901 and tab 2902, at FIG. 29). This cumulative power is delivered from the gear means 3102 to the fluid driven tube 3117 (see for example element 2600, at FIG. 26).

Figure 32:
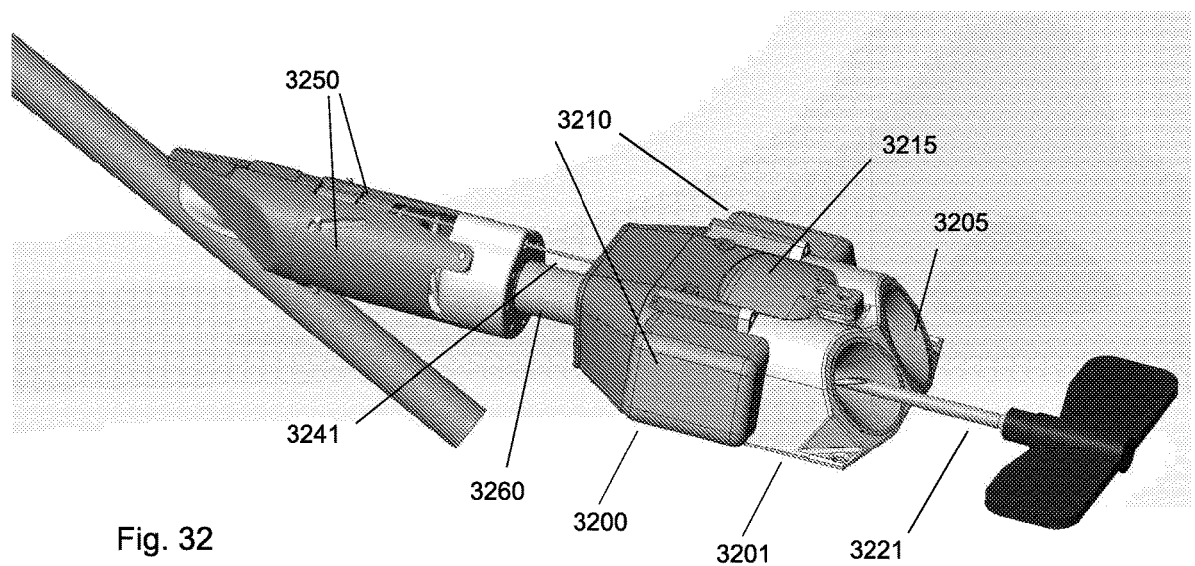
FIG. 32 shows illustrative apparatus in accordance with principles of the invention.

FIG. 32 shows an illustration of the needle receptor 3201 having a funnel opening 3205, the clamp manipulator 3200, and the portion of the clamp manipulator referred to in certain embodiments as the one or more tabs 3210, the palpable button 3215. This figure also shows the needle 3221, in place for insertion into the funnel opening 3205. Also depicted are tension element 3241 connected to clamp arms 3250 configured to clamp the lumen 3260 at a point adjacent to the anastomosis with the blood vessel.

Figure 33:
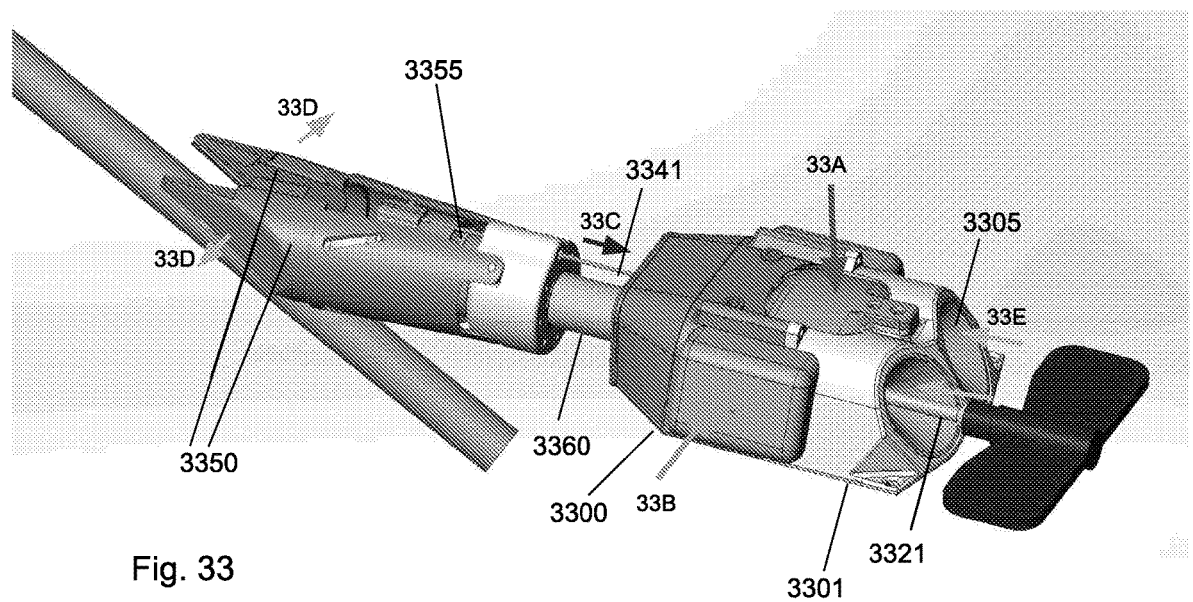
FIG. 33 shows illustrative apparatus in accordance with principles of the invention.
Figure 34:
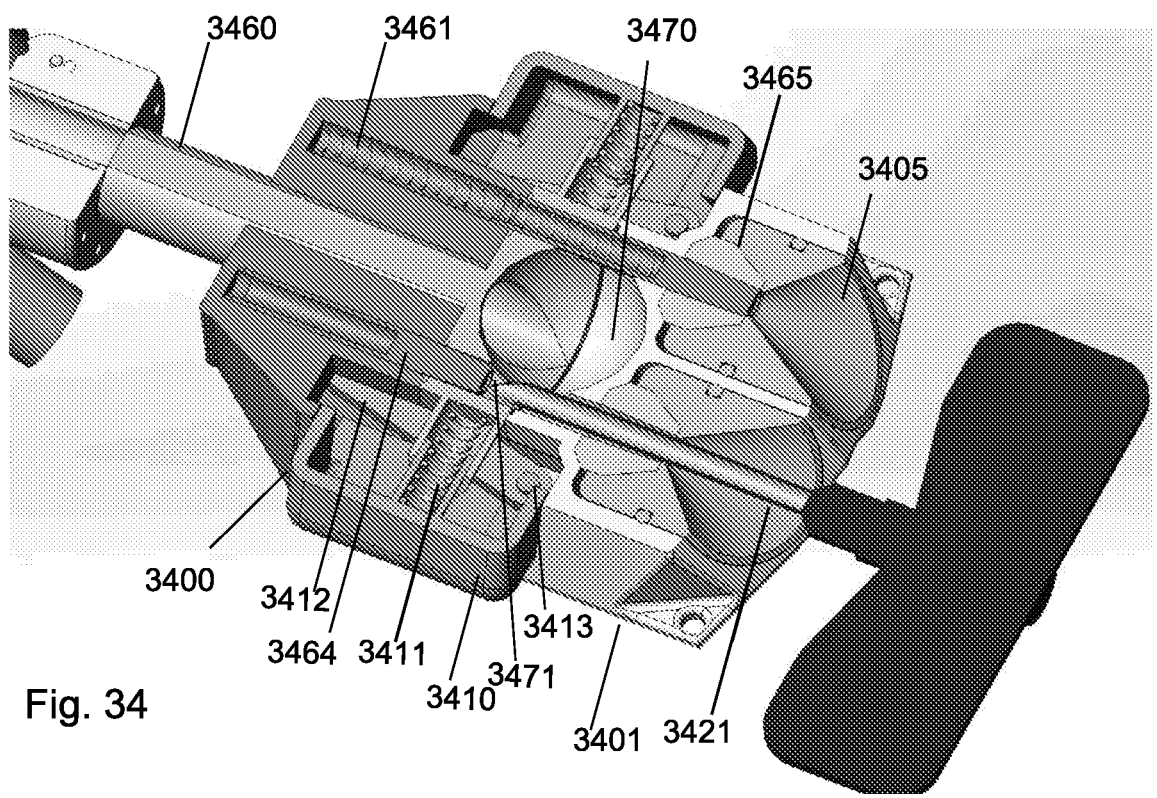
FIG. 34 shows illustrative apparatus in accordance with principles of the invention.
Figure 37:
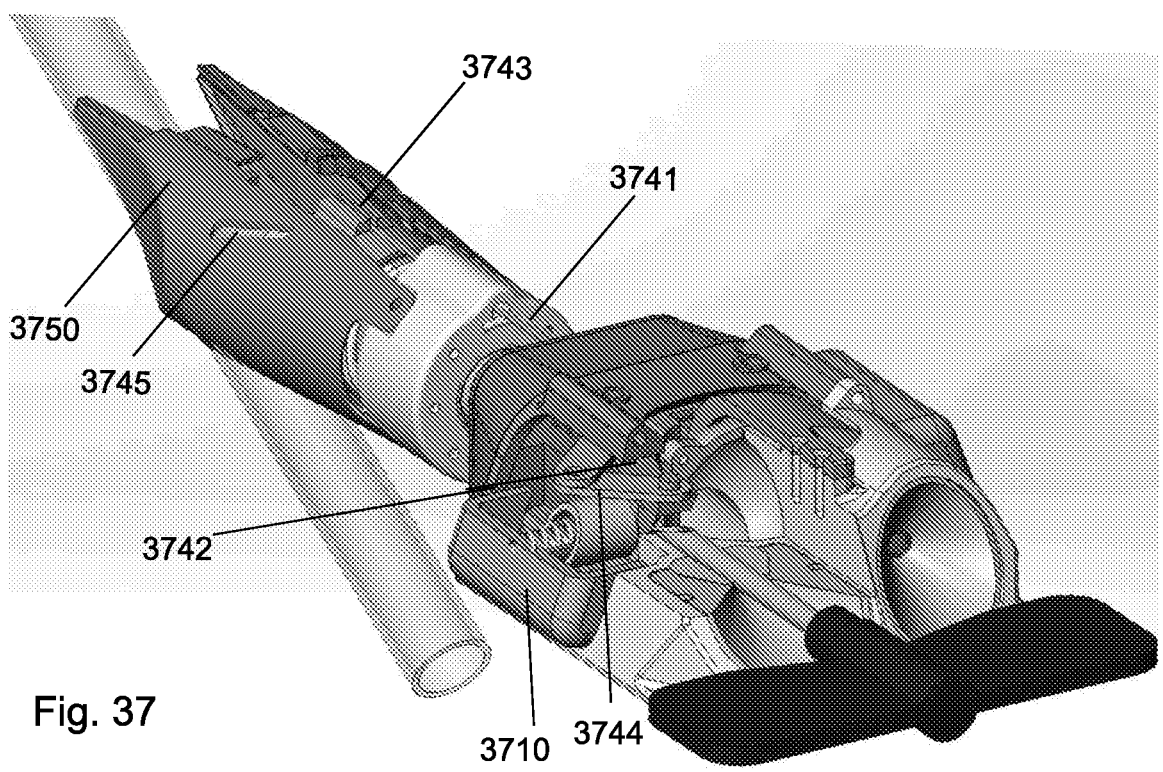
FIG. 37 shows illustrative apparatus in accordance with principles of the invention.

FIG. 33 depicts the needle 3321 having been advanced into the needle receptor 3301 through the funnel portion 3305. With the needle inserted into the needle receptor 3301, the palpable button 3315 may be depressed in the direction indicated by arrow 33A, so that the palpable button is moved from a first state to a second state. When the button 3315 is in a first state, it is configured to mechanically prevent movement of one or more tabs 3310. However, once button 3325 is in a second state, the one or more tabs 3310 may then be actuated by pressing in the tab, as represented by arrow 33B. In embodiments having two tabs on opposing sides of the clamp manipulator 3300, corresponding forces may be applied to squeeze both tabs 3310 at the same time, to actuate the mechanical linkages (as depicted in FIGS. 34 and 37) within the clamp manipulator 3300. Actuation of the clamp manipulator 3300 will cause tension element 3341 to be pulled in a proximal direction as depicted by arrow 33C, whereupon the clamp arms 3350 are opened, as depicted by arrows 33E to allow fluid flow through the lumen 3360. As the clamp arms 3350 are urged open, a clamp spring 3355 is energized, such that clamp spring would urge the clamp arms to a closed position, but for the tension applied via tension element 3341. The clamp actuator 3300 additionally is mechanically linked to the funnel portion 3305 of needle receptor 3301, such that as the one or more tabs 3310 are pressed, the funnel portion is urged in a distal direction, as shown by the force arrows 33E.

FIG. 34 depicts a cross-section view of the internal elements of the needle receptor 3401, and the clamp manipulator 3400. The needle 3421 is depicted as having been advanced through the mouth of the funnel 3405, and through the elastic sealing material 3465, and displacing a spring mounted sealing rod 3464. The needle receptor 3401 provides, in this embodiment, 2 paths for alternating needle penetration when the blood system is being accessed, so as to afford healing of the skin subsequent to needle penetration, prior to the subsequent access. The needle 3421 enters along an axis the intersects tangentially with a spherical chamber 3470, which is in fluid communication with the lumen 3460. It is contemplated that the spherical chamber 3470 may alternatively be a non-spherical shape, for example ovoid, but in any embodiment, it is preferred that sharp corners are avoided, so as to avoid eddies or poorly flowing regions in the chamber that would otherwise promote clotting or biological build up in the poorly flowing region. It is recognized that a spherical chamber, having tangentially located ports 3471, promotes even flow through the entirety of the chamber, during the period of time when blood is flowing through the device, and additionally upon being flushed with saline, will effectively flush the blood material from the device, such that the closed volume, when not being accessed remains filled with the saline flush. FIG. 34 further depicts the one or more tabs 3410, which upon being released for movement by the pressing of the palpable button (not shown), each of the tabs 3410, being palpable through the skin, may be urged by the operator to move, and overcome the resistance of tab spring, The movement of the tab 3410, in turn, acts upon mechanical linkages a portion of which is shown in FIG. 34, where first rigid link 3412, connected to the tab via first pivot 3413. The mechanical output from pressing upon tabs 3410 is depicted in FIG. 35.

Figure 35:
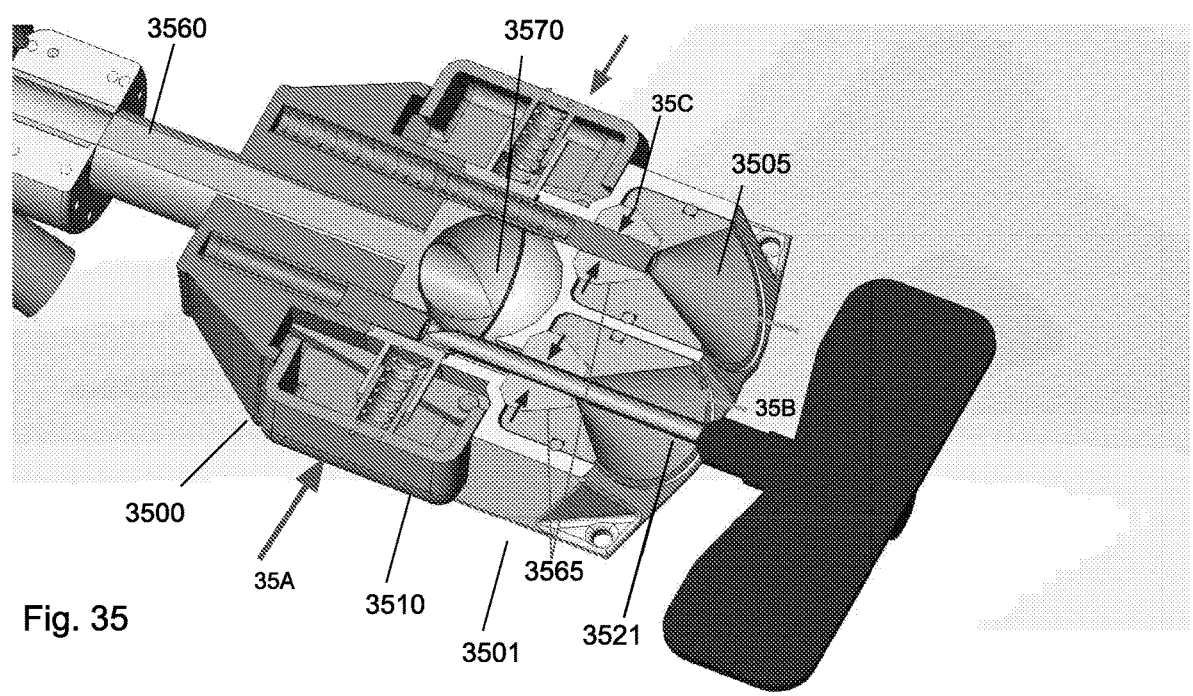
FIG. 35 shows illustrative apparatus in accordance with principles of the invention.

FIG. 35 depicts the needle receptor 3501 and clamp manipulator 3500. In FIG. 35, the one or more tabs 3510 are depicted as having been pressed and moved inwards towards the spherical chamber 3570, in the direction depicted by arrow 35A. The movement of the one or more tabs 3510, in turn acts upon a series of mechanical linkages to cause the funnel 3505 of the needle receptor to move in the direction depicted by arrows 35B, and applying compressive force to elastic sealing material 3565, which due to being constrained from movement by the construction of the clamp manipulator 3500, responds by compressing axially, as depicted by the arrows 35C, thereby forming a seal around the needle 3521. The movement of the one or more tabs 3510 is similarly conveyed by mechanical linkages to cause the clamp to open, as will be discussed.

Figure 36:
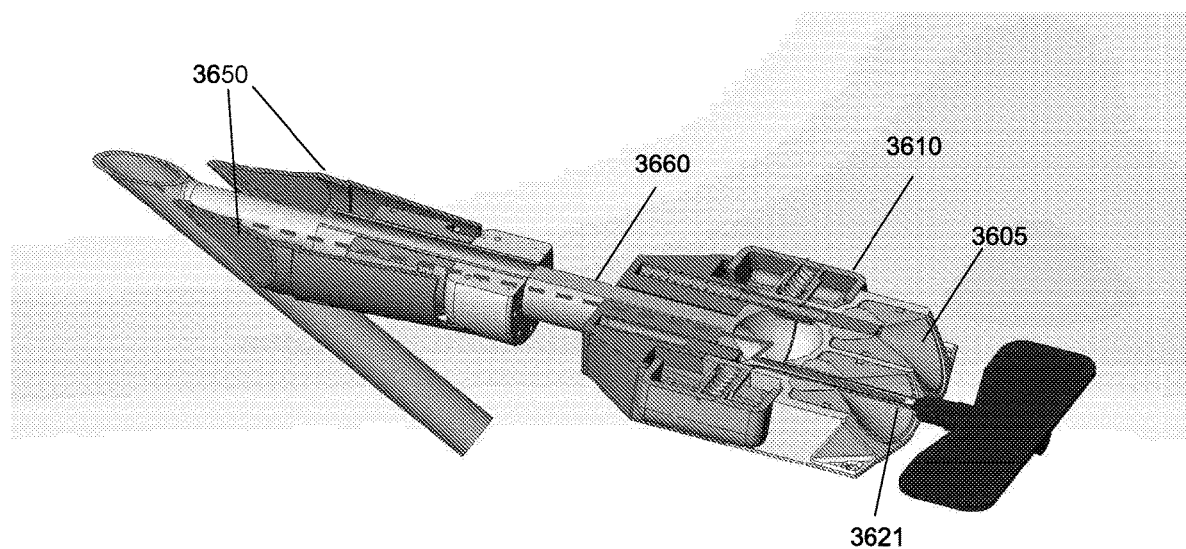
FIG. 36 shows illustrative apparatus in accordance with principles of the invention.

FIG. 36 depicts one embodiment of the subcutaneously implanted device while in a state allowing blood flow therethrough. In this embodiment, the one or more tabs 3610 are urged inwards, as previously discussed, and the funnel 3605 has been urged against sealing material 3665 to seal tightly around needle 3621. Additionally, clamp arms 3650 have been caused to open, such that there is now fluid communication between the native body blood vessel, the lumen 3660, the spherical chamber 3670, and the interior of the needle 3621. In this manner, blood is able to flow through the fluid pathway, to allow a medical procedure, such as dialysis to occur. By using two devices in tandem, it is anticipated that blood could be withdrawn from an anastomosis with the arterial system, or a graft, flow through the subcutaneously implanted device, and be delivered to a dialysis machine outside of the body. After the blood is filtered or treated, the blood may be returned through a second device anastomosed to a venous system, or graft, such that the blood flows through the needle, then through the lumen, and to the venous system. It is contemplated that in a less preferred use, the direction of flow through the device may be reversed after a period of time, where an amount of blood is removed from the patient, treated, and returned through the same device back into the blood system of the patient.

FIG. 37 is different view of the device in the same condition depicted in FIG. 36, and depicts the clamp arms 3750 having been opened by the action the one or more tabs 3710, acting via mechanical linkages comprising at least a second rigid link 3744, which is secured to the body of the tab at one end, and to a cable puller 3742 at the other end. The second rigid link 3744 serves to transfer the movement of the tab 3710 into a proximally directed (in a direction away from the anastomosis) movement of puller 3742. The proximally directed movement of the puller in turn pulls on the tension element 3741, which may be a cable or tension rod. The tension element 3741 is secured at its distal terminus to a fixation element 3743, and acts in cooperation with the clamp arms, to open the clamp arms as the fixation element is moved proximally. This may be accomplished, for example, by pins or protruding elements (as can be seen with reference to FIG. 1) affixed to the fixation element 3743, that ride in cam slots 3745 in the clamp arms 3750, such that the pins riding in the angled cam slots 3745 force the clamp arms to open, when the puller 3742 is moved proximally, It is understood that a variety of mechanical linkage arrangement may alternatively be utilized to clause the clamp to open, and in light of this teaching, those of ordinary skill in the art can generate additional embodiments and modifications without departing from the spirit of or exceeding the scope of the principles of the invention.

Figure 38:
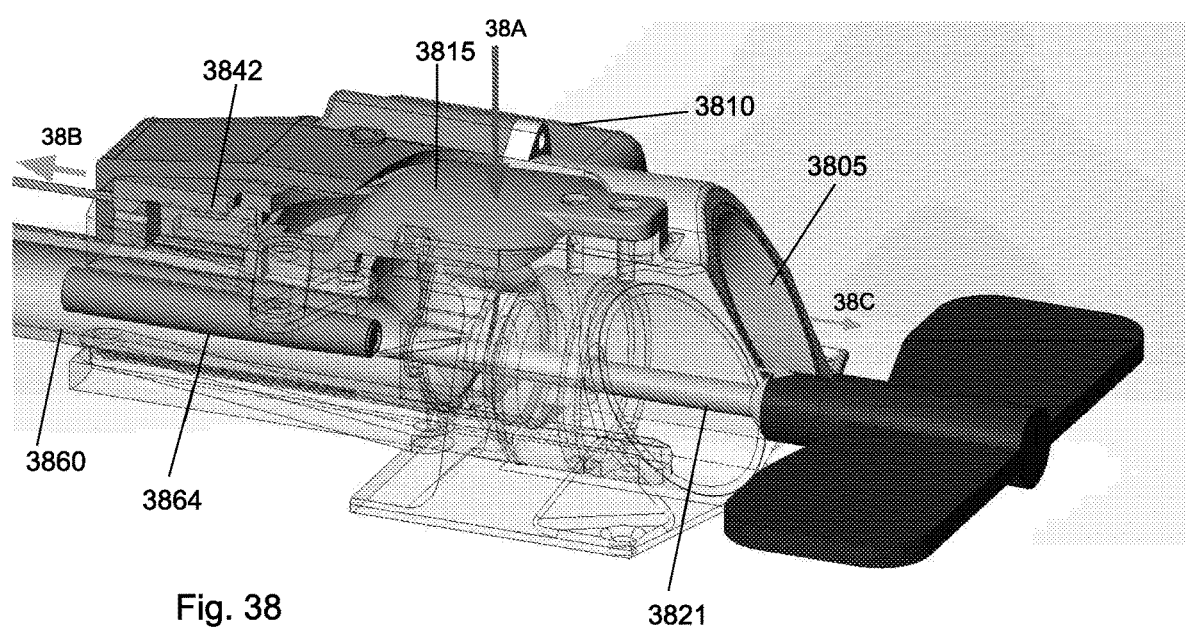
FIG. 38 shows illustrative apparatus in accordance with principles of the invention.

FIG. 38 depicts the device actions to be performed after the medical procedure, typically blood dialysis, has been completed, and the fluid pathway has been preferably flushed with saline, or any other suitable fluid to clear the pathway. In order to seal off the lumen 3860, the user depresses the palpable button 3815 in the direction shown by arrow 38A, causing the button to revert from the second state to the first state. While the button remained in the second state, the inward movement of the one or more tabs was restrained; and as the button enters the first state, the tabs are urged back to their original position by the springs (see tab springs 3411 of FIG. 34). The movement of the tabs to their original position reverses the movement of the mechanical linkages described previously, such that the clamp arms are caused to clamp and seal the lumen 3860, as the tension upon the tension element is released (represented by the arrow 38B, and the puller 3842 returns to its original position. Additionally, the tab movement allows the ring seal formed by the elastomeric material around the needle 3821 to release, as the funnel portion 3805 is moved proximally in the direction shown by arrow 38C. As needle 3821 is withdrawn, the spring loaded sealing rod 3864 is urged against the retreating needle, until such a point as the sealing rod is through the sealing material, thereby completing a seal in the proximal end of the fluid pathway while the device remains in an idle position. Apparatus and methods described herein are illustrative. Apparatus and methods of the invention may involve some or all of the features of the illustrative apparatus and/or some or all of the steps of the illustrative methods. The steps of the methods may be performed in an order other than the order shown and described herein. Some embodiments of the invention may omit steps shown and described in connection with the illustrative methods. Some embodiments of the invention may include steps that are not shown and described in connection with the illustrative methods.

The invention may be operational with numerous other general purpose or special purpose computing system environments or configurations. For example, control of expandable, contractible and otherwise moveable apparatus may be controlled by a computer system. Examples of well-known computing systems, environments, and/or configurations that may be suitable for use with the invention include, but are not limited to, personal computers, server computers, hand-held or laptop devices, mobile phones and/or other personal digital assistants ("PDAs"), multiprocessor systems, microprocessor-based systems, set top boxes, programmable consumer electronics, network PCs, minicomputers, mainframe computers, distributed computing environments that include any of the above systems or devices, and the like. In a distributed computing environment, devices that perform the same or similar function may be viewed as being part of a "module" even if the devices are separate (whether local or remote) from each other.

The invention may be described in the general context of computer-executable instructions, such as program modules, being executed by a computer. Generally, program modules may include routines, programs, objects, components, data structures, etc., that perform particular tasks or store or process data structures, objects and other data types. The invention may also be practiced in distributed computing environments where tasks are performed by separate (local or remote) processing devices that are linked through a communications network. In a distributed computing environment, program modules may be located in both local and remote computer storage media including memory storage devices.

Although the invention has been described in terms of particular embodiments and applications, one of ordinary skill in the art, in light of this teaching, can generate additional embodiments and modifications without departing from the spirit of or exceeding the scope of the principles of the invention. Accordingly, it is to be understood that the drawings and descriptions herein are proffered by way of example to facilitate comprehension of the invention and should not be construed to limit the scope thereof. Persons skilled in the art will appreciate that the present invention can be practiced by other than the described embodiments, which are presented for purposes of illustration rather than of limitation.

Thus, systems and methods for hydraulically controlled arterial/venous access, as well as mechanical linkage enabled arterial/venous access, have been provided. Persons skilled in the art will appreciate that the present invention can be practiced by other than the described embodiments, which are presented for purposes of illustration rather than of limitation. The present invention is limited only by the claims that follow.

What is claimed is:

1. A subcutaneous vascular access device designed for repeated use comprising:

At least a first needle receptor, wherein said first needle receptor is located on a proximal end of said vascular access device and is arranged to accept a needle having a distal tip that is inserted from outside the body, and to provide positioning means for the alignment of said needle;

a lumen having at least a first location, second location and third location, wherein said lumen is arranged to contact said needle receptor at said first location and with said lumen being arranged to be anastomosed to a native body lumen at said second location, with said second location also serving as a distal end of said vascular access device;

a lumen clamping means comprising:

at least two clamping members arranged to compress said lumen at said third location between said first location and said second location, thereby sealing said lumen between said anastomosis and said first location, and prohibiting fluid communication with said native body lumen;

a mechanically driven member arranged to be energized to cause diametrically opposed motion of the said at least two clamping members, thereby decompressing said lumen to provide fluid communication between said native body lumen and said first location; and a clamp manipulator comprising at least a first tab mechanically linked to said mechanically driven member, wherein the depressing of said first tab causes said mechanically driven member to be energized;

wherein said positioning means comprises:

a funnel shaped member comprising:

a gradually decreasing opening arranged to slidably accept said distal tip of said needle, wherein said opening serves to center said needle relative to said funnel shaped member;

a channel arranged to slidably accept said needle following the alignment of said needle with said channel upon centering in said funnel shaped member, whereupon said needle may be inserted into said channel;

a sealing means located in said channel, wherein said sealing means serves to seal any gaps between said needle and said channel, with said channel being in fluid communication with said lumen.

2. The device of claim 1, wherein said sealing means is further arranged to coaxially and slidably encompass a push member, wherein said push member provides resistance to sliding insertion of said needle, whereupon said push member is displaced during needle insertion.

3. The device of claim 2, wherein said push member displacement causes fluid communication to be achieved between said needle and said lumen.

4. The device of claim 1, wherein said first tab is mechanically linked to said sealing means, wherein said depressing of said first tab further causes said sealing means to tightly seal around said needle.

5. The device of claim 1, wherein said first location of said lumen further comprises a hollow spherical member, in fluid communication with said second location of said lumen.

6. The device of claim 1, wherein said clamp manipulator further comprises at least a second tab mechanically connected to said mechanically driven member, wherein the depressing of said second tab causes said mechanically driven member to be energized, with said first and said second tab arranged to cooperatively energize said mechanically driven member.

7. The device of claim 6, wherein said clamp manipulator further comprises locking means capable of alternating between a locked and unlocked state, wherein said locking means, when in said locked state, prevents said mechanically driven member from being energized until said locking means has been unlocked.

8. The device of claim 7, wherein said locking means is arranged to unlock in response to the application of pressure to said locking means, such that said mechanically driven member may then be energized.

9. The device of claim 1, wherein said at least a first tab is palpable from outside the body.

10. The device of claim 1, wherein said needle receptor is palpable from outside the body.

11. The device of claim 1, wherein said device further comprises a second needle receptor, with said receptors being located such that said needle may be introduced at a plurality of locations.

12. A kit for access to bodily lumens enabling a procedure to be completed on fluid removed therefrom prior to the return of such fluid, comprising:
   a first device as claimed in claim 1, wherein said first device is arranged to be implanted such that said native bodily lumen consists of an artery; and
   a second device as claimed in claim 1, wherein said second device is arranged to be implanted such that said native bodily lumen consists of a vein;
wherein said first device serves to enable the removal of fluid from said artery, and said second device serves to infuse said fluid into said vein following said procedure.

13. A subcutaneous vascular access device designed for repeated use comprising:
   a first needle receptor, wherein said first needle receptor is located on a proximal end of said device and is arranged to accept a needle having a distal tip that is inserted from outside the body, and said first needle receptor further comprises:
      a coaxially oriented funnel shaped member arranged to center the placement of said needle in said first needle receptor, wherein said funnel shaped member comprises:
         a gradually decreasing opening arranged to slidably accept the distal tip of said needle, wherein said opening serves to center said needle relative to said funnel shaped member;
         a channel arranged to slidably accept said needle following the alignment of said needle with said channel upon centering in said funnel shaped member, whereupon said needle may be inserted into said channel;
      a sealing means located in said channel, wherein said sealing means serves to seal any gaps between said needle and said channel;
   a hollow spherical member arranged to be intersected by said Funnel shaped member;
   a lumen, wherein said lumen is arranged to intersect said spherical member at a first location and with said lumen being arranged to be anastomosed to a native body lumen at a second location, with said second location also serving as a distal end of said device, thereby causing fluid communication between said funnel shaped member, said hollow spherical member and said lumen;
   a lumen clamping means comprising:
      at least two clamping members arranged with an elastic member which serves to compress said lumen at a location between said first location and said second location, thereby providing a seal along said anastomosis and prohibiting fluid flow therethrough;
      a mechanically driven member arranged to be energized to oppose the restriction of said elastic member to cause diametrically opposed motion of the said at least two clamping members thereby decompressing said lumen to provide fluid communication between said native body lumen and said first location; and
   a clamp manipulator comprising at least a first tab arranged to act upon said mechanically driven member, wherein the depressing of said first tab causes said mechanically driven member to be energized, thereby providing fluid communication through said lumen.

14. The device of claim 13, wherein said funnel shaped member intersects with said hollow spherical member at a position that is tangential to the hollow spherical member, thereby promoting laminar flow of fluid within said hollow spherical member.

15. The device of claim 13, wherein said clamp manipulator further comprises at least a second tab arranged to act upon said mechanically driven member.

16. The device of claim 13, wherein said clamp manipulator further comprises locking means having a locked and an unlocked state, wherein said locking means in said locked state secures said at least one tab, and prevents said mechanically driven member from being energized until said locking means enters an unlocked state.

17. The device of claim 16, wherein said locking means is arranged to unlock following the application of pressure to said locking means while in said locked state.

18. The device of claim 13, wherein said device further comprises at least a second needle receptor, with said receptors being located such that said needle may be introduced at a plurality of locations.

19. The device of claim 13, wherein said at least two clamping members are further arranged to contact said device lumen in an orientation substantially parallel with said bodily lumen, wherein said orientation serves to provide a seal with the native body lumen without creating flow disruptions or stagnations in said native body lumen or in said device lumen.

* * * * *